United States Patent
Weier et al.

(12) 
(10) Patent No.: US 6,509,361 B1
(45) Date of Patent: Jan. 21, 2003

(54) 1,5-DIARYL SUBSTITUTED PYRAZOLES AS P38 KINASE INHIBITORS

(75) Inventors: Richard M. Weier, Lake Bluff; Joyce Z. Crich, Glenview; Xiang Dong Xu, Gurnee; Paul W. Collins, Deerfield, all of IL (US)

(73) Assignee: Pharmacia Corporation, Saint Louis, MO (US)

( * ) Notice: Subject to any disclaimer, the term of this patent is extended or adjusted under 35 U.S.C. 154(b) by 0 days.

(21) Appl. No.: 09/674,653

(22) PCT Filed: May 12, 1999

(86) PCT No.: PCT/US99/07036
§ 371 (c)(1),
(2), (4) Date: Feb. 12, 2001

(87) PCT Pub. No.: WO99/58523
PCT Pub. Date: Nov. 18, 1999

(51) Int. Cl.$^7$ .................. A61K 31/4439; C07D 401/04

(52) U.S. Cl. .................. 514/341; 546/275.4; 546/256; 544/360; 514/252; 514/333

(58) Field of Search ................. 514/341, 252, 514/333; 546/275.4, 256; 544/360

(56) References Cited

U.S. PATENT DOCUMENTS 2,833,779 A * 5/1958 Fields et al. ............. 546/275.4
5,434,178 A * 7/1995 Talley et al. ................ 514/406

* cited by examiner

*Primary Examiner*—C. S. Aulakh
(74) *Attorney, Agent, or Firm*—David M. Gryte, Esq.; Harness, Dickey & Pierce, P.L.C.

(57) ABSTRACT

The present invention contemplates 1,5-diaryl-substituted pyrazole compounds that, inter alia, inhibit the activity of p38 MAP kinase. Also contemplated by the invention are processes for the preparation of the contemplated compounds and for the use of a contemplated compound in treating a mammalian host having a p38 kinase- or TNF-mediated disease.

57 Claims, No Drawings

1,5-DIARYL SUBSTITUTED PYRAZOLES AS P38 KINASE INHIBITORS

CROSS-REFERENCE TO RELATED PATENT APPLICATIONS

This patent application claims priority to PCT Application PCT/US99/07036 (filed May 12, 1999 and published as International Publication No. WO 99/58523 on Nov. 18, 1999), which, in turn, claims priority to U.S. Provisional Patent Application No. 60/085,494 (filed on May 14, 1998). The entire text of each of the above patent applications is incorporated by reference in this patent application.

TECHNICAL FIELD

This invention is directed to kinases inhibitors, and more particularly to 1,5-diaryl substituted pyrazole compounds that, inter alia, inhibit the activity of mitogen-activated protein kinases, compositions of those inhibitors, intermediates for the syntheses of those compounds, and processes for treating pathological mitogen-activated protein kinase activity.

BACKGROUND OF THE INVENTION

Mitogen-activated protein (MAP) kinases are a family of proline-directed serine/threonine kinases that activate their substrates by dual phosphorylation. The kinases are activated by a variety of signals including nutritional and osmotic stress, UV light, growth factors, endotoxin and inflammatory cytokines.

The p38 MAP kinase group is a MAP family of various isoforms, including p38, p38 and p38, and is responsible for phosphorylating and activating transcription factors (e.g. ATF2, CHOP and MEF2C) as well as other kinases (e.g. MAPKAP-2 and MAPKAP-3). The p38 isoforms are activated by bacterial lipopolysaccharide, physical and chemical stress and by pro-inflammatory cytokines, including tumor necrosis factor alpha (TNF-) and interleukin-1 (IL-1). The products of the p38 phosphorylation mediatethe production of inflammatory cytokines, including TNF and IL-1, and cyclooxygenase-2.

TNF-a is a cytokine produced primarily by activated monocytes and macrophages. Excessive or unregulated TNF production has been implicated in mediating a number of diseases. Recent studies indicate that TNF has a causative role in the pathogenesis of rheumatoid arthritis. Additional studies demonstrate that inhibition of TNF has broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

IL-8 is another pro-inflammatory cytokine, which is produced by mononuclear cells, fibroblasts, endothelial cells, and keratinocytes, and is associated with conditions including inflammation.

IL-1 is produced by activated monocytes and macrophages and is also involved in the inflammatory response. IL-1 plays a role in many pathophysiological responses including rheumatoid arthritis, fever and reduction of bone resorption.

TNF, IL-1 and IL-8 affect a wide variety of cells and tissues and are important inflammatory mediators of a wide variety of disease states and conditions. The inhibition of these cytokines by inhibition of the p38 kinase is of benefit in controlling, reducing and alleviating many of these disease states.

Various pyrazoles have previously been described. For example, WO 95/33727, published Dec. 14, 1995, describes substituted pyrazoles as corticotropin-releasing factor (CFR) antagonists used in the treatment of illnesses such as stress and anxiety related disorders. WO 96/21660, published Jul. 18, 1996, describes substituted pyrazoles and their use as ligands for dopamine receptors within the body. EP 0 699 438 A2, published Mar. 6, 1996, describes pyrazoles and their use as neurotensin antagonists. U.S. Pat. No. 2,833, 779, to Fields et al., describes the preparation of 1,3,5-tri-substituted pyrazoles. U.S. Pat. No. 4,957,971, to Picard et al., describes trans-6-[2-(N-heteroaryl-3,5-disubstituted) pyrazol-4-yl)ethyl- or ethenyl]tetrahydro-4-hydroxy-2H-pyran-2-ones as potent inhibitors of the enzyme 3-hydroxy-3-methylglutaryl-coenzyme A reductase, used for inhibiting cholesterol biosynthesis. U.S. Pat. No. 5,441,975, to Lee et al., describes pyrazoles that are useful for the treatment of hypercholesterolemia or atherosclerosis in mammals. WO 93/04052, published Mar. 4, 1993, describes pyrazole having ACAT inhibitory activity. U.S. Pat. No. 5,102,893, to Picard et al., describes trans-6-[2-(N-heteroaryl-3,5-disubstituted)pyrazol-4-yl)ethyl- or ethenyl]tetrahydro-4-hydroxy-2H-pyran-2-ones which are potent inhibitors of the enzyme 3-hydroxy-3-methylglutaryl-coenzyme A reductase and useful as hydrolipidemic and hypocholesterolemic agents. WO 94/22838, published Oct. 13, 1994, describes pyrazole compounds having angiotensin II antagonism which are useful in preventing or treating hypertension, congestive heart failure, chronic renal failure, aldosteronism, and increased intralocular pressure.

WO 92/19615, published Nov. 12, 1992, describes pyrazoles, pyrazolines and tetrahydropyridazine having fungicidal activity. U.S. Pat. No. 5,232,940, to Hatton et al., describes a N-Phenylpyrazole and their use against arthropod, plant nematode, helminth and protozoan pests. WO 95/01340, published Jan. 12, 1995, describes novel pyrazole compounds having agrohorticultural bactericidal effect. U.S. Pat. No. 5,201,938, to Costales, describes novel substituted N-pyrazolyl-1,2,4-triazolo[1,5-c]-pyrimidine-2-sulfonamide compounds and their use as herbicides. WO 93/09100, published May 13, 1993, describes trizolocarboxamides with herbicidal activity used to control blackgrass, wild oats, crabgrass, giant foxtail, and barnyardgrass. WO 94/29300, published Dec. 22, 1994, describes pyrazoles 3-substituted by a heterocyclic ring and their use as agricultural fungicides. WO 96/37477, published Nov. 28, 1996, describes substituted pyrazoles and their use against animal parasites and pests and as insecticides, and fungicides.

Pyrazoles have also been described for use in the treatment of inflammation. U.S. Pat. No. 5,242,940, to Wachter and Murray, describes 1,5 heterocyclic pyrazoles and their use in alleviating inflammatory and cardiovascular disorders in mammals. U.S. Pat. No. 5,134,142, to Matsuo, et al., describes 1,5 diaryl substituted pyrazoles and 1,3 diaryl substituted pyrazoles useful in the treatment of inflammation, pain, thrombosis and rheumatism. U.S. Pat. No. 5,466,823, to Talley et al., describes a class of pyrazole benzenesulfonamide compounds and their use in treating inflammation and inflammation-related disorders.

The invention's pyrazolyl compounds are found to show usefulness, inter alia, as p38 kinase inhibitors.

BRIEF SUMMARY OF THE INVENTION

In accordance with the present invention, it has been found that certain 1,5-diaryl pyrazoles are effective for inhibition of mitogen-activated protein (MAP) kinases. Mitogen-activated protein kinases are believed to be associated with, inter alia, the mediation of a number of inflammatory diseases. In particular, it has been found that these certain 1,5-diaryl pyrazoles are effective for the inhibition of the p38 MAP kinase group, a sub-family of MAP kinases. The compounds of interest here have structures that correspond to Formula I, below, whose substituent groups are defined hereinafter, or a pharmaceutically acceptable salt thereof.

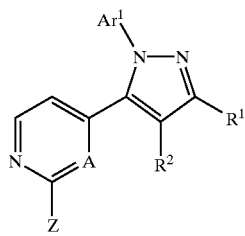

I

A process for treating a host mammal having a condition associated with pathological p38 MAP kinase activity is also contemplated. That process comprises administering a compound described herein in a p38 MAP kinase enzyme-inhibiting effective amount to a mammalian host having such a condition. The use of administration repeated a plurality of times is particularly contemplated.

The p38 MAP kinase sub-family have various isoforms, including p38, p38 and p38 and is responsible for phosphorylating and activating transcription factors (e.g. ATF2, CHOP and MEF2C) as well as other kinases (e.g. MAPKAP-2 and MAPKAP-3). The p38 isoforms are activated by bacterial lipopolysaccharide, physical and chemical stress and by pro-inflammatory cytokines, including tumor necrosis factor (TNF-) and interleukin-1 (IL-1). The products of the p38 phosphorylation mediate the production of inflammatory cytokines, including TNF- and IL-1, and cyclooxygenase-2.

Excessive or unregulated TNF production has been implicated in mediating a number of diseases, including rheumatoid arthritis, inflammation, inflammatory bowel disease, multiple sclerosis, asthma, and viral infections. IL-8 is another pro-inflammatory cytokine, and is associated with conditions including inflammation. Additionally, IL-1 is involved in the inflammatory response. IL-1 plays a role in many pathophysiological responses including rheumatoid arthritis, fever and reduction of bone resorption. TNF-, IL-1 and IL-8 affect a wide variety of cells and tissues and are important inflammatory mediators of a wide variety of disease states and conditions. The inhibition of the production of these cytokines by inhibition of the p38 kinase is of benefit in controlling, reducing and alleviating many of these disease states.

DETAILED DESCRIPTION OF PREFERRED EMBODIMENTS

As already noted, the present invention is directed to compounds that inhibit the activity of p38 MAP kinase, among other activities, as well as to processes for using such a compound in treating a condition mediated by that enzyme or TNF. One embodiment of the present invention is directed to a 1,5-diaryl pyrazole compound that, inter alia, inhibits the activity of the p38 mitogen-activated protein kinase enzyme. That compound corresponds in structure to Formula I below, or a pharmaceutically-acceptable salt thereof:

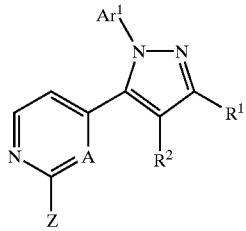

I wherein A is =N— or =CH—;
Ar$^1$ is an aryl group that is optionally substituted by one or more substituents selected from the group consisting of a halogen, hydrocarbyl, hydrocarbyloxy, nitro, cyano, perfluorohydrocarbyl, trifluoromethylhydrocarbyl, perfluorohydrocarbyloxy, hydroxy, mercapto, hydroxycarbonyl, aryloxy, arylthio, sulfonyl or sulfoxido, wherein the subsituent on the sulfur atom is hydrocarbyl, sulfonylamide,
wherein the substituents on the sulfonamido nitrogen atom are hydrido or hydrocarbyl, arylamino, arylhydrocarbyl, aryl, heteroaryloxy, heteroarylthio, heteroarylamino, heteroarylhydrocarbyl, hydrocarbyloxycarbonyl-hydrocarbyl, heterocyclooxy, hydroxycarbonyl-hydrocarbyl, heterocyclothio, heterocycloamino, cyclohydrocarbyloxy, cyclohydrocarbylthio, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonylhydrocarbyloxy, hydrocarbyloxycarbonylhydrocarbyloxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino, N-monosubstituted or N,N-disubstituted aminohydrocarbyl group,
wherein the substituent(s) on the aminohydrocarbyl nitrogen atom are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the aminohydrocarbyl nitrogen and two substituents attached thereto form a 5- to 8-membered heterocyclic or heteroaryl ring group, amino, and a N-monosubstituted or N,N-disubstituted amino group, wherein the substituent(s) on the amino nitrogen are selected from the group consisting of hydrido, hydrocarbyl, aryl, arylhydrocarbyl, cyclohydrocarbyl, arylhydrocarbyloxycarbonyl, hydrocarbyloxycarbonyl, hydrocarboyl, arylsulfonyl, and hydrocarbylsulfonyl or wherein the amino nitrogen and two substituents attached thereto form a 5- to 8-membered heterocyclic or heteroaryl ring group;

Z is selected from the group consisting of hydrido, hydrocarbyl, halogen, carboxy, cyano, azido, hydrocarbylsulfonyl, carbonyloxyhydrocarbyl, carbonylamido, and —X—Y wherein —X is —O, —S or —NQ, —Y is hydrido, hydrocarbyl or hydrocarbylaryl, Q is hydrido, hydrocarbyl, hydroxylhydrocarbyl, 2-, 3-, or 4-pyridylhydrocarbyl, or arylhydrocarbyl;

$R^1$ is selected from the group consisting of an azido, hydrido, hydrocarbyl, amido, hydrocarbylamino, halohydrocarbyl, perhalohydrocarbyl and an aryl substituent that is optionally substituted by one or more substituents selected from the group consisting of a halogen, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonylhydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonyl-hydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino and N-monosubstituted or N,N-disubstituted aminohydrocarbyl group, wherein the substituent(s) on the amino-hydrocarbyl nitrogen atom are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the aminohydrocarbyl nitrogen and two substituents attached thereto form a 5- to 8-membered heterocyclic or heteroaryl ring group; and $R^2$ is selected from the group consisting of an azido, hydrido, hydrocarbyl, amido, halohydrocarbyl, perhalohydrocarbyl, hydrocarbyloxycarbonyl, N-piperazinylcarbonyl, aminocarbonyl, piperazinyl and an aryl group that is substituted by one or more substituents, said one or more substituents being selected from the group consisting of a halogen, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbyamino, arylhydrocarbyloxy, arylhydrocarbylthio, arylhydrocarbylamino, heterocyclic, heteroaryl, hydroxycarbonyl-hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonyl-hydrocarbyloxy, hydrocarbyloxycarbonylhydrocarbyl, hydrocarbylhydroxycarbonyl-hydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino and N-monosubstituted or N,N-disubstituted aminohydrocarbyl group, wherein the substituent(s) on the aminohydrocarbyl nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the aminohydrocarbyl nitrogen and two substituents attached thereto form a 5- to 8-membered heterocyclic or heteroaryl ring group; and provided that when A is =CH— and Z is hydrido, hydrocarbyl, halogen, or hydrocarboyl:
1) $Ar^1$ is other than an aryl group that is substituted by one or more substituents selected from the group consisting of a hydrido, halogen, hydrocarbyl, perfluorohydrocarbyloxy, nitro, perfluorohydrocarbyl, amino, aminosulfonyl, halohydrocarbyloxyhydrocarbyl, hydroxy, hydrocarbylsulfonylamino, hydrocarbylsulfonly, acetylamino, carbonylhydrocarbylamino, perfluorohydrocarbylsulfonyl, hydrocarbylamino, carbonyl monosubstituted amino, carbonyl, hydrocarbylthio, hydroxyhydrocarbyl, arylhydrocarbyl, hydrocarbyloxyhydrocarbyl, hydrocarbyloxycarbonyl, hydrocarbyloxyarylhydrocarbyl, halohydrocarbyloxy, hydrocarbyloxyhydrocarbyl; or 2) $R^1$ is other than hydrido, hydrocarbyl, aryl, haloaryl, cyanoaryl, hydroxyaryl, hydrocarbylaryl, cyano, perfluorohydrocarbyl, hydroxyhydrocarbyl, arylhydrocarbyl, carboxy, hydrocarbyloxycarbonyl, hydrocarboylhydrocarbyl, aminocarbonyl, arylhydrocarbyl-hydrocarboyl-hydrocarbyl monosubstituted amino carbonyl, hydrocarbyl-hydrocarboyl-hydrocarbyl monosubstituted amino carbonyl, hydrocarbyl-hydrocarbylhydrocarboyl-hydrocarbyl monosubstituted amino carbonyl, hydrocarbyl-hydroxy-disubstituted amino carbonylhydrocarbyl, or a six membered heteroaryl group substituted by a nitrogen atom; or 3) $R^2$ is other than hydrido, carboxy, hydrocarbyloxycarbonyl, halogen, or aryl.

In particularly preferred practice, A is =CH— so that a contemplated 5-substituent is a 4-pyridyl residue, as compared to being a 4-pyrimidyl residue.

When examined primarily on the basis of activity, Formula I includes three particularly preferred subclasses of compounds of high interest. One subclass of particular interest is a preferred class of compounds exhibit $IC_{50}$ in vitro activities in the assay discussed hereinafter and shown in Table I of about 1.5 to less than (<) 10 μM. This embodiment comprises compounds of Formula I or a pharmaceutically acceptable salt thereof wherein:

$Ar^1$ is an aryl group that is substituted by a group selected from fluorine, or lower hydrocarbyl;

$R^1$ is hydrido, or lower hydrocarbyl;

$R^2$ is selected from the group consisting of hydrido, lowerhydrocarbyl and aminocarbonyl;

Z is hydrido, or —X—Y;
—X is —O or —NQ;
Q is aryl lower hydrocarbyl; and
—Y is hydrido or lower hydrocarbyl.

A more preferred subclass of compounds exhibit $IC_{50}$ in vitro activities in the assay discussed hereinafter of about 1.0 to less than (<) 1.5 μM. This more preferred embodiment comprises those compounds of Formula I or a pharmaceutically acceptable salt thereof wherein:

$Ar^1$ is an aryl group that is substituted by one or more substituents that are lower hydrocarbyl, or halo such as flourine;

$R^1$ is hydrido, or lower hydrocarbyl;

$R^2$ is hydrido or lower hydrocarbyl;

Z is hydrido or —X—Y;
—X is —NQ;
Q is lower hydrocarbyl or hydroxyl lower hydrocarbyl; and
—Y is hydrido or lower hydrocarbyl.

The most preferred subclass of compounds of Formula I exhibit $IC_{50}$ in vitro activities in the assay discussed hereinafter and shown in Table I of less than (<) 1.0 μM. This subclass of compounds comprise those compounds of Formula I or a pharmaceutically acceptable salt thereof wherein:

$Ar^1$ is an aryl group that is substituted by one or more substituents that are lower hydrocarbyl or halo such as flourine or chlorine;

$R^1$ is hydrido, or lower hydrocarbyl;

$R^2$ is hydrido;

Z is selected cyano or —X—Y;
wherein —X is —O, or —NQ;
Q is selected from a group consisting of hydrido, lowerhydrocarbyl, aryl lower hydrocarbyl, hydroxyl lower hydrocarbyl, and 3-pyridyl lower hydrocarbyl; and —Y is hydrido, lower hydrocarbyl, or aryl lower hydrocarbyl.

It has been found that certain 1,5-diaryl pyrazoles are effective for inhibition of mitogen-activated protein (MAP) kinases. Mitogen-activated protein kinases are believed to be associated with, inter alia, the mediation of a number of inflammatory diseases. In particular, it has been found that these certain 1,5-diaryl pyrazoles are effective for the inhibition of the p38 MAP kinase group of enzymes, a subfamily of MAP.

Because of the interrelation between p38 kinase and TNF, compounds of Formula I are useful for, but not limited to, the treatment of a disorder or disease state in a human, or other mammal, that is exacerbated or caused by excessive or unregulated TNF or p38 kinase production; i.e., pathological p38 MAP kinase activity, by such mammal. Accordingly, the present invention provides not only compounds but also a method of treating a TNF-mediated disease that comprises administering an effective TNF-inhibiting amount of a compound of Formula I, or a pharmaceutically acceptable salt or tautomer thereof.

Compounds of Formula I are also useful for, but not limited to, the treatment of inflammation in a subject, and for use as an antipyretic for the treatment of fever. Compounds of the invention is useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds are further useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpesvirus.

The compounds disclosed herein are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection. The compounds are also useful for the treatment of influenza, multiple sclerosis, cancer, diabetes, systemic lupus erthrematosis (SLE), skin-related conditions such as psoriasis, eczema, burns, dermatitis, keloid formation, and scar tissue formation. Compounds of the invention are also useful to treat gastrointestinal conditions such as inflammatory bowel disease, Crohn's disease, gastritis, irritable bowel syndrome and ulcerative colitis. The compounds would also be useful in the treatment of ophthalmic diseases, such as retinitis, retinopathies, uveitis, ocular photophobia, and of acute injury to the eye tissue. The compounds of the invention can also be useful for preventing the production of cyclooxygenase-2.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional anti-inflammatory agents, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF-mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, is therefore considered a disorder mediated by TNF.

As used herein, the term "p38-mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, is therefore considered a disorder mediated by p38.

As TNF- has close structural homology with TNF (also known as cachectin), and because each induces similar biologic responses and binds to the same cellular receptor, both TNF- and TNF- are inhibited by the compounds of the present invention and thus are herein referred to collectively as "TNF" unless specifically delineated otherwise.

When examined first on the basis of structure and then functional activity among the 5-(4-pyridyl) pyrazole substituents, one observes three further subclasses of particularly preferred compounds within the compounds of Formula I. One subclass of particularly preferred compounds has structures that are represented by Formula II, below, or a pharmaceutically acceptable salt thereof:

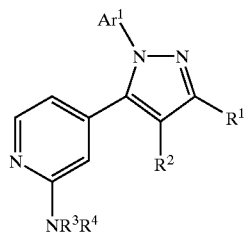

II wherein $R^3$ is hydrido, or $C_1$–$C_6$ (lower) hydrocarbyl;
$R^4$ is selected from a group consisting of hydrido, lower hydrocarbyl, aryl lower hydrocarbyl, hydroxyl lower hydrocarbyl, and 2-pyridyl lower hydrocarbyl, 3-pyridyl lower hydrocarbyl or 4-pyridyl lower hydrocarbyl;
$Ar^1$ is an aryl group that is substituted by a halogen or halo group (e.g., chlorine, fluorine and bromine), lower hydrocarbyl, or hydrocarbyloxy group;
$R^1$ hydrido, or $C_1$–$C_6$ hydrocarbyl; and
$R^2$ is hydrido, or lower hydrocarbyl.

One preferred group of compounds of Formula II noted in Table I exhibit $IC_{50}$ in vitro activities in the assay discussed hereinafter of less than (<) 10 and greater than (>) 1.5 μM. This group of compounds comprises those compounds of Formula II or a pharmaceutically acceptable salt thereof wherein:

$Ar^1$ is an aryl group that is substituted by lower hydrocarbyl;
$R^1$ is lower hydrocarbyl;
$R^2$ is hydrido;
$R^3$ is hydrido or $C_1$–$C_6$, hydrocarbyl; and
$R^4$ is $C_1$–$C_6$ hydrocarbyl or aryl lower hydrocarbyl.

A more preferred class of compounds of Formula II noted in Table I exhibits $IC_{50}$ in vitro activities in the assay discussed hereinafter of about 1.0 to less than (<) 1.5 μM. This group of compounds is comprised of those compounds of Formula II or a pharmaceutically acceptable salt thereof wherein:

$Ar^1$ is an aryl group that is substituted by lower hydrocarbyl;
$R^1$ is lower hydrocarbyl;
$R^2$ is hydrido;
$R^3$ is hydrido or lower hydrocarbyl; and
$R^4$ is lower hydrocarbyl, or hydroxyl lower hydrocarbyl.

The most preferred class of compounds of Formula II noted in Table I exhibits $IC_{50}$ in vitro activities in the assay discussed hereinafter of less than (<) 1.0 μM. This group of compounds is comprised of those compounds of Formula II or a pharmaceutically acceptable salt thereof wherein:

$Ar^1$ is an aryl group that is substituted with a lower hydrocarbyl or halogen (e.g., flourine or chlorine) group;
$R^1$ is hydrido, or lower hydrocarbyl;
$R^2$ is hydrido;
$R^3$ is hydrido or lower hydrocarbyl; and
$R^4$ is aryl lower hydrocarbyl, hydroxyl lower hydrocarbyl, or 3-pyridyl lower hydrocarbyl.

A second preferred subclass of compounds within Formula I has structures that correspond to Formula III, or a pharmaceutically acceptable salt thereof wherein:

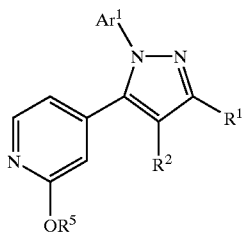

III $R^5$ is hydrido, $C_1$–$C_6$ hydrocarbyl, or aryl lower hydrocarbyl;
$Ar^1$ is an aryl group that is substituted with a halogen (e.g., chlorine, fluorine or bromine), lower hydrocarbyl, or hydrocarbyloxy group;
$R^1$ is $C_1$–$C_6$ hydrocarbyl; and
$R^2$ is hydrido.

Preferred compounds of Formula III exhibit $IC_{50}$ in vitro activities in the assay discussed hereinafter and shown in Table I of less than (<) 10 and greater than (>) 1.0 μM. This group of compounds is comprised of those compounds of Formula III or a pharmaceutically acceptable salt thereof wherein:

$Ar^1$ is an aryl group that is substituted by a lower hydrocarbyl group;
$R^1$ is lower hydrocarbyl;
$R^2$ is hydrido; and
$R^5$ is lower hydrocarbyl or aryl lower hydrocarbyl.

A third subclass of preferred compounds within Formula I have structures represented by Formula IV or a pharmaceutically acceptable salt thereof wherein:

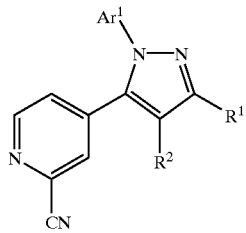

Ar¹ is an aryl group that is substituted by a halogen (e.g., chlorine, fluorine or bromine), lower hydrocarbyl or a hydrocarbyloxy group;

R¹ is lower hydrocarbyl; and

R² is hydrido or lower hydrocarbyl.

Preferred compounds of Formula IV exhibit $IC_{50}$ in vitro activities in the assay discussed hereinafter and shown in Table I of less than (<) 10 and greater than (>) 1.0 μM. This group of compounds comprises of those compounds of Formula IV or a pharmaceutically acceptable salt thereof wherein:

Ar¹ is an aryl group that is substituted by a lower hydrocarbyl group;

R¹ is lower hydrocarbyl; and

R² is hydrido.

The term "hydrido" denotes a single hydrogen atom (H). This hydrido radical can be attached, for example, to an oxygen atom to form a hydroxyl radical or two hydrido radicals can be attached to a carbon atom to form a methylene (—CH₂—) radical.

The word "hydrocarbyl" is used herein as a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., alkyl, methyl or dodecenyl. Exemplary hydrocarbyl groups contain a chain of 1 to about 12 carbon atoms, and preferably one to about 10 carbon atoms. Most preferred are lower hydrocarbyl radicals that contain one to about six carbon atoms.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a —C(O)— functionality is referred too as a hydrocarboyl group in as much as there is no ambiguity in using that suffix. As a skilled worker will understand, a substituent that cannot exist such as a $C_1$ alkenyl group is not intended to be encompassed by the word "hydrocarbyl".

Where used, either alone or within other terms such as "haloalkyl", "alkylsulfonyl", "alkoxyalkyl" and "hydroxyalkyl", "thioalkyl", the term "alkyl" embraces linear or branched saturated radicals having one to about twenty carbon atoms or, preferably, one to about twelve carbon atoms. More preferred alkyl radicals are radicals having one to about twelve carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about six carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about six carbon atoms. Examples of alkynyl radicals include ethynyl (acetylenyl), propynyl, butynyl and 4-methylbutynyl.

An alkyl group is a particularly preferred hydrocarbyl group. For ease in understanding, alkyl groups are utilized hereinbelow in the explanations of the nomenclature used herein for various substituent groups. It is to be understood, however, that the word "alkyl" is used to stand in for the less familiar word "hydrocarbyl", which encompasses not only alkyl groups, but also alkenyl and alkynyl groups.

The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl.

The term "cycloalkylalkylene" embraces alkyl radicals substituted with a cycloalkyl radical. More preferred cycloalkylalkylene radicals are "lower cycloalkylalkylene", which embrace lower alkyl radicals substituted with a lower cycloalkyl radical as defined above. Examples of such radicals include cyclopropylmethyl, cyclobutylmethyl, cyclopentylmethyl and cyclohexylmethyl.

The term "cycloalkenyl" embraces partially unsaturated carbocyclic radicals having three to twelve carbon atoms and one or two double bonds, but not necessarily conjugated ("cycloalkyldienyl"). More preferred cycloalkenyl radicals are "lower cycloalkenyl" radicals having four to about eight carbon atoms. Examples of such radicals include cyclobutenyl, cyclopentenyl and cyclohexenyl.

The term "cycloalkenylalkylene" embraces alkyl radicals substituted with a cycloalkenyl radical. More preferred cycloalkenylalkylene radicals are "lower cycloalkenylalkylene", which embrace lower alkyl radicals substituted with a lower cycloalkenyl radical, as defined above. Examples of such radicals include cyclobutenylmethyl, cyclopentenylmethyl and cyclohexenylmethyl.

The term "halo" or "halogen" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, can have either an iodo, bromo, chloro or fluoro atom within the radical. Dihalo and polyhaloalkyl radicals can have two or more of the same halo atoms or a combination of different halo radicals. "Lower haloalkyl" embraces radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl" embraces linear or branched alkyl radicals having one to about twelve carbon atoms, any one of which can be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The terms "alkoxy" and "alkyloxy" embrace linear or branched oxy-containing radicals each having alkyl portions of one to about twelve carbon atoms. More preferred alkoxy radicals are "lower alkoxy" radicals having one to six carbon atoms. Examples of such radicals include methoxy, ethoxy, propoxy, butoxy and tert-butoxy.

The term "alkoxyalkyl" embraces alkyl radicals having one or more alkoxy radicals attached to the alkyl radical to form, for example, monoalkoxyalkyl and dialkoxyalkyl radicals. The "alkoxy" radicals can be further substituted with one or more halo atoms, such as fluoro, chloro or bromo, to provide "haloalkoxy" radicals.

The term "aryl", alone or in combination, means a carbocyclic aromatic system containing one, two or three rings wherein such rings can be attached together in a pendent manner or can be fused. More preferred aryl are 6–12 membered aryl radicals. Examples of such radicals include phenyl, naphthyl, tetrahydronaphthyl, indane and biphenyl. Phenyl radicals are preferred aryl radicals.

Aryl moieties can also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl.

The term "heterocyclyl" embraces saturated, partially unsaturated and aromatically-unsaturated heteroatom-containing ring-shaped radicals, which can also be called "heterocyclyl", "heterocycloalkenyl" and "heteroaryl" respectively, where the heteroatoms are nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals can include a tetravalent nitrogen, such as in tetrazolium and pyridinium radicals.

The term "heteroaryl" embraces aromatically-unsaturated heterocyclyl radicals. Examples of heteroaryl radicals include unsaturated 5- to 10-membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl) tetrazolyl (e.g. 1H-tetrazolyl, 2H-tetrazolyl, etc.), and the like; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl), and the like; an unsaturated 5- or 6-membered heteromonocyclic group containing an oxygen atom, for example, pyranyl or furyl; unsaturated 5- or 6-membered heteromonocyclic group containing a sulfur atom, for example, thienyl; unsaturated 5- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl) and the like; unsaturated condensed heterocyclyl group containing 1 to 2 oxygen atoms and 1 to 3 nitrogen atoms (e.g. benzoxazolyl, benzoxadiazolyl, etc.); unsaturated 5- or 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3, 4-thiadiazolyl, and 1,2,5-thiadiazolyl) and the like; unsaturated condensed heterocyclyl group containing 1 to 2 sulfur atoms and 1 to 3 nitrogen atoms (e.g., benzothiazolyl or benzothiadiazolyl) and the like.

The term "heteroaryl" also embraces radicals where heterocyclyl radicals are fused with aryl radicals. Examples of such fused bicyclic radicals include benzofuran, benzothiophene, and the like.

A heterocyclyl group can have 1 to 3 substituents such as alkyl, hydroxyl, halo, alkoxy, oxo, amino and alkylamino. The term "heterocyclylalkylene" embraces heterocyclyl-substituted alkyl radicals. More preferred heterocyclylalkylene radicals are "lower heterocyclylalkylene" radicals having one to six carbon atoms and a heterocyclyl radical.

The term "alkylthio" embraces radicals containing a linear or branched alkyl radical, of one to about twelve carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

The term "alkylthioalkylene" embraces radicals containing an alkylthio radical attached through the divalent sulfur atom to an alkyl radical of one to about twelve carbon atoms. More preferred alkylthioalkylene radicals are "lower alkylthioalkylene" radicals having alkyl radicals of one to six carbon atoms. Examples of such lower alkylthioalkylene radicals include methylthiomethyl.

The term "alkylsulfinyl" embraces radicals containing a linear or branched alkyl radical, of one to about twelve carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl.

The term "sulfonyl", whether used alone or linked to other terms such as "alkylsulfonyl", or "halosulfonyl" denotes a divalent radical, —SO$_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl.

The "alkylsulfonyl" radicals can be further substituted with one or more halo atoms, such as fluoro, chloro or bromo, to provide haloalkylsulfonyl radicals. The term "halosulfonyl" embraces halo radicals attached to a sulfonyl radical. Examples of such halosulfonyl radicals include chlorosulfonyl and bromosulfonyl.

The terms "sulfamyl", "aminosulfonyl" and "sulfonamidyl" denote NH$_2$O$_2$S—. The term "carbonyl", whether used alone or with other terms, such as "alkoxycarbonyl", denotes —(C=O)—. The terms "carboxy" or "carboxyl", whether used alone or with other terms, such as "carboxyalkyl", denotes —CO$_2$—. The term "carboxyalkyl", embraces alkyl radicals substituted with a carboxy radical. More preferred are "lower carboxyalkyl", radicals that embrace carboxy-substituted lower alkyl radicals, as defined above. Examples of such lower carboxyalkyl radicals include carboxymethyl, carboxyethyl and carboxypropyl.

The term "alkoxycarbonyl" means a radical containing an alkoxy radical, as defined above, attached via an oxygen atom to a carbonyl radical. More preferred are "lower alkoxycarbonyl" radicals with alkyl portions having one to six carbons. Examples of such lower alkoxycarbonyl (ester) radicals include methoxycarbonyl, ethoxycarbonyl, propoxycarbonyl, butoxycarbonyl and hexyloxycarbonyl.

The term "alkoxycarbonylalkylene" embraces alkyl radicals substituted with an alkoxycarbonyl radical as defined above. More preferred are "lower alkoxycarbonylalkylene" radicals with alkyl portions having one to six carbons. Examples of such lower alkoxycarbonylalkylene radicals include methoxycarbonylmethylene, ethoxycarbonylmethylene, methoxycarbonylethylene and ethoxycarbonylethylene.

The term "alkylcarbonyl", includes radicals having alkyl radicals attached to a carbonyl radical. Examples of such radicals include methylcarbonyl, ethylcarbonyl, propylcarbonyl, butylcarbonyl, and pentylcarbonyl.

The term "aralkyl" embraces aryl-substituted alkyl radicals. Preferred aralkyl radicals are "lower aralkyl", having lower alkyl groups substituted with one or more aryl groups. Examples of such groups include benzyl, diphenylmethyl, triphenylmethyl, phenylethyl, and diphenylethyl. The aryl in such an aralkyl group can be additionally substituted with halo, alkyl, alkoxy, haloalkyl and haloalkoxy moieties. The terms benzyl and phenylmethyl are interchangeable.

The term "heterocyclylalkylene" embraces saturated, partially unsaturated and unsaturated heterocyclyl-substituted alkyl radicals such as pyrrolidinylmethyl, pyridylmethyl, quinolylmethyl, thienylmethyl, furylethyl, and quinolylethyl. The heteroaryl in heteroaralkyl (unsaturated heterocyclyl-substituted alkyl radicals) can be additionally substituted with halo, alkyl, alkoxy, haloalkyl and haloalkoxy groups.

The term "aryloxy" embraces aryl radicals attached through an oxygen atom to other radicals. The term "aralkoxy" embraces aralkyl radicals attached through an oxygen atom to other radicals.

The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups that are substituted with one or two alkyl radicals. Preferred are "lower alkylamino" radicals having alkyl portions having one to six carbon atoms. Suitable lower alkylamino radicals can be monosubstituted N-alkylamino or disubstituted N,N-alkylamino, such as N-methylamino, N-ethylamino, N,N-dimethylamino, N,N-diethylamino or the like.

The term "arylamino" denotes amino groups that are substituted with one or two aryl radicals, such as N-phenylamino. The "arylamino" radicals can be further substituted on the aryl ring portion of the radical as discussed previously for other aryl-containing radicals.

The term "aminocarbonyl" denotes an amide group of the formula —C(=O)NH$_2$. The term "alkylaminocarbonyl" denotes an aminocarbonyl group that has been substituted with one or two alkyl radicals on the amino nitrogen atom. Preferred are "N-alkylaminocarbonyl" and "N,N-dialkylaminocarbonyl", radicals. More preferred are "lower N-alkylaminocarbonyl" and "lower N,N-dialkylaminocarbonyl" radicals with lower alkyl portions as defined above.

The term "alkylcarbonylamino" embraces amino groups that are substituted with one or more alkylcarbonyl radicals. More preferred alkylcarbonylamino radicals are "lower alkylcarbonylamino" having lower alkylcarbonyl radicals as defined above attached to amino radicals. The term "alkylaminoalkylene" embraces radicals having one or more alkyl radicals attached to an aminoalkyl radical.

Tables 1 through 14 hereinafter illustrate compounds of Formulas II, III and IV that illustrate preferred substituent groups other than hydrido for one of substituents Ar$^1$, R$^1$, R$^2$, R$^3$, R$^4$, and R$^5$. The remaining groups Ar$^1$, R$^1$, R$^2$, R$^3$, R$^4$, and R$^5$ illustrated for each structure shown in a compound table are as discussed elsewhere herein.

TABLE 1

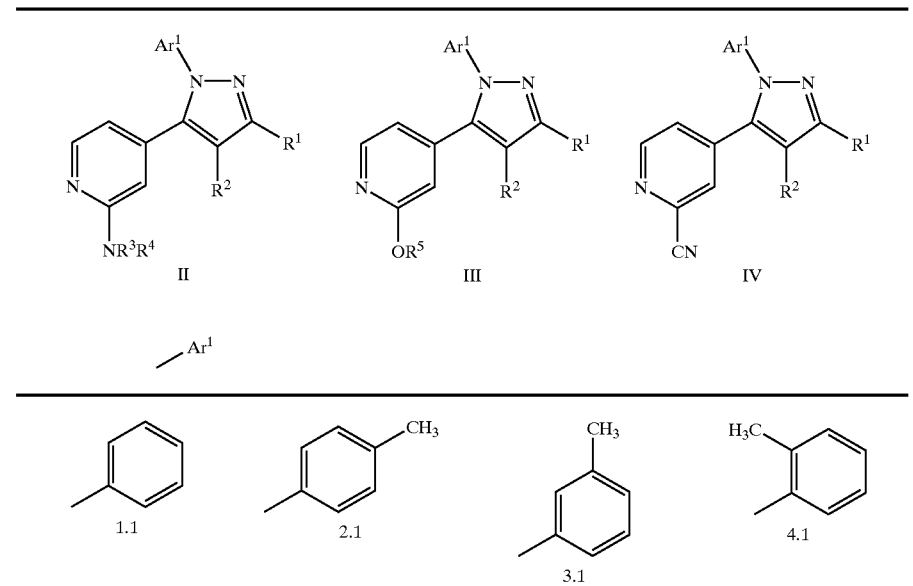

TABLE 1-continued
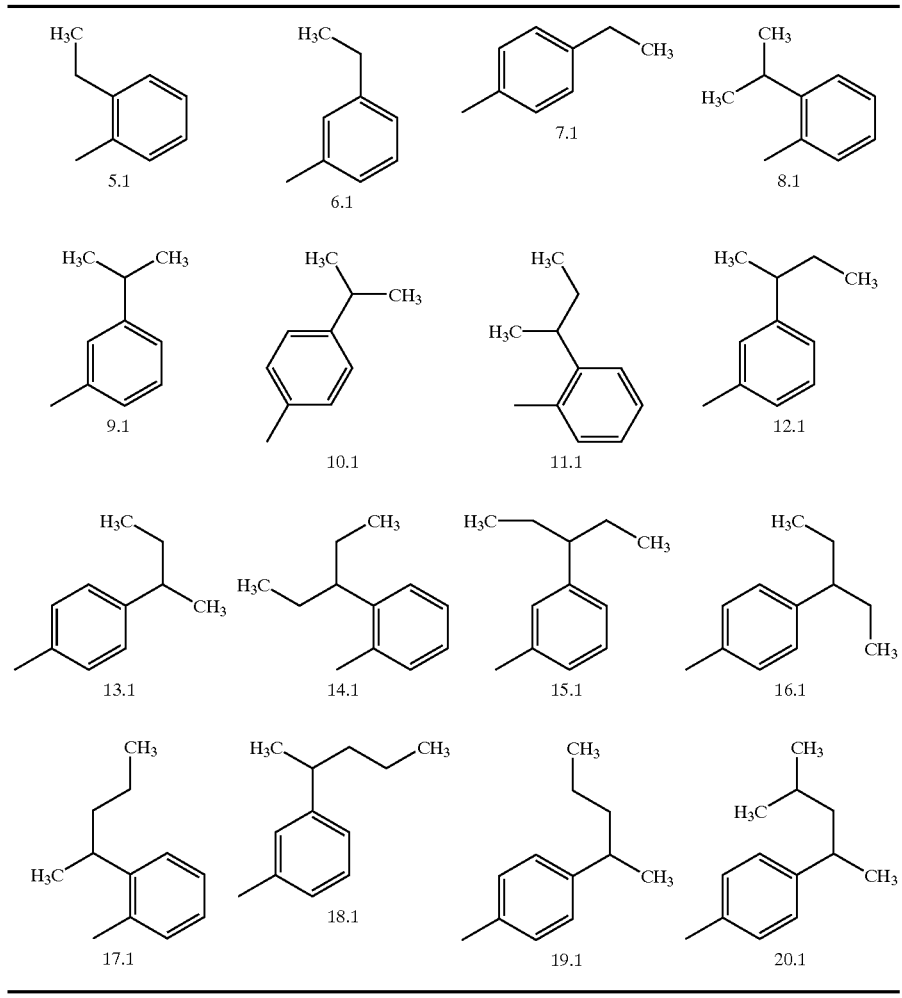
TABLE 2
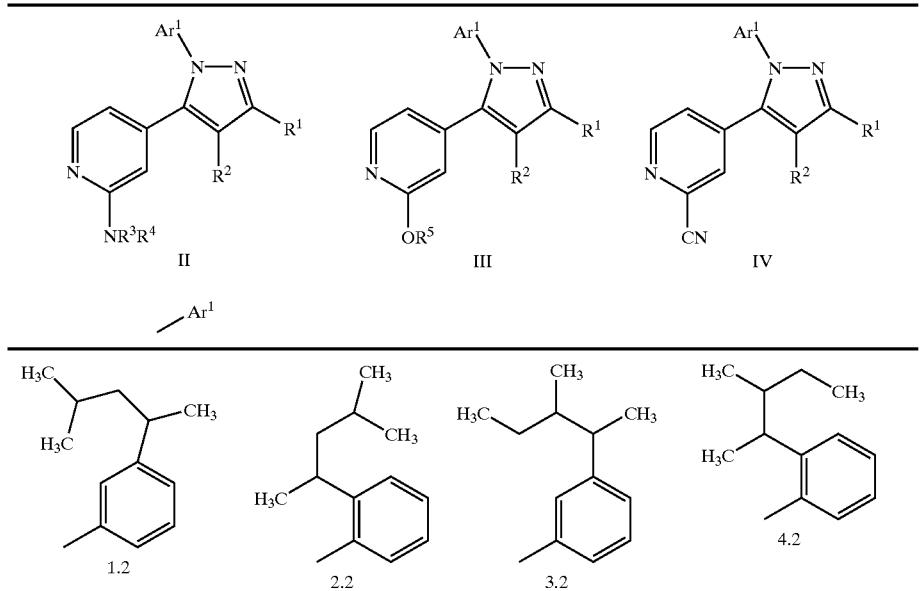

TABLE 2-continued
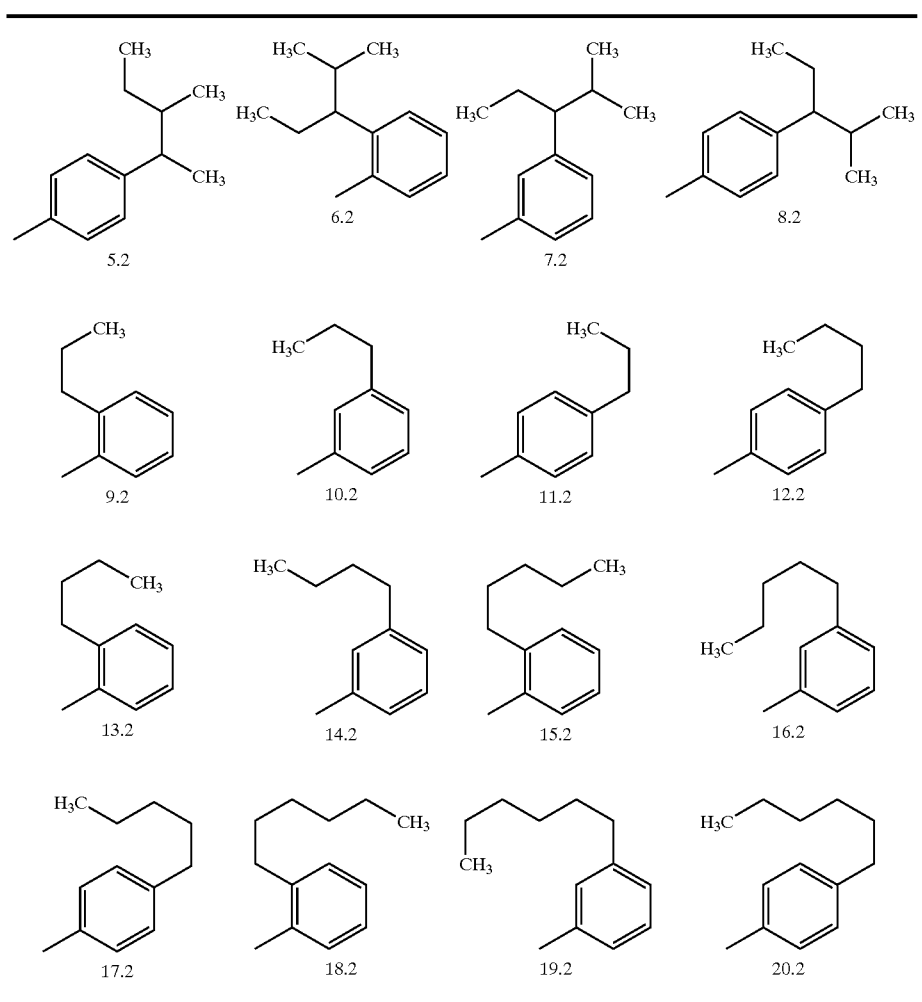
TABLE 3
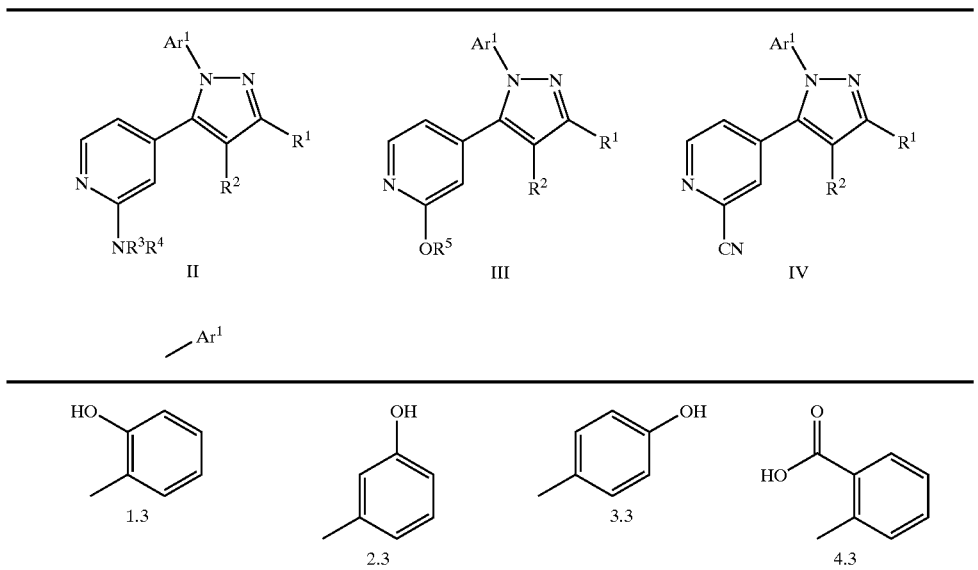

TABLE 3-continued
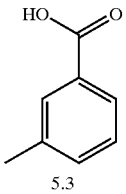 5.3  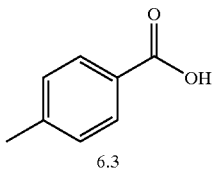 6.3  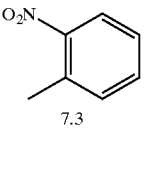 7.3  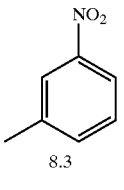 8.3
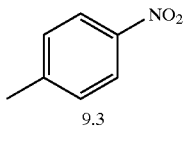 9.3  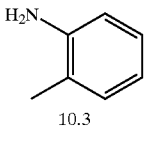 10.3  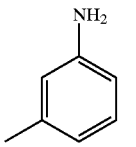 11.3  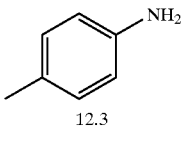 12.3
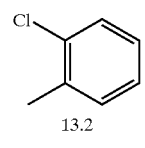 13.2  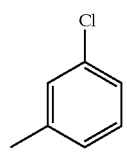 14.3  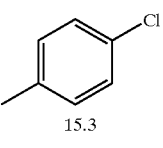 15.3  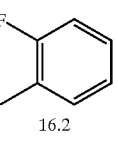 16.2
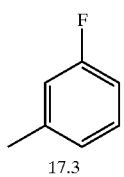 17.3  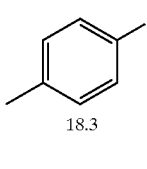 18.3  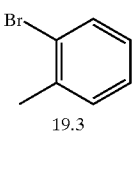 19.3  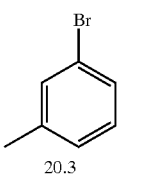 20.3  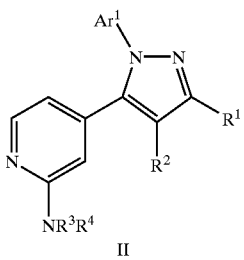 21.3
TABLE 4
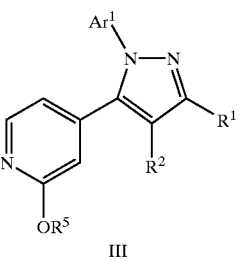
II
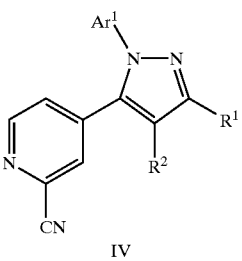
III
IV
$R^1$
 1.4  CH₃  2.4  3.4  4.4
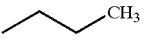 5.4  6.4  7.4  8.4
 9.4  10.4  11.4  12.4

TABLE 4-continued
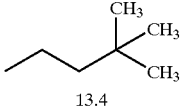
TABLE 5
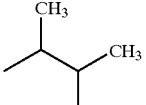

TABLE 5-continued
| | | | |
|---|---|---|---|
| 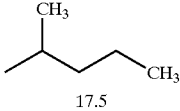 17.5 | 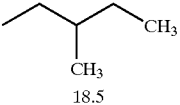 18.5 | 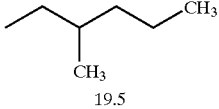 19.5 | 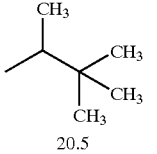 20.5 |
| 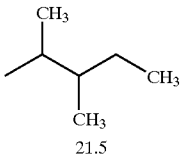 21.5 | 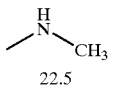 22.5 | 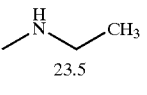 23.5 | 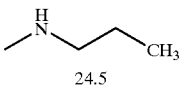 24.5 |
TABLE 6
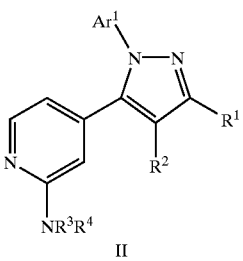
II
| —R³ |
|---|
| | | | |
|---|---|---|---|
|  1.6 |  2.6 |  3.6 | 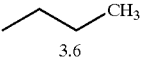 4.6 |
| 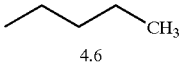 5.6 | 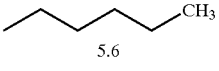 6.6 | 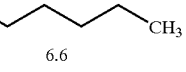 7.6 | 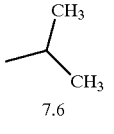 8.6 |
| 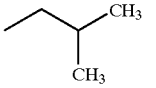 9.6 | 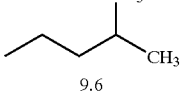 10.6 | 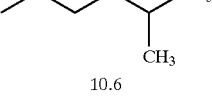 11.6 | 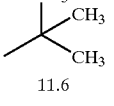 12.6 |
| 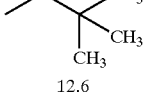 13.6 | 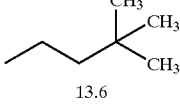 14.6 | 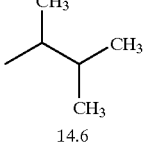 15.6 | 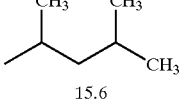 16.6 |
| 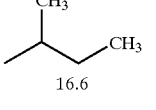 17.6 | 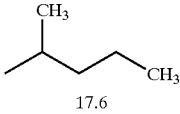 18.6 | 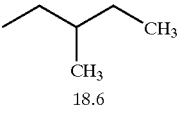 19.6 | 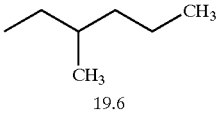 20.6 |

TABLE 6-continued

| |
|---|
| (3-methylpentan-2-yl group structure) 21.6 |

TABLE 7

(Structure II: pyridine ring with NR³R⁴ substituent connected to a pyrrole ring bearing Ar¹, R¹, and R²)

II

/R⁴

| /CH₃ 1.7 | ⁀CH₃ 2.7 | ⁀⁀CH₃ 3.7 | ⁀⁀⁀CH₃ 4.7 |
|---|---|---|---|
| ⁀⁀⁀⁀CH₃ 5.7 | ⁀⁀⁀⁀⁀CH₃ 6.7 | isobutyl 7.7 | isopentyl 8.7 |
| 2-methylpentyl 9.7 | 5-methylhexyl 10.7 | neopentyl 11.7 | 3,3-dimethylbutyl 12.7 |
| 3,3-dimethylpentyl 13.7 | 2,4-dimethylpentyl 15.7 | 2,3-dimethylbutyl 14.7 | 3-methylbutyl 16.7 |
| 4-methylpentyl 17.7 | 3-methylpentyl 18.7 | 4-methylhexyl 19.7 | 2,3,3-trimethylpentyl 20.7 |
| 2-methyl-3-methylpentyl 21.7 | phenylethyl 22.7 | phenylpropyl 23.7 | phenylbutyl 25.7 |

TABLE 8
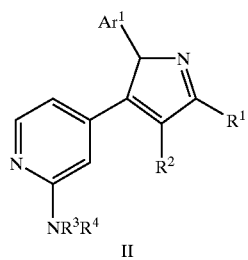
II
| 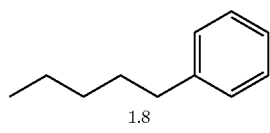 | 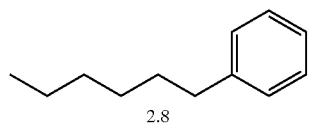 | 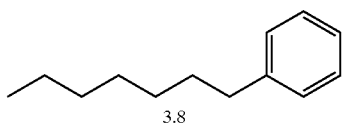 |
| --- | --- | --- |
| 1.8 | 2.8 | 3.8 |
| 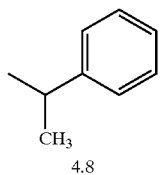 | 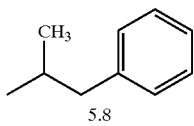 | 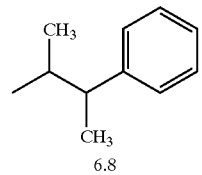 |
| 4.8 | 5.8 | 6.8 |
| 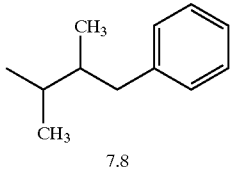 | 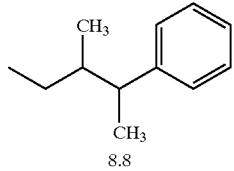 | 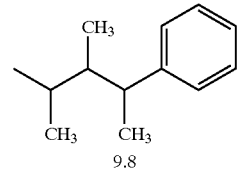 |
| 7.8 | 8.8 | 9.8 |
|  | 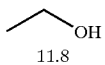 | 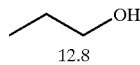 |
| 10.8 | 11.8 | 12.8 |
| 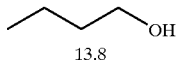 | 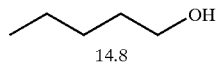 | 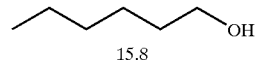 |
| 13.8 | 14.8 | 15.8 |
| 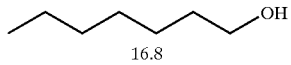 | 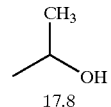 | 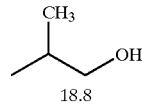 |
| 16.8 | 17.8 | 18.8 |
| 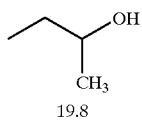 | 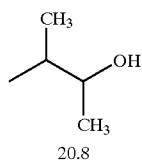 | |
| 19.8 | 20.8 | |

TABLE 9
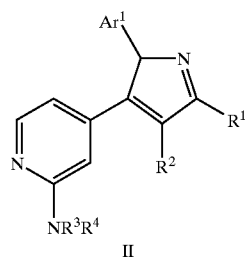
| —R⁴ | | | |
|---|---|---|---|
| OH-CH(CH₃)-CH₃ 1.9 | OH-CH(CH₃)-CH(CH₃)₂ 2.9 | OH-CH(CH₃)-CH(CH₃)-C₂H₅ 3.9 | OH-CH(CH₃)-CH(CH₃)-C₃H₇ 4.9 |
| 5.9 | 6.9 | 7.9 | 8.9 |
| 9.9 | 10.9 | 11.9 | 12.9 |
| 13.9 | 14.9 | 15.9 | 16.9 |
| 17.9 | 18.9 | 19.9 | 20.9 |

TABLE 10
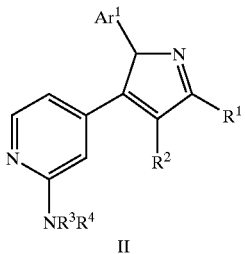
II
—R⁴
| | | |
|---|---|---|
|  1.10 | 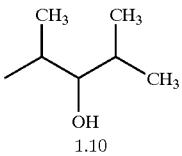 2.10 | 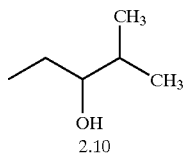 3.10 |
| 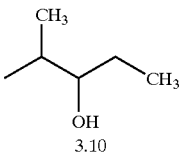 4.10 | 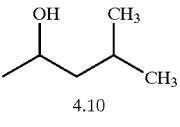 5.10 | 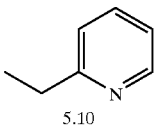 6.10 |
| 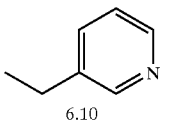 7.10 | 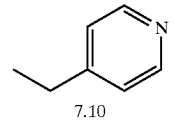 8.10 | 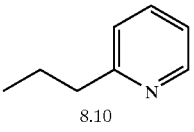 9.10 |
| 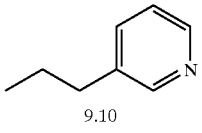 10.10 | 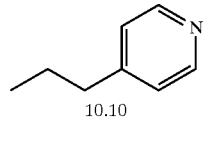 11.10 | 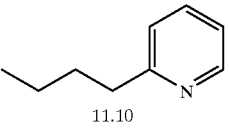 12.10 |
| 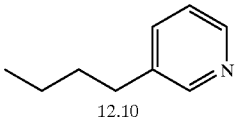 13.10 | 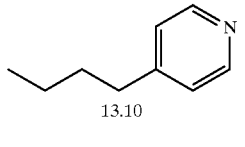 14.10 | 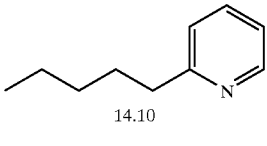 15.10 |
| 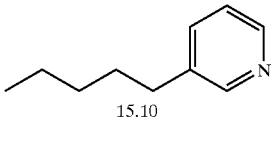 16.10 | 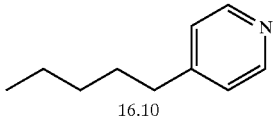 17.10 | 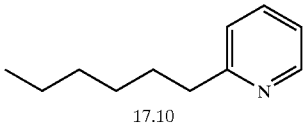 18.10 |
| 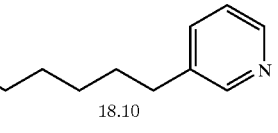 19.10 | | |

TABLE 11
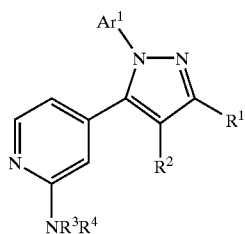
| | —R⁴ |
|---|---|
| 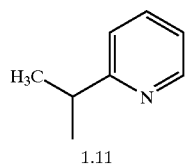 1.11 | 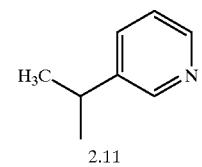 2.11 |
| 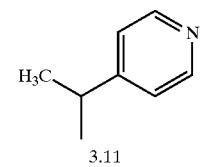 3.11 | 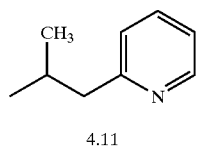 4.11 |
| 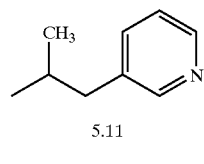 5.11 | 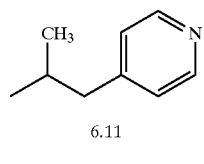 6.11 |
| 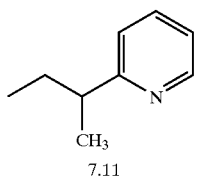 7.11 | 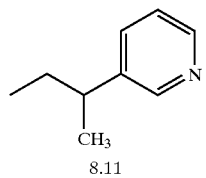 8.11 |
| 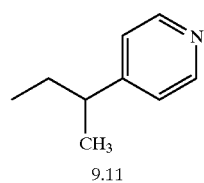 9.11 | 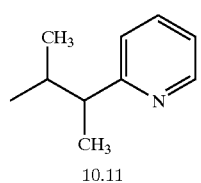 10.11 |
| 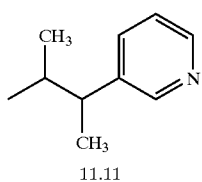 11.11 | 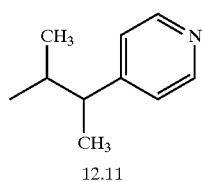 12.11 |
| 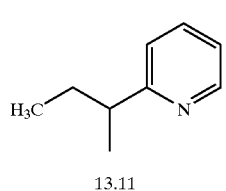 13.11 | 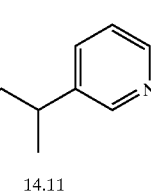 14.11 |
| 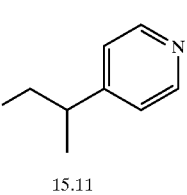 15.11 | 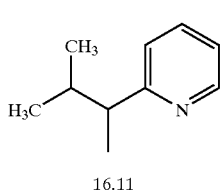 16.11 |
| 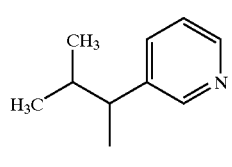 17.11 | 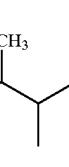 18.11 |
| 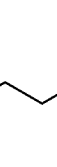 19.11 | 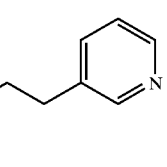 20.11 |

TABLE 12
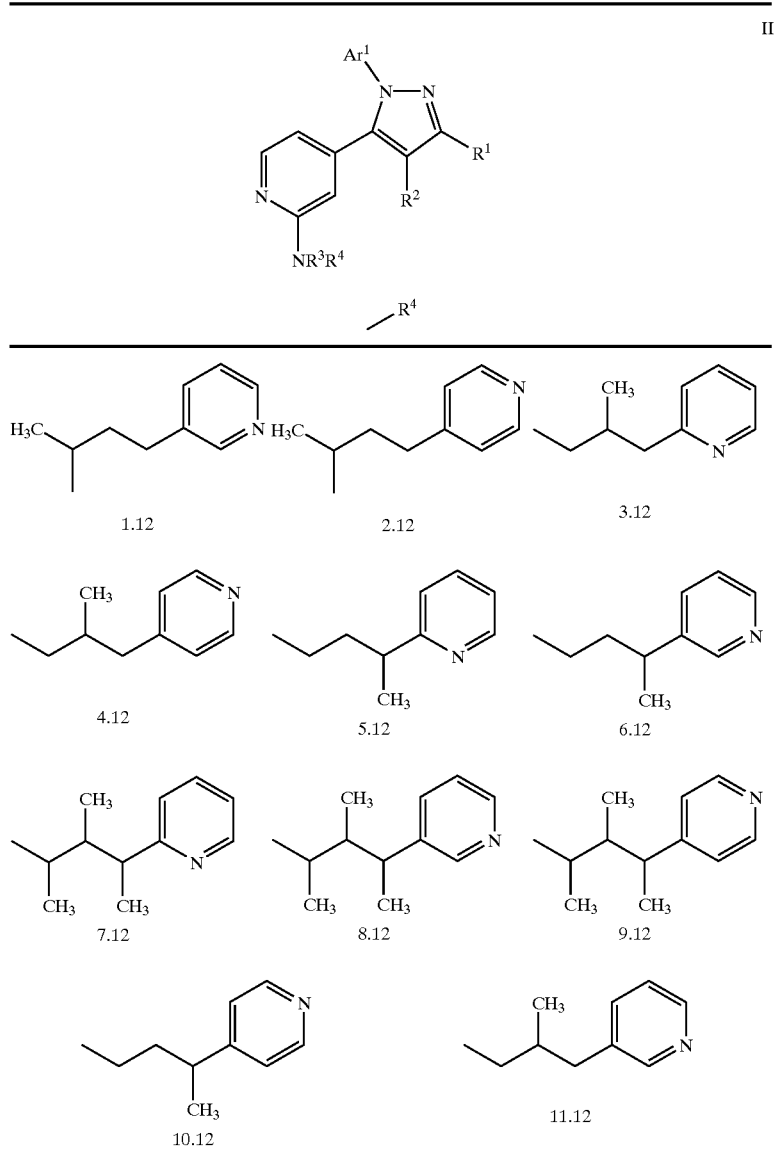
TABLE 13
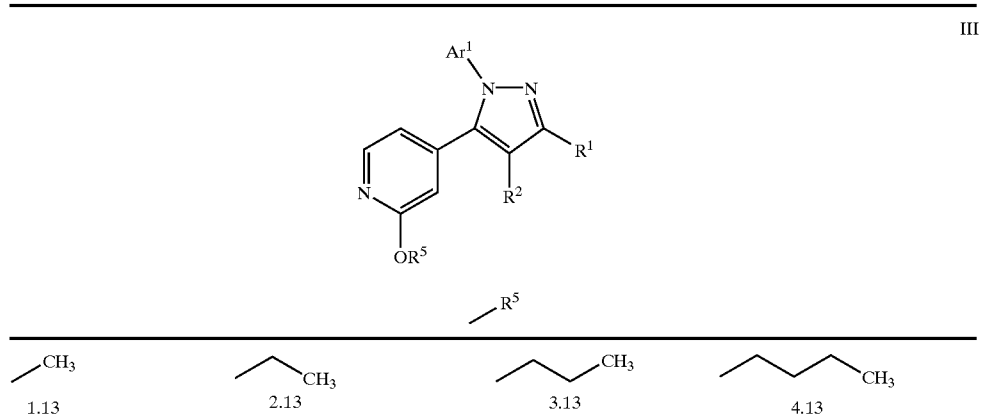

TABLE 13-continued
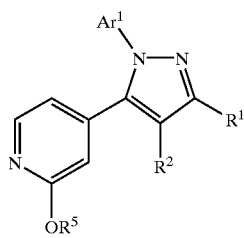
III
/R⁵
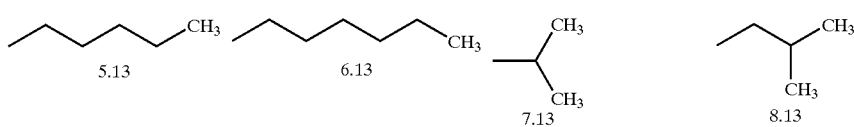
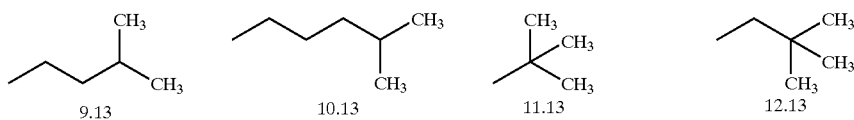
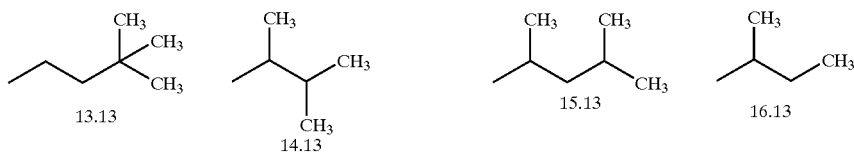
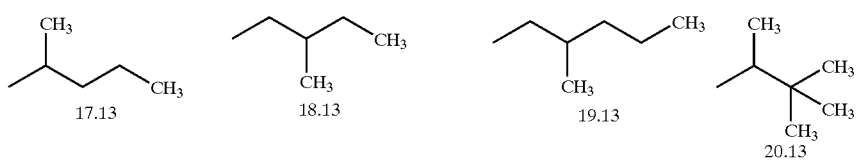
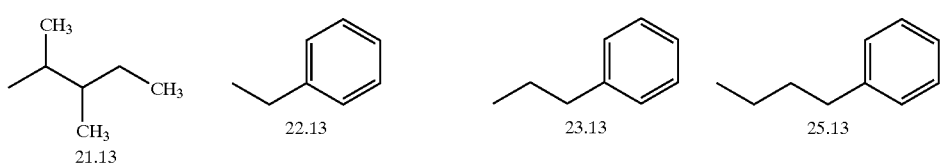

TABLE 14

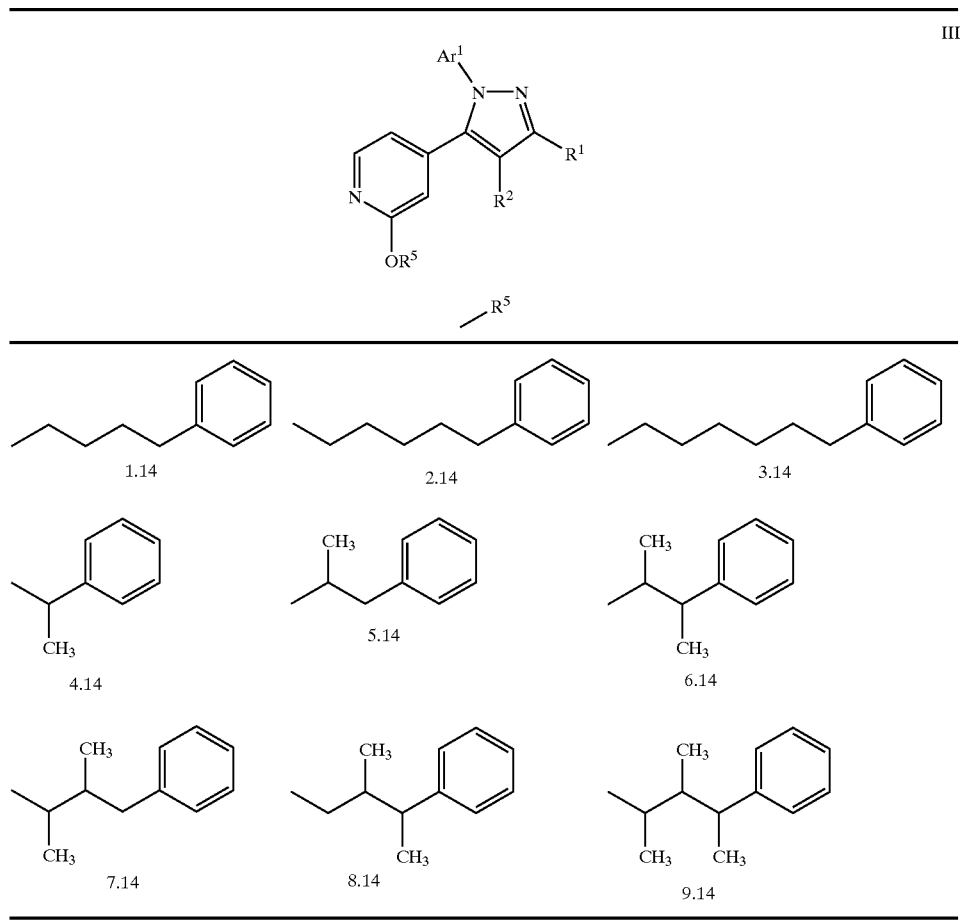

Treatment Process

The present invention also contemplates a process for the treatment of a TNF-mediated disorder or a p38 kinase-mediated disorder, such as arthritis. That process comprises administering a therapeutically-effective amount (a p38 MAP kinase enzyme-inhibiting effective amount) of a compound of Formula I, or a pharmaceutically-acceptable salt thereof, to a mammalian host having such a condition. A mixture of such compounds can also be used. The use of administration repeated a plurality of times is particularly contemplated.

Also included in the family of compounds of Formula I (and also Formulas II, III and IV) are the pharmaceutically-acceptable salts of those compounds, as noted previously. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I can be prepared from an inorganic acid or from an organic acid.

Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, aralphatic, heterocyclyl, carboxylic and sulfonic classes of organic acids. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, hydroxybutyric, galactaric and galacturonic acids.

Suitable pharmaceutically-acceptable base addition salts of compounds of Formula I include metallic ion salts and organic ion salts. More preferred metallic ion salts include, but are not limited to appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by conventional means from the corresponding compound of Formula I by reacting for example, the appropriate acid or base with the compound of Formula I.

A compound of Formula I is preferably administered in a pharmaceutical composition. Such a composition contains a therapeutically-effective amount of a compound of Formula I in association with at least one pharmaceutically-acceptable carrier, adjuvant or diluent.

Thus, also embraced within this invention is a class of pharmaceutical compositions comprising a compound of Formula I as active ingredient (agent or compound) in association with one or more non-toxic, pharmaceutically-acceptable carriers and/or diluents and/or adjuvants (collectively referred to herein as "carrier" materials) and, if desired, other active ingredients.

The active compounds of the present invention can be administered by any suitable route, preferably in the form of a pharmaceutical composition adapted to such a route, and in a dose effective for the treatment intended. The active compounds and composition can, for example, be administered orally, intravascularly (IV), intraperitoneally, subcutaneously, intramuscularly (IM) or topically.

For oral administration, the pharmaceutical composition can be in the form of, for example, a tablet, hard or soft capsule, lozenges, dispensable powders, suspension or liquid. The pharmaceutical composition is preferably made in the form of a dosage unit containing a particular amount of the active ingredient. Examples of such dosage units are tablets or capsules.

The active ingredient can also be administered by injection (IV, IM, subcutaneous or jet) as a composition wherein, for example, saline, dextrose, or water can be used as a suitable carrier. The pH value of the composition can be adjusted, if necessary, with suitable acid, base, or buffer. Suitable bulking, dispersing, wetting or suspending agents, including mannitol and PEG 400, can also be included in the composition. A suitable parenteral composition can also include a compound formulated as a sterile solid substance, including lyophilized powder, in injection vials. Aqueous solution can be added to dissolve the compound prior to injection.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus can vary widely.

A pharmaceutical composition can contain an active compound at about 0.1 to 1000 mg, preferably at about 7.0 to 350 mg. A daily dose of about 0.01 to 100 mg/kg body weight, preferably between about 0.1 and about 50 mg/kg body weight, and most preferably between about 0.5 to 30 mg/kg body weight, can be appropriate. The daily dose can be administered in one to four doses per day.

In the case of skin conditions, it can be preferable to apply a topical preparation of compounds of this invention to the affected area two to four times a day. For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w.

When formulated in an ointment, the active ingredients can be employed with either paraffinic or a water-miscible ointment base. Alternatively, the active ingredients can be formulated in a cream with an oil-in-water cream base. If desired, the aqueous phase of the cream base can include, for example at least 30% w/w of a polyhydric alcohol such as propylene glycol, butane-1,3-diol, mannitol, sorbitol, glycerol, polyethylene glycol and mixtures thereof.

The topical formulation can desirably include a compound that enhances absorption or penetration of the active ingredient through the skin or other affected areas. Examples of such dermal penetration enhancers include dimethylsulfoxide and related analogs.

The compounds of this invention can also be administered by a transdermal device. Preferably, topical administration is accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent can also function as the membrane. The transdermal patch can include the compound in a suitable solvent system with an adhesive system, such as an acrylic emulsion, and a polyester patch.

The oily phase of the emulsions of this invention can be constituted from known ingredients in a known manner. Although the phase can comprise merely an emulsifier, it can comprise a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween™ 60, Span™ 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters can be used. These can be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w.

For therapeutic purposes, the active compounds of this combination invention are ordinarily combined with one or more adjuvants appropriate to the indicated route of administration. If administered per os, the compounds can be admixed with lactose, sucrose, starch-powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose.

Formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Preparation of Useful Compounds

Schemes I through IX hereinbelow illustrate chemical processes and transformations that can be useful for the preparation of compounds useful in this invention; i.e., compounds of Formulas I, wherein $R^1$, and $R^2$, substituent and $Ar^1$, are as defined for Formula I, except where noted.

Scheme I

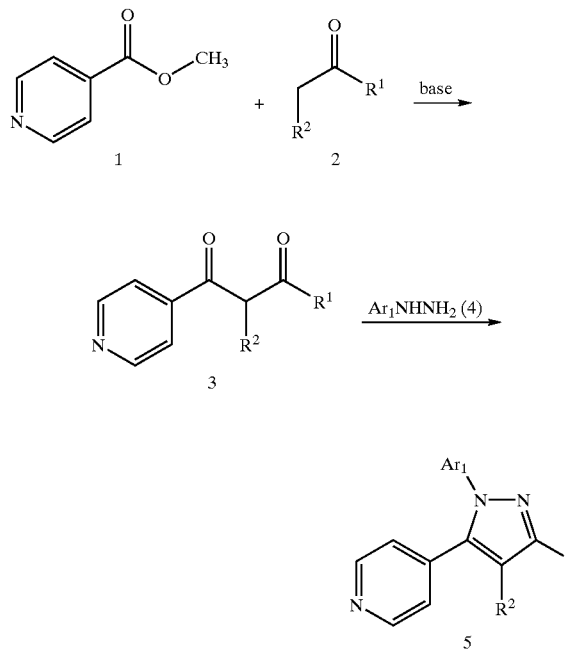

Scheme I shows the synthesis of a 1,5-diaryl pyrazole (5) wherein a pyridine ring is attached to position 5 of the pyrazole ring, $R^1$ is lower alkyl and $R^2$ is hydrido or lower alkyl. The synthesis is carried out by condensing an appropriate ketone (2) with methyl isonicotinate (1) in the presence of a suitable base to provide the diketone 3. Examples of appropriate ketones include acetone, methyl ethyl ketone, diethyl ketone and the like. Examples of suitable bases include sodium methoxide, and sodium ethoxide and the like. Suitable solvents for this reaction include tetrahydrofuran (THF) or methanol (MeOH) at temperatures ranging from room temperature to reflux. Treatment of diketone 3 with an aryl hydrazine derivative 4, in a suitable solvent at temperatures ranging up to reflux provides a 1,5-diaryl pyrazole, compound 5. Examples of suitable solvents for this reaction include ethanol, acetic acid, ethanol-acetic acid mixtures and the like. Substitution on $Ar_1$ in 5 is controlled by proper selection of the starting hydrazine 4. When $R^2$ of ketone 2 is hydrido, then $R^2$ of pyrazole 5 is hydrido.

Scheme II

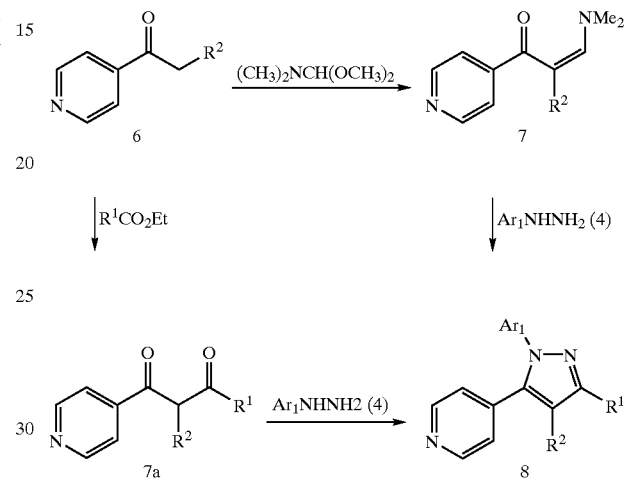

Scheme II illustrates the synthesis of a pyrazole, compound 8 wherein $R^2$ is a lower alkyl group and $R^1$ is hydrido or lower alkyl. Compounds wherein $R^1$ is hydrido and $R^2$ is a lower alkyl group can be synthesized by treatment of pyridyl ketone 6 with dimethylformamide dimethyl acetal (DMF acetal). Examples of suitable pyridyl ketones 6 include propionyl pyridine and butanoyl pyridine. This reaction can be carried out in the DMF acetal itself or in a suitable solvent such as dimethylformamide. This provides enamine 7 which is convertible to pyridyl pyrazole 8 by reaction with a suitably substituted phenylhydrazine. This step can be carried out as described for Scheme I and substitution on $Ar_1$ of pyrazole 8 is controlled by selection of a properly substituted hydrazine. Scheme II also describes the synthesis of pyrazoles wherein both $R^1$ and $R_2$ are lower alkyl groups. This is achieved by reacting ketone 6 with a carboxylic acid ester, such as methyl acetate or methyl propionate or the like, in the presence of a base, such as sodium methoxide, in a suitable solvent, such as methanol or tetrahydrofuran. The resulting diketone 7a is converted to pyrazole 8 ($R^1$ and $R^2$ are lower alkyl) using the procedure described above.

Scheme III

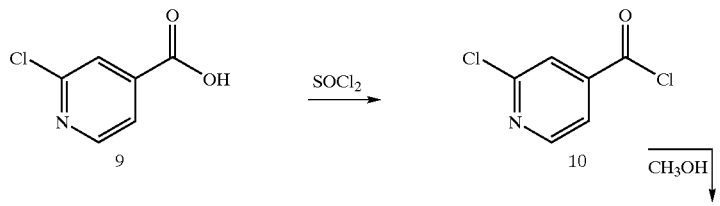

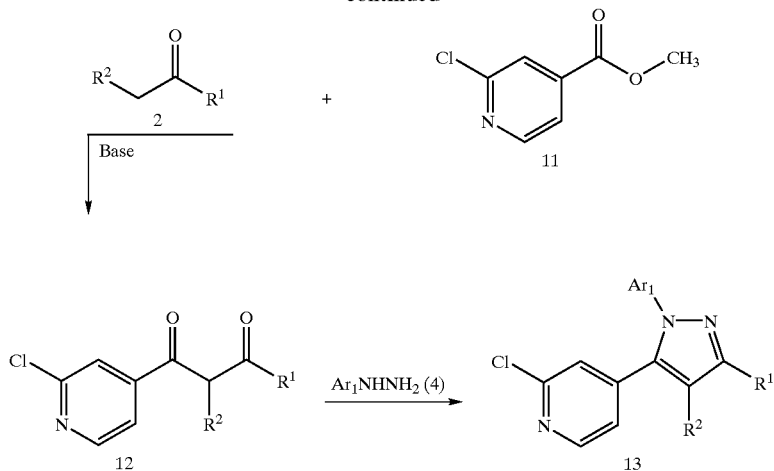

Scheme III shows the synthesis of a pyrazole, compound 13, analogs of compound 5 in which the pyridine 10 ring bears a chlorine atom at position 2. 2-Chloropyridine-4-carboxylic acid, compound 9, is treated with thionyl chloride in a solvent such as toluene, and heated to reflux to give 2-chloropyridine-4-carboxylic acid chloride, compound 10, which is then converted to methyl 2-chloroisonicotinate, compound 11. Compound 11 is treated with a ketone 2 in the presence of a base such as sodium methoxide in a solvent such as tetrahydrofuran, at temperatures ranging from 25° C. up to reflux to provide a diketone, compound 12. Treatment of the diketone, compound 12, with an arylhydrazine derivative 4 in ethanol or other suitable solvent at a temperature ranging up to reflux, provides pyrazole compound 13. When $R^2$ of ketone 2 is hydrido, then $R^2$ of 13 is hydrido.

Scheme IV

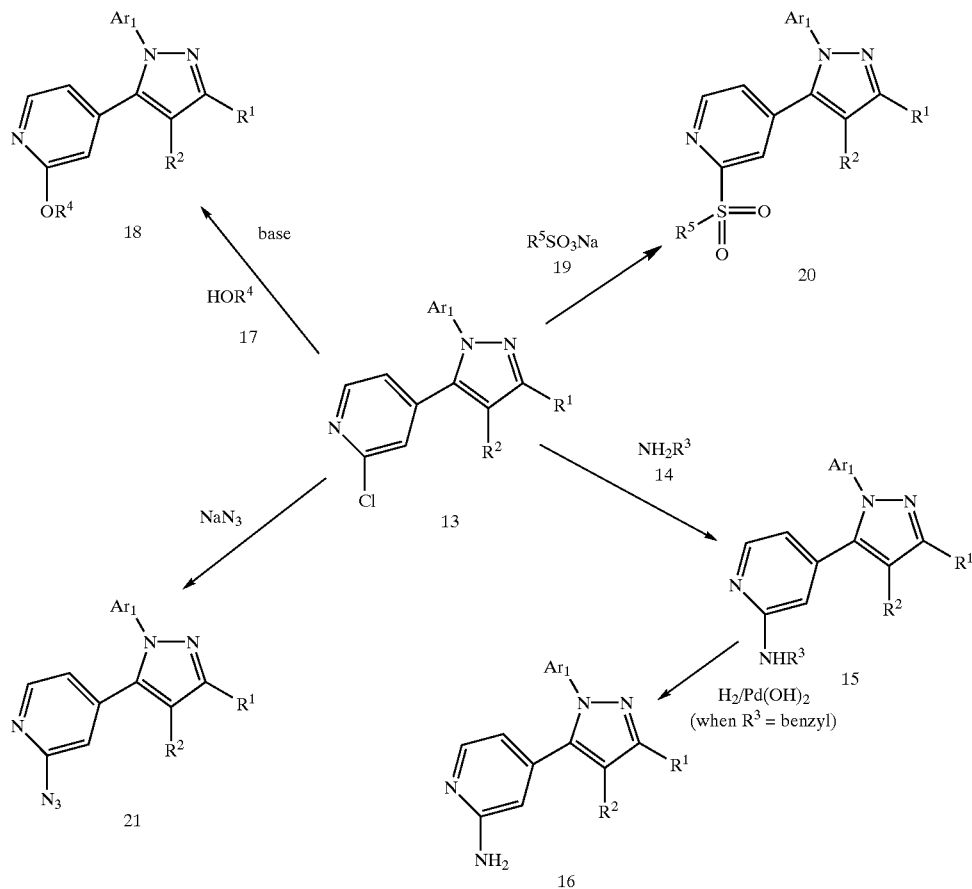

Scheme IV shows the syntheses of various pyrazole derivatives from compound 13 by manipulations on its 2-chloropyridine ring. The chlorine atom is a labile group and can be displaced with various nucleophiles to provide 2-substituted pyridine derivatives. When compound 13 is treated with an amine 14 at a temperature of usually about 100 to about 200° C. and at a pressure of about 70 to about 200 (or higher) psi in xylene, pyrazole 15 is formed. Examplary substituents for $R^3$ of amine 14 are hydrogen, lower alkyl, hydroxyalkyl, or aralkyl.

When $R^3$ is benzyl, hydrogenation of the compound removes the benzyl group and forms the amino compound 16. When the benzyl group bears a para methoxy substituent, an alternative method of removal of the benzyl group is treatment with refluxing trifluoroacetic acid.

Treatment of compound 13 with an alcohol 17 in the presence of a base in a suitable solvent provides pyrazole compound 18. Examples of suitable alcohols are benzyl alcohol and methanol. Suitable bases include triethylamine and pyridine.

Compound 13 can also be treated with a sulfinic acid sodium salt derivative, compound 19, in a suitable solvent such as dimethylformamide (DMF) at an elevated temperature to provide pyrazole compound 20. An example of a sulfinic acid sodium salt is sodium methane sulfinate and its reaction leads to methyl sulfone.

Finally, treatment of compound 13 with sodium azide in a suitable solvent such as DMF, provides azido pyridine 21.

Scheme V

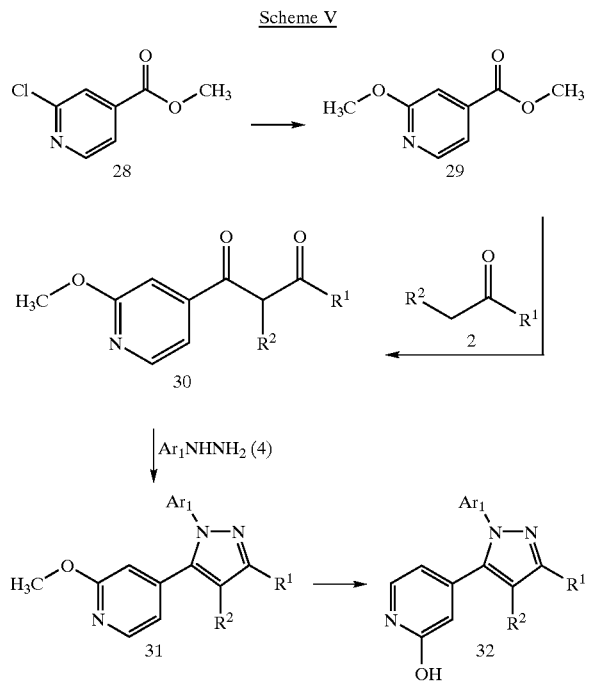

Scheme V shows the preparation of pyrazole compounds 31 and 32 bearing hydroxy and methoxy substituents at position 2 of the pyridine ring. Treatment of methyl 2-methoxyisonicotinate compound 29, which is derived from methyl 2-chloroisonicotinate, compound 28, with a ketone, compound 2, provides compound 30, a diketone. Compound 30 is treated with an arylhydrazine derivative, compound 4, under the standard condition as described in the previous synthetic schemes, to yield pyrazole 31. Treatment of compound 31 with an acid such as hydrochloric acid provides pyrazole 32 which bears a hydroxyl at position 2 of the pyridine ring. When $R^2$ of ketone 2 is hydrogen (hydrido), then $R^2$ of pyrazoles 31 and 32 is hydrogen (hydrido).

Scheme VI

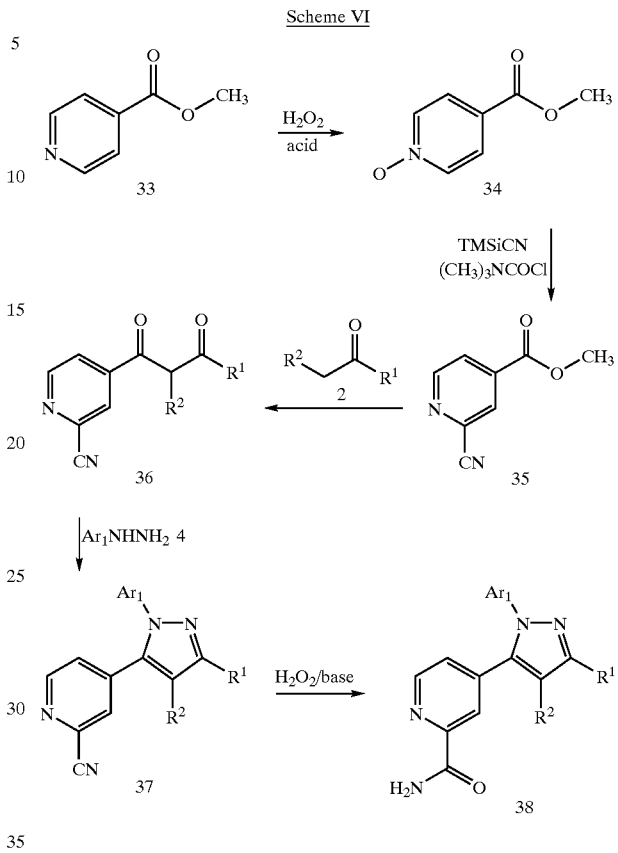

Scheme VI demonstrates the syntheses of the pyrazole compounds 37 and 38 that bear cyano and carboxamido substituents, respectively, at position 2 of the pyridine ring. Methyl 2-cyanoisonicotinate 35 is synthesized from methyl isonicotinate 33 in two steps by oxidation with hydrogen peroxide in an acid solvent, such as acetic acid. The resulting pyridine N-oxide 34 is treated with dimethylcarbamoyl chloride in the presence of trimethylsilylcyanide to provide ester 35. Treatment of ester 35 with ketone 2 according to general conditions described for similar reactions in the preceding schemes gives diketone 36. Treatment of 36 with a substituted arylhydrazine produces pyrazole 37. Desired substitution on $Ar_1$ is achieved by selection of the properly substituted arylhydrazine.

Cyano pyrazole 37 is converted to the carboxamido compound 38 by oxidation with hydrogen peroxide in the presence of a base. Suitable bases include sodium carbonate, potassium carbonate and sodium hydroxide. Manipulation of substituent $R^2$ is effected by selection of the proper ketone 2. When $R_2$ of compound 2 is hydrogen, $R^2$ in pyrazoles 37 and 38 is hydrogen (hydrido).

Scheme VII

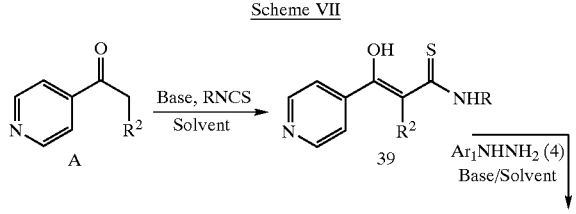

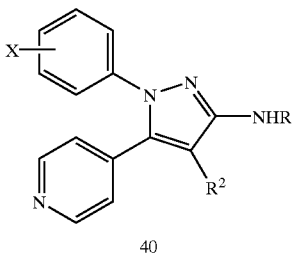

Scheme VII illustrates a two-step synthesis of 3-amino-1,5-diarylpyrazoles 40. In the first step, 4-acetylpyridine (A, R²=H) is treated with a suitable base to generate an enolate anion. Examples of suitable bases include lithium hexamethyl disilazide, sodium hexamethyldisilazide and lithium diisopropylamide. Suitable solvents for this reaction include tetrahydrofuran and diethyl ether. The resulting intermediate enolate anion is treated with a suitable isothiocyanate to give beta keto thioamide 39. Examples of suitable isothiocyanates include ethyl isothiocyanate and trimethylsilylisothicyanate. The reaction of thioamide 39 with an arylhydrazine 4 leads to the formation of pyrazole 40. This reaction is carried out using conditions discussed in preceding examples. Control of substitution on $Ar_1$ is effected by proper selection of the substituted phenylhydrazine.

When an alkyl isothiocyanate is employed in this sequence, R of compound 40 is an alkyl group. When trimethylsilyl isothiocyanate is employed, R of 40 is a trimethylsilyl group, which is easily removed to produce the primary amino compound where R of compound 40 is hydrogen. Examples of reaction conditions used to remove the silyl group are acetic acid in water and tetrahydrofuran or aqueous sodium bisulfate. When $R^2$ of the starting pyridyl ketone is a substituent other than H, that substituent becomes the substituent $R^2$ at the 4 position of the pyrazole 40.

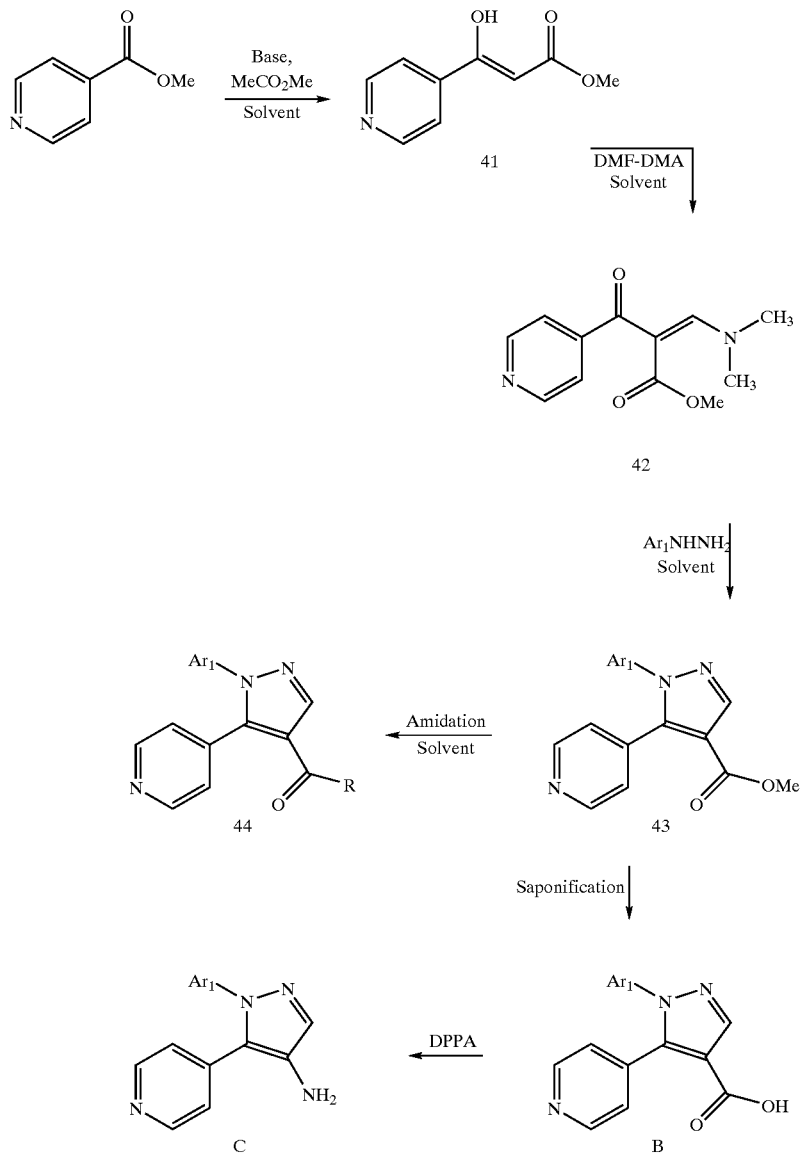

Scheme VIII illustrates the synthesis of a 1,5-diaryl pyrazole wherein $R^2$ is a derivatized carboxyl group or an amino group. An ester of isonicotinic acid is treated with a carboxylic acid ester in the presence of a base to produce beta keto ester 41. Suitable esters of isonicotinic acid include the methyl and ethyl esters and the like. Suitable esters of the carboxylic acid also include the methyl and ethyl esters. Bases such as sodium methoxide and sodium ethoxide are suitable for this reaction. The reaction can be carried out in an alcoholic solvent such as methanol or ethanol. Ketoester 41 is converted to the enamine intermediate 42 by reaction with dimethylformamide dimethylacetal either neat or in a solvent such as dimethyl formamide. Reaction with a properly substituted arylhydrazine 4 produces the carboxylic acid ester 43. Reaction of this ester with various amines, such as piperazine produces amides 44 (R=substituted amine).

Similarly, saponification of 43 produces acid B. Saponification can be carried out using a base such as sodium hydroxide in an aqueous solvent such as aqueous methanol or ethanol or the like. Acid B is converted to amine C by reaction with diphenylphosporyl azide (DPPA) in the presence of a base such as triethylamine in a solvent such as tetrahydrofuran or dioxane.

Scheme IX

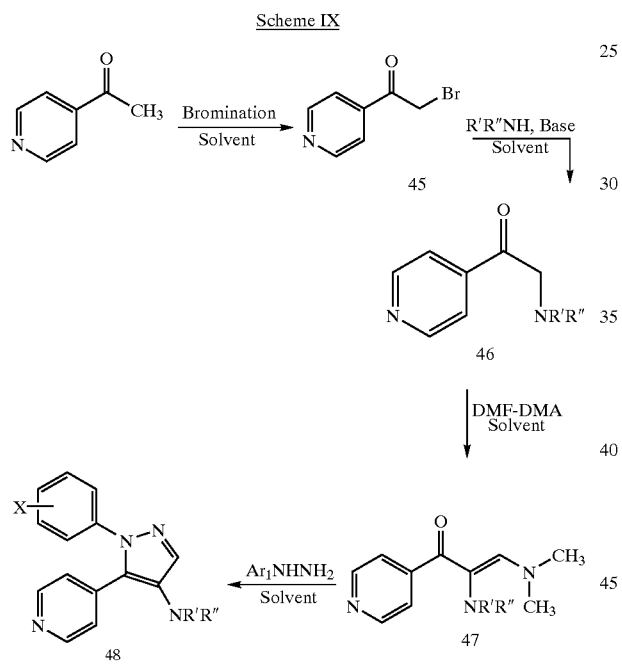

Scheme IX illustrates the synthesis of a 4-amino-1,5-diarylpyraozle, compound 48. In step 1, 4-acetylpyridine is brominated with bromine in the presence of a solvent such as 48 percent hydrobromic acid to provide the bromoketone, compound 45. In step 2, the reaction of compound 45 with an amine, such N-tert-butoxycarbonylpiperazine, in the presence of a base such as triethylamine, and in the presence of a solvent such as DMF, provides intermediate compound 46. Other suitable amines include piperidine and dimethylamine. In step 3, the reaction of intermediate compound 46 with dimethylformamide dimethylacetal (DMF-DMA) in a solvent such as tetrahydrofuran or dimethyformamide provides intermediate enamine 47. In step 4, the condensation of intermediate compound 47 with a substituted arylhydrazine such as 4-fluorophenylhydrazine, in a solvent such as ethanol provides desired pyrazole, compound 48.

It should be recognized that in the above Schemes, the pyridine ring can be replaced by a pyrimidine ring when suitably substituted pyrimidine starting materials are employed. Suitable starting materials are recognizable by one skilled in the art and their syntheses are readily accessible in the scientific literature. For example, the ethyl ester of pyrimidine-4-carboxylic acid can be synthesized according to procedures described by Wong et al, J. Org. Chem., vol. 30, p. 2398 (1965). The methyl ester of 2-methoxypyrimidine-4-carboxylic acid is described by Warczykowski and Wojciechowski, Pol. J. Chem., vol. 54, pp. 335–340 (1980). The synthesis of 2-diethylaminopyrimidine-4-carboxylic acid from 2-chloropyrimidine-4-carbonitrile is also described in that paper. The synthesis of 2-aminopyrimidine-4-carboxylic acid from 2-chloropyrimidine-4-carbonitrile is described by Daves et al., in J. Het. Chem., vol. 1, p. 130 (1964). The synthesis of 2-chloropyrimidine-4-carbonitrile is described by D. J. Brown et al, Aust. J. Chem., vol. 37, pp. 155–163 (1984) and by A. E. Friesen et al., Tetrahedron, vol. 45, pp. 5151–5162 (1989). The conversion of 2-methylpyrimidine-4-carboxylic acid methyl ester to a 1,3-diketone by reaction with the enolate anion of acetophenone is described by T. Sakamoto, Chem. Pharm. Bull., vol. 30, pp. 1033–1035 (1982).

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

Preparation of

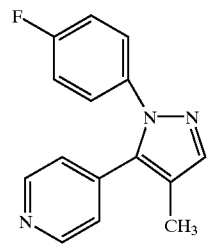

Step 1: Preparation of 1-(4-Pyridinyl)-2-methyl-1,3-propanedione

A mixture of 4-propionylpyridine (5 g, 36.99 mmol) and dimethylformamide dimethylacetal(10 mL, 75.28 mmol) was heated to reflux overnight. After cooling to room temperature, methanol generated in situ was removed from reaction mixture under reduced pressure, providing a brown color solid. The crude product was purified by column chromatography (silica gel, 3:7 EtOAc/haxane) to give the named compound (5.73 g, 81%) as a brown oil.

Step 2:

A mixture of 1-(4-pyridinyl)-2-methyl-1,3-propanedione (0.5 g, 2.63 mmol), 4-fluorophenylhydrazine·HCl (0.514 g, 3.16 mmol), and 15 M ammonium hydroxide (0.211 mL, 3.16 mmol) in ethanol (7 mL) was heated to reflux overnight. The resulting dark solution was cooled to room temperature and extracted with ethyl acetate. The organic layer was washed with saturated sodium bicarbonate and brine, dried over magnesium sulfate. After filtration, the solution was concentrated to give a yellow oil. The oil was purified by column chromatography (silica gel, 3:7 EtOAc/ hexane) to yield the titled compound (0.368 g, 58%) as a light yellow solid. MP: 135.86° C.; Anal. Calc'd for C$_{15}$H$_{12}$N$_3$F.0.1H$_2$O: C, 70.63, H, 4.82, N, 16.47; Found: C, 70.45, H, 4.51, N, 16.42.

EXAMPLE 2

Preparation of

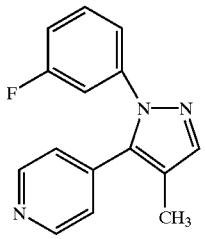

By following the method of Example 1 and substituting of 3-fluorophenylhydrazine·HCl for 4-fluorophenylhydrazine·HCl in step 2, the titled product was obtained: MP: 131.11° C. Anal. Calc'd for C$_{15}$H$_{12}$N$_3$F.0.1H$_2$O: C, 70.63, H, 4.82, N, 16.47. Found: C, 70.64, H, 4.97, N, 16.09.

EXAMPLE 3

Preparation of

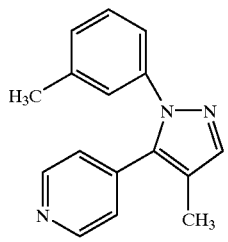

By following the method of Example 1 and substituting of 3-methylphenylhydrazine·HCl for 4-fluorophenylhydrazine·HCl in step 2, the titled product was obtained: MP: 141.77° C. Anal. Calc'd for C$_{16}$H$_{15}$N$_3$.0.05H$_2$O: C, 76.80, H, 6.08, N, 16.79. Found: C, 76.84, H, 6.27, N, 16.43.

EXAMPLE 4

Preparation of

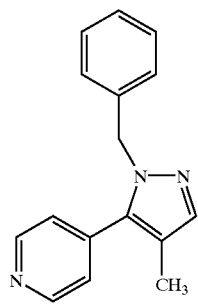

By following the method of Example 1 and substituting of benzylhydrazine·HCl for 4-fluorophenylhydrazine·HCl in step 2, the titled product was obtained: Anal. Calc'd for C$_{16}$H$_{15}$N$_3$: C, 77.08, H, 6.06, N, 16.85. Found: C, 77.03, H, 6.18, N, 16.72.

EXAMPLE 5

Preparation of

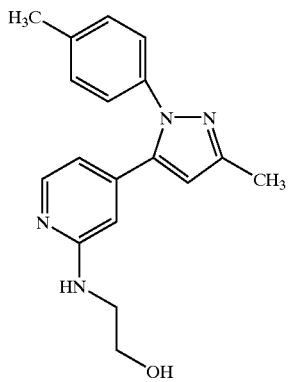

A mixture of 2-chloro-4-[3-methyl-1-(4-methylphenyl)-1H-pyrazol-5-yl]pyridine (Example 41; 0.5 g, 2.53 mmol) and ethanolamine (15 mL, 248.52 mmol) was heated to 105° C. overnight (about eighteen hours). The resulting solution was extracted with ethyl acetate. The organic layer was washed with brine, dried over magnesium sulfate, filtered and concentrated under reduced pressure. The resulting yellow oil crystallized upon standing. The crystals were washed with diethyl ether to yield the titled compound (0.475 g, 61%) as white yellowish crystals. MP: 148.20° C. Anal. Calc'd for C$_{18}$H$_{20}$N$_4$O: C, 70.11, H, 6.54, N, 18.17. Found: C, 69.75, H, 6.71, N, 17.84.

EXAMPLE 6

Preparation of

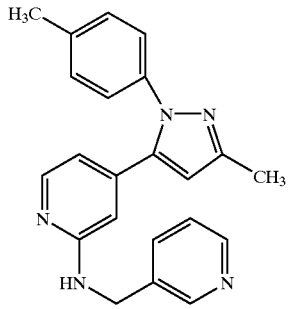

A mixture of 2-chloro-4-[3-methyl-1-(4-methylphenyl)-1H-pyrazol-5-yl]pyridine (Example 41; 0.5 g, 2.53 mmol) and 3-(aminomethyl)pyridine (15 mL, 147.3 mmol) was heated to 180° C. overnight (about eighteen hours). The resulting solution was extracted with ethyl acetate. The organic layer was washed with brine, dried over magnesium sulfate, filtered and concentrated under reduced pressure. The resulting yellow oil was purified by column chromatography (silica gel, EtOAc) to yield the titled compound (0.378 g, 42%) as a white yellowish solid. MP: 108.94° C. Anal. Calc'd for C$_{22}$H$_{21}$N$_5$: C, 73.97, H, 5.98, N, 19.60. Found: C, 73.86, H, 6.25, N, 19.39.

EXAMPLE 7

Preparation of

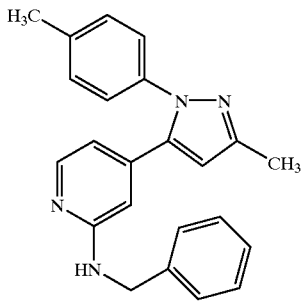

By following the method of Example 5 and substituting of benzylamine for ethanolamine, and changing the reaction temperature from 105° C. to 160° C., the titled compound was obtained: MP: 102.10° C. Anal. Calc'd for $C_{23}H_{22}N_4$: C, 77.94, H, 6.26, N, 15.81. Found: C, 77.82, H, 6.60, N, 15.69.

EXAMPLE 8

Preparation of

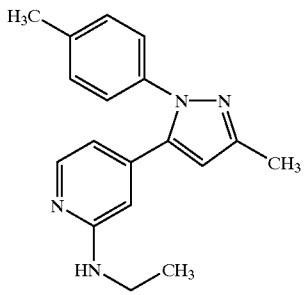

A mixture of 2-chloro-4-[3-methyl-1-(4-methylphenyl)-1H-pyrazol-5-yl]pyridine (Example 41; 0.45 g, 2.3 mmol) and excess aqueous ethylamine (15 mL) was heated to 160° C. at <200 psi in xylene overnight (about eighteen hours). The resulting solution was extracted with ethyl acetate. The organic layer was washed with brine, dried over magnesium sulfate, filtered and concentrated under reduced pressure. The resulting yellow oil was purified by column chromatography [silica gel, ethyl acetate (EtOAc)] to yield (0.372 g, 50%) as a white solid. MP: 97.15° C. Anal. Calc'd for $C_{18}H_{20}N_4$: C, 73.94, H, 6.89, N, 19.16. Found: C, 73.70, H, 6.83, N, 18.98.

EXAMPLE 9

Preparation of

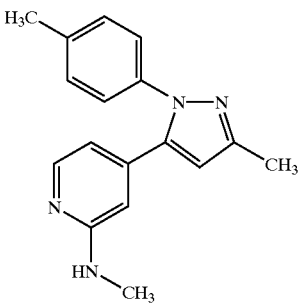

A mixture of 2-chloro-4-[3-methyl-1-(4-methylphenyl)-1H-pyrazol-5-yl]pyridine (Example 41; 0.5 g, 2.53 mmol) and excess methylamine (15 mL) was heated to 170° C. at <200 psi in xylene overnight (about eighteen hours). The resulting solution was extracted with ethyl acetate. The organic layer was washed with brine, dried over magnesium sulfate, filtered and concentrated under reduced pressure. The resulting yellow oil was purified by column chromatography (silica gel, 3:7 EtOAc/hexane) to yield the titled compound 0.218 g, 31%) as a white powder. MP: 126.34° C. Anal. Calc'd for $C_{17}H_{18}N_4$: C, 73.06, H, 6.56, N, 19.81. Found: C, 73.06, H, 6.28, N, 19.43.

EXAMPLE 10

Preparation of

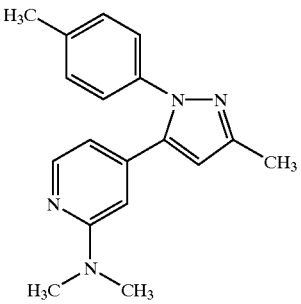

A mixture of 2-chloro-4-[3-methyl-1-(4-methylphenyl)-1H-pyrazol-5-yl]pyridine (Example 41; 0.5 g, 2.53 mmol) and excess dimethylamine (15 mL) was heated to 170° C. at 60–80 psi in xylene overnight (about eighteen hours). The resulting solution was extracted with ethyl acetate. The organic layer was washed with brine, dried over magnesium sulfate, filtered and concentrated under reduced pressure. The resulting yellow oil was purified by column chromatography (silica gel, 3:7 EtOAc/hexane) to yield the titled compound (0.126 g, 17%) as a colorless oil. Anal. Calc'd for $C_{18}H_{20}N_4$: C, 73.94, H, 6.89, N, 19.16. Found: C, 74.04, H, 7.10, N, 19.03.

EXAMPLE 11

Preparation of

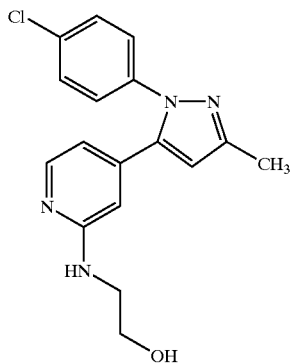

Step 1: Preparation of 2-Chloro-4-[1-(4-chlorophenyl)-3-methyl-1H-pyrazol-5-yl]pyridine A mixture of 1-(2-chloro-4-pyridinyl)-1,3-butanedione (from step 2, Example 29) (2.5 g, 12.69 mmol), p-chlorophenylhydrazine·HCl (2.7 g, 15.11 mmol) and triethylamine (2.1 mL, 15.11 mmol) in ethanol (50 mL) was heated to reflux overnight (about eighteen hours). The resulting dark colored solution was cooled to room temperature and extracted with ethyl acetate. The organic layer was washed with saturated sodium bicarbonate and brine, dried over magnesium sulfate, filtered and concentrated to give 2-chloro-4-[1-(4-chlorophenyl)-3-methyl-1H-pyrazol-5-yl]pyridine as an orange colored solid (1.5 g, 39%). MP: 110.05° C. This product was used in the next step without further purification.

Step 2:

A mixture of 2-chloro-4-[1-(4-chlorophenyl)-3-methyl-1H-pyrazol-5-yl]pyridine (0.6 g, 1.64 mmol) and ethanolamine (15 mL, 248.52 mmol) was heated to 105° C. overnight (about eighteen hours). The solution was extracted with ethyl acetate. The organic layer was washed with brine, dried over magnesium sulfate, filtered and concentrated under reduced pressure. The resulting yellow oil was purified by column chromatography (silica gel, EtOAc) to yield the titled compound (0.253 g, 47%) as a white solid. MP: 137.57° C. Anal. Calc'd. for $C_{17}H_{17}N_4OCl$: C, 62.10, H, 5.21, N, 17.04. Found: C, 62.09, H, 5.24, N, 16.70.

EXAMPLE 12

Preparation of

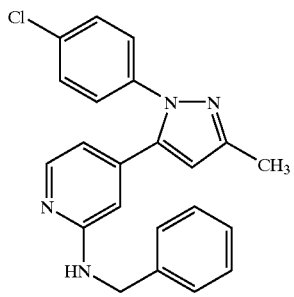

By following the method of Example 11 and substituting of benzylamine for ethanolamine, the titled product was obtained: MP: 105.53° C. Anal. Calc'd for $C_{22}H_{19}N_4Cl$: C, 69.95, H, 5.25, N, 14.44. Found: C, 70.24, H, 5.07, N, 14.19.

EXAMPLE 13

Preparation of

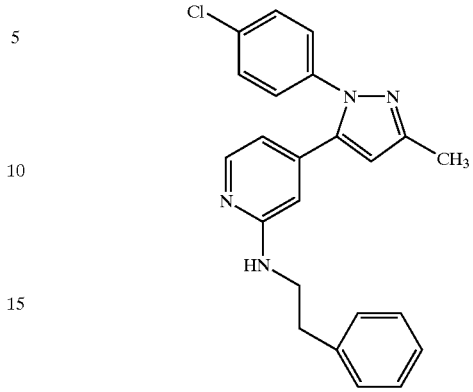

A mixture of the compound from step 1 of Example 11 (1 g, 3.29 mmol) and excess phenylethylamine (15 mL) was heated to 200° C. in xylene overnight (about eighteen hours). The solution was extracted with ethyl acetate. The organic layer was washed with brine, dried over magnesium sulfate, filtered and concentrated under reduced pressure. The resulting yellow oil was purified by column chromatography (silica gel, 1:9 EtOAc/hexane) to yield the titled compound (0.537 g, 42%) as a brown oil. Anal. Calc'd for $C_{23}H_{21}N_4Cl$: C, 71.03, H, 5.44, N, 14.41. Found: C, 70.91, H, 5.43, N, 14.18.

EXAMPLE 14

Preparation of

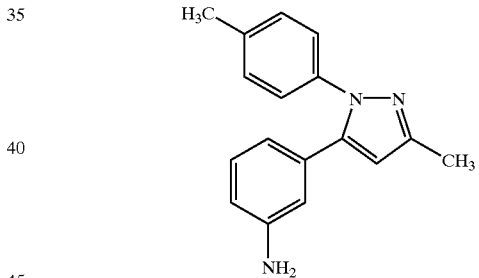

Step 1: Preparation of 1-(3-Aminophenyl)-1,3-butanedione

To a solution of methyl 3-aminobenzoate (7 g, 46.36 mmol) in THF (150 mL) was added acetone (7.5 g, 102 mmol). The solution was warmed to 35° C. where sodium methoxide (3 g, 55.63 mmol) was added sequentially over 20 minutes. The mixture was stirred for 30 minutes, and then brought to reflux for 3 hours. The solvent was removed under reduced pressure and the residue taken up in ethyl acetate. The resulting solution was washed with saturated sodium bicarbonate solution and brine, dried over magnesium sulfate, filtered and concentrated under reduced pressure to give 1-(3-aminophenyl)-1,3-butanedione as a brown oil (3.1 g, 37%). This oil was used in the next step without further purification.

Step 2:

A mixture of 1-(3-aminophenyl)-1,3-butanedione (step 1) (0.5 g, 2.82 mmol), p-tolylhydrazine HCl (0.533 g, 3.36 mmol) and triethylamine (0.340 mL, 3.68 mmol) in ethanol (7 mL) was heated to reflux overnight (about eighteen hours). The resulting dark solution was cooled to room temperature and extracted with ethyl acetate. The organic layer was washed with saturated sodium bicarbonate solution and brine, dried over magnesium sulfate, filtered, and concentrated down to give a brown oil. The oil was purified by column chromatography (silica gel, 1:1 EtOAc/hexane) to yield the titled compound (0.527 g, 65%) as a yellow solid. Mp: 94.38° C. Anal. calc'd for $C_{17}H_{17}N_3$: C 77.57, H 6.46, N 15.97. Found: C 77.14, H 6.56, N 15.77.

EXAMPLE 15

Preparation of

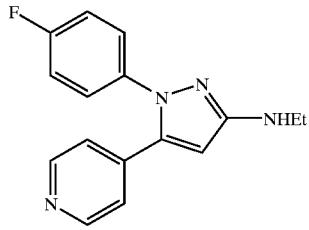

Step 1:

Compound 1: To a solution of LiHMDS (62.5 mL, 1.0 M in THF) at zero degrees C, was added 4-acetylpyridine (6.06 g, 0.05 mol), with 20 mL of DMF also being added to dissolve the anion. To this mixture, a solution of ethyl isothiocyanate (5.49 g, 0.0625 mol) in 30 mL of dry THF was added dropwise over 0.5 hours. The reaction mixture was stirred overnight (about eighteen hours), while warming to room temperature. After the addition of 500 mL of saturated $NH_4Cl$ solution, the aqueous phase was extracted with ethyl acetate. The organic layer was washed with water, brine, dried over magnesium sulfate and filtered. The filtrate was concentrated and purified by chromatography on silica gel (ethyl acetate/hexane, 3:1) to give 2.30 g of the product as a yellow solid (24% yield), mp: 130–132° C.

Step 2:

A mixture of compound 1 (0.4 g, 0.002 mol), 4-fluorophenylhydrazine hydrochloride (0.32 g, 0.002 mol) and triethylamine (0.20 g, 0.002 mol) in 10 mL of ethanol was heated at reflux for 24 hours. After the solvent was removed, the residue was purified by chromatography on silica gel (ethyl acetate/hexane, 8:2) to give 0.31 g of the titled product as a yellow solid (55% yield), mp: 130–131° C.; Anal. Calc'd. for $C_{16}H_{15}FN_4 \cdot 0.25H_2O$: C, 67.00; H, 5.95; N, 19.53. Found: C, 66.98; H, 5.13; N, 19.07.

EXAMPLE 16

Preparation of 1-(4-Fluorophenyl)-5-(4-pyridinyl)-1H-pyrazole-4-carboxamide

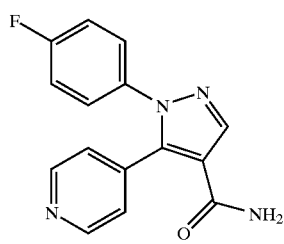

A solution of methyl 1-(4-fluorophenyl)-5-(4-pyridinyl)-1H-pyrazole-4-carboxylate (0.9 g, 0.003 mol) in 10 mL of methanol in a sealed tube treated with excess liquid ammonia at low temperature. Then the reaction mixture was heated at 80° C. for 48 hours. Solvent was removed and the residue was triturated with ethyl acetate to give 0.13 g of product as a yellow solid (15% yield), mp 215–216° C.; Anal. Calcd. For $C_{15}H_{11}FN_4O$: C, 63.38; H, 3.93; N, 19.85. Found: C, 63.21; H, 3.98; N, 19.37.

EXAMPLE 17

Preparation of

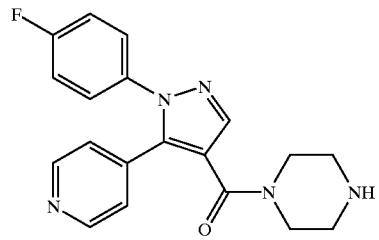

Step 1:

Compound 3: To a solution of the carboxylic acid of Example 43 (0.16 g, 0.00056 mol) in DMF, was added 1-(3-dimethylaminopropyl)-3-ethylcarbodiimide hydrochloride (0.12 g, 0.00062 mol), followed by the addition of N-tert-butoxycarbonylpiperazine (0.10 g, 0.00056 mol). The reaction mixture was stirred at room temperature for 16 hours. Water was added and the aqueous phase was extracted with ethyl acetate. The organic layer was washed with brine, dried over magnesium sulfate and filtered. The filtrate was concentrated and the crude product was purified by recrystallization from ethyl acetate and hexane to give 0.14 g of product as a light yellow solid (55% yield), mp: 233–234° C.; Anal. Calc'd. for $C_{24}H_{26}FN_5O_3$: C, 63.85; H, 5.80; N, 15.51. Found: C, 63.57; H, 6.12; N, 15.42.

Step 2:

To a solution of compound 3 (0.13 g, 0.00029 mol), above, in 5 mL of methylene chloride, were added 2 mL of trifluoroacetic acid. The reaction mixture was stirred at room temperature for 1 hour. Solvent was removed and the residue was basified with ammonium hydroxide. The aqueous phase was extracted with ethyl acetate. The organic layer was washed with brine, dried over magnesium sulfate and filtered. The filtrate was concentrated and the crude was purified by recrystallization from ethyl acetate and ether to give 0.07 g of product as a pale yellow solid (64% yield), mp: 184–186° C.; Anal. Calc'd. for $C_{19}H_{18}FN_5O$: C, 64.95; H, 5.16; N, 19.93. Found: C, 64.50; H, 5.02; N, 19.86.

EXAMPLE 18

Preparation of

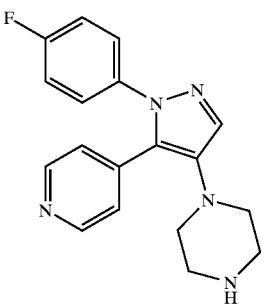

Step 1:

Compound 4: To a solution of 4-acetylpyridine (18.2 g, 0.15 mol) in 30 mL of 48% HBr was added a solution of $Br_2$ (24.0 g, 0.15 mol) in 5 mL of 48% HBr dropwise at 70° C.

After stirring at the same temperature for 3 hours, the suspension was cooled and filtered. The solid was washed with a mixture of methanol and petroleum ether to give 28.9 g of product as a pale yellow solid (69% yield), mp: 210° C. (dec).

Step 2:

Compound 5: Triethylamine (7.5 mL, 0.54 mol) was added to a suspension of compound 4 (7.8 g, 0.027 mol) and N-tert-butoxycarbonylpiperazine (5.0 g, 0.027 mol) in DMF at room temperature. After heating at 80° C. for 16 hours, the reaction mixture was cooled and treated with water. The aqueous phase was saturated with sodium chloride and extracted with ethyl acetate. The organic layer was washed with brine, dried over magnesium sulfate and filtered. The filtrate was concentrated and the crude was purified by chromatography on silica gel (ethyl acetate) to give 2.2 g of product as a yellow oil (27% yield).

Step 3:

To a solution of compound 5 (2.0 g, 0.0065 mol) in THF was added N, N-dimethylformamide dimethyl acetal (7.8 g 0.065 mol). After stirring at room temperature for 24 hours, solvent was removed under vacuum to give 2.5 g of crude as a dark brown oil. This crude product was then dissolved in 50 mL of ethanol, treated with 4-fluorophenylhydrazine and the mixture was heated at reflux overnight (about eighteen hours). After the removal of solvent, the residue was partitioned between water and ethyl acetate. The organic layer was washed with brine, dried over magnesium sulfate and filtered. The filtrate was concentrated and the crude (0.7 g) was dissolved in 5 mL of methylene chloride and treated with 2 mL of TFA. After stirring at room temperature for 16 hours, the mixture was concentrated.

The concentrated residue was basified with 1N NaOH, and extracted with ethyl acetate. The organic layer was washed with brine, dried over magnesium sulfate and filtered. The filtrate was concentrated and purified by chromatography on silica gel (methylene chloride/methanol, 9:1) to give 0.25 g of the titled compound as a yellow solid, mp: 150–151° C.; Anal. Calc'd. for $C_{18}H_{18}FN_5 \cdot 2.0H_2O$: C, 60.15; H, 6.17; N, 19.49. Found: C, 60.37; H, 5.74; N, 19.98.

EXAMPLE 19

Preparation of 2-(Benzylamino)-4-[1-(3-methylphenyl)-3-methyl-1H-pyrazol-5-yl]pyridine

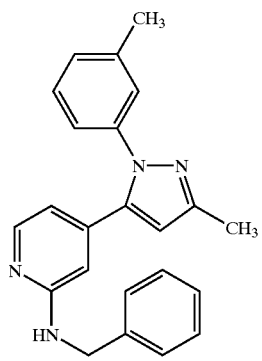

A mixture of 2-chloro-4-[1-(3-methylphenyl)-3-methyl-1H-pyrazol-5-yl]pyridine (Example 45; 1.24 g, 0.0044 mol) and benzylamine (40 mL) was heated at 180° C. for 20 hours The excess benzylamine was removed under vacuum and the residue was partitioned between ethyl acetate and water. The organic layer was washed with brine, dried over magnesium sulfate and filtered. The filtrate was concentrated and the crude product was purified by chromatography on silica gel (ethyl acetate/hexane, 3:7) to give 1.33 g (85% yield) of the titled compound as a clear oil, which solidified upon standing: mp: 73–75° C. Anal. Calc'd. for $C_{23}H_{22}N_4 \cdot 0.2H_2O$: C, 76.83; H, 6.39; N, 15.06. Found: C, 76.88; H, 6.37; N, 14.92.

EXAMPLE 20

Preparation of 2-(Benzylamino)-4-[1-(3-fluorophenyl)-3-methyl-1H-pyrazol-5-yl]pyridine

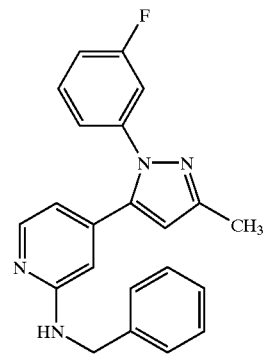

A mixture of 2-chloro-4-[1-(3-fluorophenyl)-3-methyl-1H-pyrazol-5-yl]pyridine (Example 47; 1.11 g, 0.0039 mol) and benzylamine (30 mL) was heated at 180° C. overnight (about eighteen hours). The excess benzylamine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 1.24 g (90% yield) of the titled compound as a clear oil, which solidified upon standing: mp: 94–96° C.; Anal. Calc'd. for $C_{22}H_{19}FN_4$: C, 73.72; H, 5.34; N, 15.63. Found: C, 73.62; H, 5.62; N, 15.34.

EXAMPLE 21

Preparation of 2-Amino-4-[1-(3-methylphenyl)-3-methyl-1H-pyrazol-5-yl]pyridine

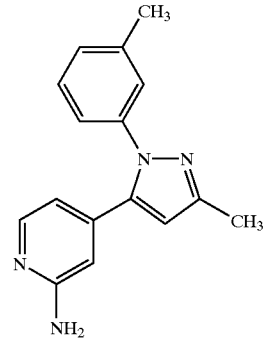

A mixture of 2-benzylamino-4-[1-(3-methylphenyl)-3-methyl-1H-pyrazol-5-yl]pyridine (Example 19; 1.03 g, 0.0029 mol) and palladium hydroxide (0.2 g)in acetic acid was hydrogenated under 60 psi at 40° C. for 9 hours. The mixture was cooled and filtered through a pad of Celite™. The filtrate was concentrated and purified by chromatography on silica gel (ethyl acetate/hexane, 1:1) to give 0.43 g of product as a white solid: mp: 124–125° C.; Anal. Calc'd. for $C_{16}H_{16}N_4$: C, 72.70; H, 6.10; N, 21.20. Found: C, 72.41; H, 6.31; N, 20.63.

EXAMPLE 22

Preparation of 2-Methoxy-4-[1-(3-methylphenyl)-3-methyl-1H-pyrazol-5-yl]pyridine

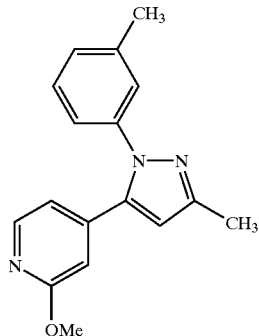

Step 1: Preparation of Methyl 2-Methoxyisonicotinate

A mixture of methyl 2-chloroisonicotinate (5.23 g, 0.030 mol) and sodium methoxide (2.47 g, 0.045 mol) in 15 mL of dioxane was heated at reflux for 1.5 hours. After the reaction mixture was cooled, water was added and the resulting mixture was extracted with methylene chloride. The organic layer was washed with brine, dried over magnesium sulfate and filtered. The filtrate was concentrated in vacuo to give 3.76 g (75%) of product as a yellow oil: Anal. Calc'd. for $C_8H_9NO_3$: C, 57.48; H, 5.43; N, 8.38. Found: C, 57.07; H, 5.54; N, 8.34.

Step 2: Preparation of 1-(2-Methoxypyridyl)-1,3-butadione

To a solution of methyl 2-methoxyisonicotinate (3.67 g, 0.022 mol) and acetone (4.85 mL, 0.066 mol) in 30 mL of THF was added sodium methoxide (1.25 g, 0.023 mol) in one portion. The reaction mixture was refluxed for 4 hours and then cooled to room temperature. Water was added and the solution was acidified to pH=6 by acetic acid. The aqueous phase was extracted with ethyl acetate and the organic layer was washed with brine, dried over magnesium sulfate and filtered. The filtrate was concentrated to give 2.79 g (72%) of product as a brown solid that was used without further purification.

Step 3: Preparation of 2-Methoxy-4-[1-(3-methylphenyl)-3-methyl-1H-pyrazol-5-yl]pyridine:

To a suspension of 1-(2-methoxypyridyl)-1,3-butadione (2.7 g, 0.014 mol) and 3-methylphenylhydrazine hydrochloride (2.66 g, 0.017 mol) in 100 mL of ethanol was added triethylainine (2.34 mL, 0.017 mol) dropwise. The reaction mixture was heated at refluxed overnight (about eighteen hours). Solvent was removed and the residue was partitioned between ethyl acetate and water. Organic layer was washed with brine, dried over magnesium sulfate and filtered. The filtrate was concentrated and the crude was purified by chromatography on silica gel (ethyl acetate/hexane, 2:8) to give 2.8 g (72%) of product as a yellow oil: Anal. Calc'd. for $C_{17}H_{17}N_3O$: C, 73.10; H, 6.13; N, 15.04. Found: C, 72.81; H, 6.11; N, 14.68.

EXAMPLE 23

Preparation of 4-[1-(3-Methylphenyl)-3-methyl-1H-pyrazol-5-yl]-2-pyridone

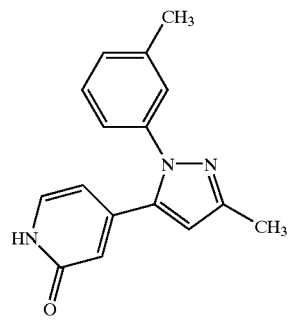

To a solution of 2-methoxy-4-[1-(3-methylphenyl)-3-methyl-1H-pyrazol-5-yl]pyridine (Example 22; 0.56 g, 0.002 mol) in 5 mL of acetic acid was added 5 mL of hydrobromic acid. The reaction mixture was heated at reflux for 3 hours and then cooled to room temperature. Water was added and the solution was basified with ammonium hydroxide. The aqueous phase was extracted with ethyl acetate and the organic layer was washed with brine, dried over magnesium sulfate and filtered. The filtrate was concentrated in vacuo to give 0.45 g (85%) of product as a white solid: mp: 182–183° C.; Anal. Calc'd. for $C_{16}H_{15}N_3O$: C, 72.43; H, 5.70; N, 15.84. Found: C, 72.37; H, 5.66; N, 15.97.

EXAMPLE 24

Preparation of 2-(Phenylethylamino)-4-[1-(3-methylphenyl)-3-methyl-1H-pyrazol-5-yl]pyridine

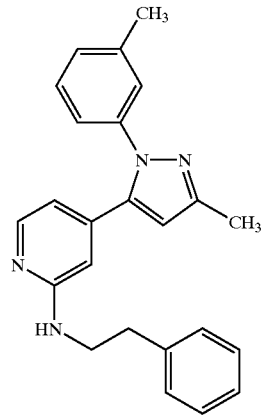

A mixture of 2-chloro-4-[1-(3-methylphenyl)-3-methyl-1H-pyrazol-5-yl]pyridine (Example 45; 0.5 g, 0.0018 mol) and phenethylamine (15 mL) was heated at 200° C. for 24 hours. The excess amine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 1:1) to give 0.48 g (74% yield) of product as a yellow oil, which solidified upon standing: mp: 86–87° C. Anal. Calc'd. for $C_{24}H_{24}N_4$: C, 78.23; H, 6.56; N, 15.20. Found: C, 78.07; H, 6.82; N, 14.71.

EXAMPLE 25

Preparation of 2-(N-Methylphenylethylamino)-4-[1-(3-methylphenyl)-3-methyl-1H-pyrazol-5-yl]pyridine

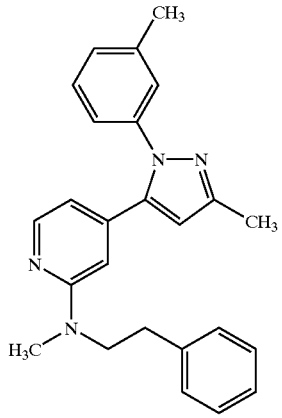

A mixture of 2-chloro-4-[1-(3-methylphenyl)-3-methyl-1H-pyrazol-5-yl]pyridine (Example 45; 0.5 g, 0.0018 mol) and N-methylphenethylamine (15 mL) was heated at 200° C. for 24 hours. The excess amine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 0.45 g (67% yield) of product as a yellow oil: Anal. Calc'd. for $C_{25}H_{26}N_4$: C, 78.50; H, 6.85; N, 14.65. Found: C, 78.43; H, 6.87; N, 14.30.

EXAMPLE 26

Preparation of 2-(2-Hydroxyethylamino)-4-[1-(3-methylphenyl)-3-methyl-1H-pyrazol-5-yl]pyridine

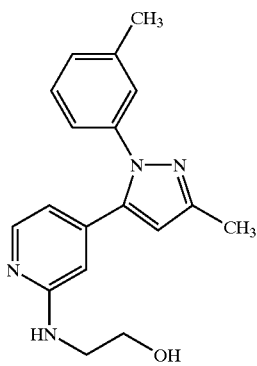

A mixture of 2-chloro-4-[1-(3-methylphenyl)-3-methyl-1H-pyrazol-5-yl]pyridine (Example 45; 0.5 g, 0.0018 mol) and ethanolamine (15 mL) was heated at 100° C. for 18 hours. The reaction mixture was cooled and treated with ethyl acetate and water. The organic layer was washed with brine, dried over magnesium sulfate and filtered. The filtrate was concentrated and the crude was purified by chromatography on silica gel (ethyl acetate) to give 0.44 g (80% yield) of product as a yellow oil: Anal. Calc'd. for $C_{18}H_{20}N_4O$: C, 70.11; H, 6.54; N, 18.17. Found: C, 69.89; H, 6.65; N, 18.35.

EXAMPLE 27

Preparation of 2-(N-Methylbenzylamino)-4-[1-(3-methylphenyl)-3-methyl-1H-pyrazol-5-yl]pyridine

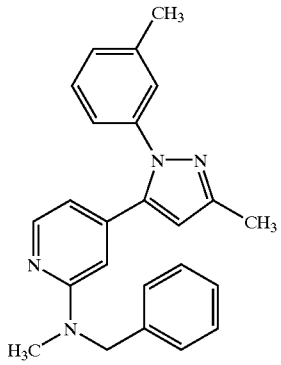

A mixture of 2-chloro-4-[1-(3-methylphenyl)-3-methyl-1H-pyrazol-5-yl]pyridine (Example 45; 1.0 g, 0.0036 mol) and N-methylbenzylamine (20 mL) was heated at 180° C. for 24 hours. The excess amine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 0.88 g (66% yield) of product as a yellow oil: Anal. Calc'd. for $C_{24}H_{24}N_4$: C, 78.23; H, 6.56; N, 15.20. Found: C, 78.55; H, 6.51; N, 15.21.

EXAMPLE 28

Preparation of 2-Bezyloxy-4-[1-(3-methylphenyl)-3-methyl-1H-pyrazol-5-yl]pyridine

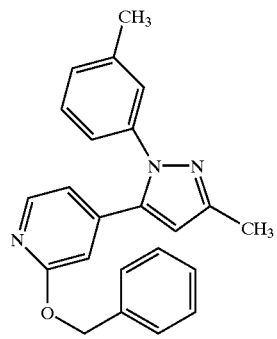

To a suspension of potassium hydroxide (0.67 g, 0.012 mol) and potassium carbonate (0.41 g, 0.003 mol) in 30 mL of toluene was added 2-chloro-4-[1-(3-methylphenyl)-3-methyl-1H-pyrazol-5-yl]pyridine (0.85 g, 0.003 mol). Then benzyl alcohol (0.49 g, 0.0045 mol) was charged into the reaction mixture, followed by the addition of tris[2-(2-methoxyethoxy)ethyl]amine (0.1 g, 0.0003 mol) and the mixture was heated at reflux overnight (about eighteen hours). Toluene was removed under vacuum and the residue was partitioned between water and ethyl acetate.

The organic layer was washed with brine, dried over magnesium sulfate and filtered. The filtrate was concentrated and the crude was purified by chromatography on silica gel (ethyl acetate/hexane, 1:9) to give 0.82 g (66% yield) of product as a yellow oil: Anal. Calc'd. for $C_{23}H_{21}N_3O$: C, 77.72; H, 5.96; N, 11.82. Found: C, 77.42; H, 5.90; N, 11.55.

EXAMPLE 29

Preparation of 2-(Benzylamino)-4-[1-(4-fluorophenyl)-1H-pyrazol-5-yl]pyridine

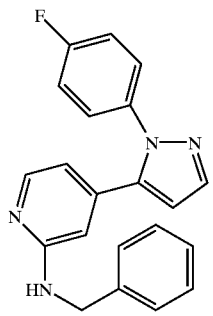

A mixture of 2-chloro-4-[1-(4-fluorophenyl)-1H-pyrazol-5-yl]pyridine (Example 46; 0.56 g, 0.002 mol) and benzylamine (20 mL) was heated at 180° C. overnight (about eighteen hours). The excess benzylamine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 3:7) to give 0.63 g (89% yield) of product as a white solid: mp: 125–127° C.; Anal. Calc'd. for $C_{22}H_{17}FN_4$: C, 73.24; H, 4.98; N, 16.27. Found: C, 72.89; H, 4.69; N, 15.82.

EXAMPLE 30

Preparation of 2-(Phenylethylamino)-4-[1-(4-fluorophenyl)-1H-pyrazol-5-yl]pyridine

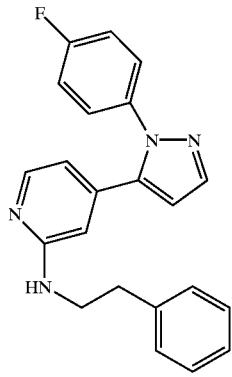

A mixture of 2-chloro-4-[1-(4-fluorophenyl)-1H-pyrazol-5-yl]pyridine (Example 46; 0.6 g, 0.002 mol) and phenethylamine (20 mL) was heated at 190° C. for 24 hours. The excess amine was removed under vacuum and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 0.55 g (70% yield) of product as a yellow oil: Anal. Calc'd. for $C_{22}H_{19}FN_4$: C, 73.72; H, 5.34; N, 15.63. Found: C, 73.33; H, 5.46; N, 15.22.

EXAMPLE 31

Preparation of 2-Cyano-4-[1-(3-methylphenyl)-3-methyl-1H-pyrazol-5-yl]pyridine

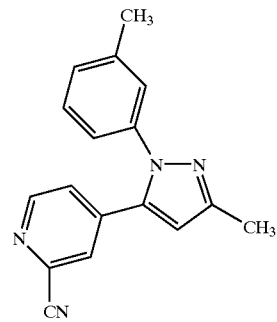

Step 1: Preparation of Methyl Isonicotinate N-Oxide:

To a solution of hydrogen peroxide (43 mL) in 250 mL of acetic acid was added methyl isonicotinate. The reaction mixture was stirred at 80° C. overnight (about eighteen hours). The solution was concentrated to about 50 mL, water was added and the mixture was saturated with sodium carbonate. The aqueous phase was extracted with methylene chloride. The organic layer was washed with brine, dried over magnesium sulfate and filtered. The filtrate was concentrated and triturated with hexane. The resulting precipitate was filtered and air-dried to give 24.5 g (65% yield) of product as a white solid: mp: 118–120° C.

Step 2: Preparation of Methyl 2-Cyanoisonicotinate:

To a solution of methyl isonicotinate N-oxide (20.0 g, 0.26 mol) in 200 mL of methylene chloride was added trimethylsilyl cyanide (16.1 g, 0.32 mol), followed by a solution of dimethylcarbamyl chloride (17.82 g, 0.32 mol) in 50 mL of methylene chloride at room temperature. The reaction mixture was stirred overnight (about eighteen hours) and then treated with 500 mL of 10% potassium carbonate solution. The organic layer was washed with brine, dried over magnesium sulfate and filtered. The filtrate was concentrated to 15.2 g of crude product as a brown solid, which was used without further purification.

Step 3: Preparation of 1-(2-Cyanoisonicotinyl)-1,3-butanedione:

To a solution of methyl 2-cyanoisonicotinate (20.0 g, 0.126 mol) in 250 mL THF was added acetone (30.6 mL, 0.42 mol). The solution was warmed to 35° C. and sodium methoxide (7.15 g, 0.132 mol) was added portionwise over 20 minutes. The mixture was heated at reflux for 16 hours. The solvent was removed in vacuo and the residue was dissolved in water, acidified to pH=6 with acetic acid. The aqueous phase was extracted with ethyl acetate and the organic layer was washed with brine, dried over magnesium sulfate, filtered and concentrated in vacuo to yield 13.0 g (58% yield) of product as a brown solid, which was used in next step without purification.

Step 4: Preparation of 2-Cyano-4-[1-(3-methylphenyl)-3-methyl-1H-pyrazol-5-yl]pyridine To a mixture of 1-(2-cyanoisonicotinyl)-1,3-butanedione (1.10 g, 0.0058 mol) and 3-methylphenylhydrazine hydrochloride (0.97 g, 0.0061 mol) in 20 mL of ethanol was added triethylamine (0.85 mL, 0.0061 mol) dropwise. The reaction mixture was heated at reflux overnight (about eighteen hours). The solvent was removed and the residue was partitioned between ethyl acetate and water. The organic layer was washed with brine, dried over magnesium sulfate and filtered. The filtrate was concentrated and the crude product was purified by chromatography on silica gel (ethyl acetate/hexane, 2:8) to give 1.30 g (87% yield) of product as a yellow solid: mp: 128–130° C.; Anal. Calc'd. for $C_{17}H_{14}N_4$: C, 74.43; H, 5.14; N, 20.42. Found: C, 74.53; H, 5.22; N, 20.29.

EXAMPLE 32

Preparation of 2-Cyano-4-[1-(4-fluorophenyl)-3-methyl-1H-pyrazol-5-yl]pyridine

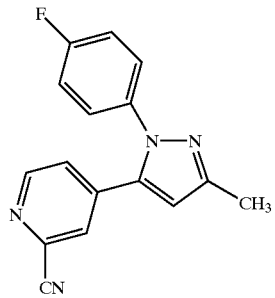

Triethylamine (4.6 mL, 0.033 mol) was added dropwise to a mixture of 1-(2-cyanoisonicotinyl)-1,3-butanedione (6.0 g, 0.032 mol) and 4-fluorophenylhydrazine hydrochloride (5.37 g, 0.033 mol) in 100 mL of ethanol. The reaction mixture was heated at reflux overnight (about eighteen hours). The solvent was removed and the residue was partitioned between ethyl acetate and water. The organic layer was washed with brine, dried over magnesium sulfate and filtered. The filtrate was concentrated and the crude was purified by recrystallization from ether/hexane to give 4.7 g (53% yield) of product as a yellow solid: mp: 94–95° C.; Anal. Calc'd. for $C_{16}H_{11}FN_4$: C, 69.06; H, 3.98; N, 20.13. Found: C, 68.52; H, 3.89; N, 19.73.

EXAMPLE 33

Preparation of {4-[1-(3-Methylphenyl)-3-methyl-1H-pyrazol-5-yl]}-2-pyridine-2-carboxamide

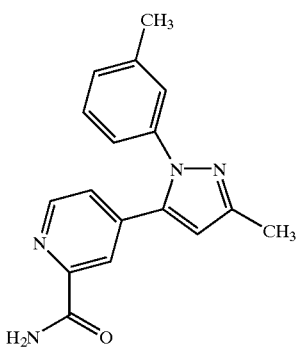

To a solution of 2-cyano-4-[1-(3-methylphenyl)-3-methyl-1H-pyrazol-5-yl]pyridine (Example 31; 0.16 g, 0.0006 mol) in 5 mL of DMSO was added hydrogen peroxide (0.072 mL, 0.0006 mol) and potassium carbonate (0.012 g, 0.00009 mol) at zero degrees C. The reaction mixture was warmed up to room temperature over 30 minutes. Water was added and the mixture was stirred for 0.5 hours. The resulting precipitate was collected by filtration to give 0.12 g (70% yield) of product as a pale yellow solid: mp: 193–195° C.; Anal. Calc'd. for $C_{17}H_{16}N_4O$: C, 69.85; H, 5.52; N, 19.16. Found: C, 69.84; H, 5.40; N, 19.11.

EXAMPLE 34

Preparation of {4-[1-(4-Fluorophenyl)-3-methyl-1H-pyrazol-5-yl]}pyridine-2-carboxamide

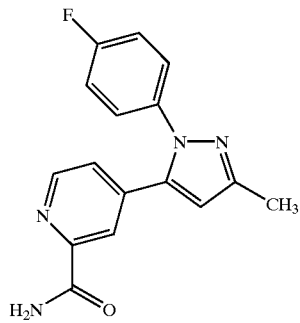

To a solution of 2-cyano-4-[1-(4-fluorophenyl)-3-methyl-1H-pyrazol-5-yl]pyridine (Example 32; 1.0 g, 0.0036 mol) in 25 mL of DMSO was added hydrogen peroxide (0.43 mL, 0.0036 mol) and potassium carbonate (0.072 g, 0.00051 mol) at zero degrees C. The reaction mixture was warmed up to room temperature over 1 hour. Water was added and the mixture was stirred for 0.5 hours. The resulting precipitate was collected by filtration to give 0.95 g (89% yield) of product as a pale yellow solid: mp: 168–170° C.; Anal. Calc'd. for $C_{16}H_{13}FN_4O$: C, 64.86; H, 4.42; N, 18.91. Found: C, 64.48; H, 4.27; N, 18.80.

EXAMPLE 35

Preparation of 2-(Dimethylamino)-4-[1-(3-methylphenyl)-3-methyl-1H-pyrazol-5-yl]pyridine

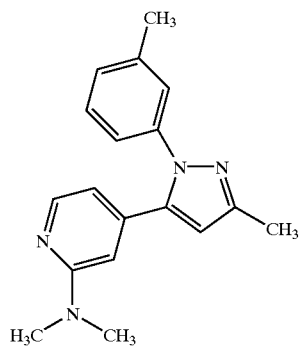

A mixture of 2-chloro-4-[1-(3-methylphenyl)-3-methyl-1H-pyrazol-5-yl]pyridine (Example 45; 0.91 g, 0.0032 mol) and 50 mL of liquid ammonia in 20 mL of DMF was stirred in a sealed tube under 1800 psi, at 180° C. for 72 hours. After the solution was cooled, the solvent was removed under vacuum and the residue was purified by chromatography on silica gel (ethyl acetate/hexane, 2:8) to give 0.73 g (78% yield) of product as a yellow crystal: mp: 84–85° C.; Anal. Calc'd. for $C_{18}H_{20}N_4$: C, 73.94; H, 6.89; N. 19.16. Found: C, 73.68; H, 6.74; N, 19.13.

EXAMPLE 36

Preparation of 2-(Methylsulfonyl)-4-[1-(3-methylphenyl)-3-methyl-1H-pyrazol-5-yl]pyridine

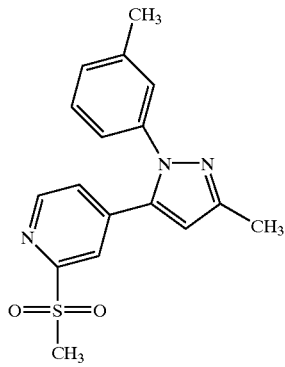

A mixture of 2-chloro-4-[1-(3-methylphenyl)-3-methyl-1H-pyrazol-5-yl]pyridine (Example 45; 1.0 g, 0.0035 mol) and methanesulfonic acid sodium salt (3.24 g, 0.021 mol) in 15 mL of DMF was heated at 140° C. for 24 hours. After the mixture was cooled, water was added and the aqueous phase was extracted with ethyl acetate. The organic layer was washed with brine, dried over magnesium sulfate and filtered. The filtrate was concentrated and the crude was purified by chromatography on silica gel (ethyl acetate/hexane, 1:1) to give 0.45 g (40% yield) of product as a yellow solid: mp: 140–142° C.; Anal. Calc'd. for $C_{17}H_{17}N_3SO_2$: C, 62.36; H, 5.23; N, 12.83; S, 9.79. Found: C, 62.16; H, 5.31; N, 12.74; S, 9.86.

EXAMPLE 37

Preparation of {4-[1-(3-Fluorophenyl)-3-methyl-1H-pyrazol-5-yl]}pyridine-2-azide

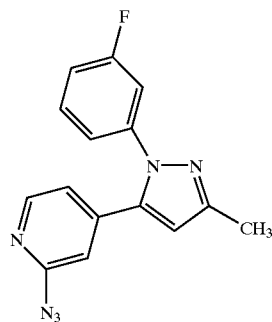

A mixture of 2-chloro-4-[1-(3-fluorophenyl)-3-methyl-1H-pyrazol-5-yl]pyridine (Example 47; 0.87 g, 0.003 mol) sodium azide (0.59 g, 0.009 mol) in 15 mL of DMF was heated at 100° C. for 120 hours. After the mixture was cooled, water was added and the aqueous phase was extracted with ethyl acetate. The organic layer was washed with brine, dried over magnesium sulfate and filtered. The filtrate was concentrated and the crude was purified by chromatography on silica gel (ethyl acetate/hexane, 1:1) to give 0.13 g (15% yield) of product as a yellow solid: mp: 134–135° C.; Anal. Calc'd. for $C_{15}H_{11}FN_6$: C, 61.22; H, 3.77; N, 28.56. Found: C, 61.44; H, 3.67; N, 28.00.

EXAMPLE 38

Preparation of 2-(3-Pyridylmethylamino)-4-[1-(3-fluorophenyl)-3-methyl-1H-pyrazol-5-yl]pyridine

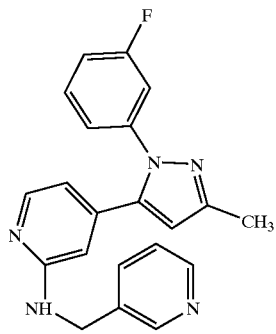

A mixture of 2-chloro-4-[1-(3-fluorophenyl)-3-methyl-1H-pyrazol-5-yl]pyridine (Example 47; 0.48 g, 0.0017 mol) and 3-(aminomethyl)pyridine (10 mL) was heated at 190° C. overnight (about eighteen hours). The reaction mixture was cooled, treated with copious amount of water and extracted with ethyl acetate. The organic layer was washed with brine, dried over magnesium sulfate and filtered. The filtrate was concentrated and the crude was purified by chromatography on silica gel (ethyl acetate/triethylamine, 99:1) to give 0.35 g (60% yield) of product as a yellow oil: Anal. Calc'd. for $C_{21}H_{18}FN_5$: C, 70.18; H, 5.05; N, 19.49. Found: C, 69.78; H, 5.35; N, 18.87.

EXAMPLE 39

Preparation of

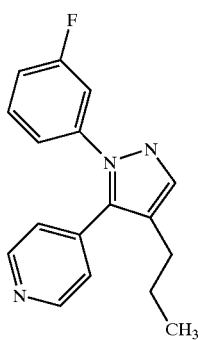

The titled compound was synthesized using 4-pentanoylpyridine as the starting material following the procedures described in Example 1, except that 3-fluorophenylhydrazine was substituted for 4-fluorophenylhydrazine. 4-Butanoylpyridine and 4-pentanoylpyridine both can be synthesized according to procedures described by J. L. Born and S. Early in *J. Pharm. Sci.*, vol. 69, pp. 850–851, (1980). m.p. 93–94 ° C. Anal. Calc'd. for $C_{17}H_{16}FN_3$: C, 72.58; H, 5.73; N, 14.94. Found: C, 72.44; H, 5.81; N, 14.67.

EXAMPLE 40

Preparation of

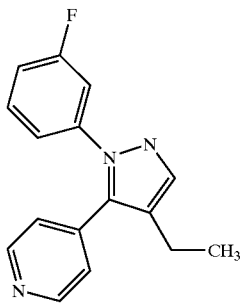

This compound was synthesized using 4-butanoylpyridine as the starting material following the procedures described in Example 25, except that 3-fluorophenylhydrazine was substituted for 4-fluorophenylhydrazine. 4-Butanoylpyridine and 4-pentanoylpyridine both can be synthesized according to procedures described by J. L. Born and S. Early in *J. Pharm. Sci.*, vol. 69, pp. 850–851, (1980). M.p. 109–110° C. Anal. Calc'd. for $C_{16}H_{14}FN_3$: C, 71.89; H, 5.28; N, 15.72. Found: C, 71.58; H, 5.18; N, 15.61.

EXAMPLE 41

Preparation of 2-Chloro-4-[3-methyl-1-(4-methylphenyl)-1H-pyrazol-5-yl]pyridine

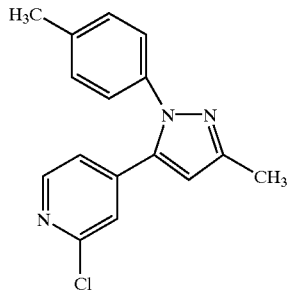

Step 1: Preparation of Methyl-2-chloroisonicotinate

To a solution of thionyl chloride (13.85 mL, 190.38 mmol) in toluene (50 mL) was added 2-chloropyridine-4-carboxylic acid (15 g, 95 mmol). The solution was heated to reflux for 3 hours. The resulting brown color solution was cooled to room temperature, and methanol (11.56 mL, 285.6 mmol) was added slowly dropwise. The mixture was brought to reflux for 15 minutes and became clear. The solution was then cooled to room temperature and poured into water (150 mL), basified with 50 percent sodium hydroxide and extracted with ethyl acetate (2×200 ml). The organic layer was separated and washed with brine, dried with magnesium sulfate, filtered and concentrated to yield the titled compound (11.93 g, 73%) as a brown color solid. This was used in the next step without further purification.

Step 2: Preparation of 1-(2-Chloro-4-pyridinyl)-1,3-butanedione

To a solution of methyl-2-chloroisonicotinate (11.93 g, 69.53 mmol) in THF (200 mL) was added acetone (14.19 mL, 153 mmol). The solution was warmed to 35° C. when sodium methoxide (94.13 g, 76.48 mmol) was added sequentially over 20 minutes. The mixture was stirred for 30 minutes, and then brought to reflux for 2.5 hours. The solvent was removed under reduced pressure and then taken up in ethyl acetate. The resulting solution was washed with saturated sodium bicarbonate solution and brine, dried over magnesium sulfate, filtered and concentrated to yield 1-(2-chloro-4-pyridinyl)-1,3-butanedione (4.97 g, 76%) as a light brown colored solid. This was used in the next step without further purification.

Step 3: Preparation of 2-Chloro-4-[3-methyl-1-(4-methylphenyl)-1H-pyrazol-5-yl]pyridine)

A mixture of 1-(2-chloro-4-pyridinyl)-1,3-butanedione (7 g, 35.25 mmol), paratolylhydrazine.HCl (6.13 g, 38.78 mmol) and triethylamine (5.41 mL, 38.78 mmol) in methanol (100 mL) was heated to reflux overnight. The resulting dark colored solution was cooled to room temperature and extracted with ethyl acetate. The organic layer was washed with saturated sodium bicarbonate and brine, and dried over magnesium sulfate. After filtration, the solution was concentrated to give a brown solid. The solid was purified by column chromatography (silica gel, 2:8 EtOAc/hexane) to yield the titled product (3.6 g, 52%) as a crystalline light brown solid. MP: 100.07° C. Anal. Calc'd for $C_{16}H_{14}N_3Cl$: C, 67.72, H, 4.97, N, 14.81. Found: C 67.40, H, 4.89, N, 14.59.

EXAMPLE 42

Preparation of 1-(4-Fluorophenyl)-5-(4-pyridinyl)-1H-pyrazole-4-carboxylate

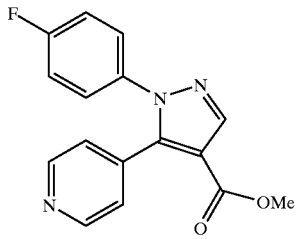

Step 1: Preparation of Compound 6

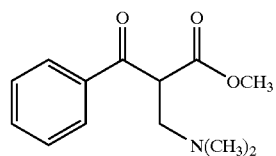

Compound 6: To a solution of methyl isonicotinate (25.0 g, 0.182 mol)in 100 mL of methyl acetate was added NaOMe (10.8 g, 0.2 mol). The reaction mixture was heated at reflux for 3 hours and cooled to room temperature. Water was added and extracted with ethyl acetate. The organic layer was washed with brine, dried over magnesium sulfate and filtered. The filtrate was concentrated and the residue was triturated with hexane to give 14.0 g of product as a pale yellow solid. To a solution of this compound (13.0 g, 0.072 mol) in THF, was added N,N-dimethylformamide dimethyl acetal (51.9 g, 0.43 mol), and the mixture was stirred at room temperature for 36 hours. The solvent was removed and the residue was dissolved with water and saturated with sodium chloride. The aqueous phase was extracted with methylene chloride, the organic layer was washed with brine, dried over magnesium sulfate and filtered. The filtrate was concentrated to afford 13.2 g of crude product as a yellow oil that was used without further purification in the next step.

Step 2: Preparation of Methyl 1-(4-Fluorophenyl)-5-(4-pyridinyl)-1H-pyrazole-4-carboxylate)

To a solution of the crude compound 6 (2.5 g 0.011 mol) in 50 mL of a mixture of water and ethanol (1:1), was added 4-fluorophenylhydrazine hydrochloride (1.71 g, 0.011 mol), and the solution was stirred at 50° C. for 2 hours. After the solvent was removed, the residue was basified by ammonia hydroxide. The resulting precipitate was filtered, and air-dried to give 2.05 g of product as a yellow solid (64% yield), mp: 119–120° C.; Anal. Calcd. for $C_{16}H_{12}FN_3O_2$: C, 64.64; H, 4.07; N, 14.13. Found: C, 64.28; H, 3.87; N, 14.14.

EXAMPLE 43

Preparation of

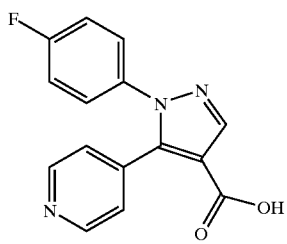

To a solution of methyl 1-(4-fluorophenyl)-5-(4-pyridinyl)-1H-pyrazole-4-carboxylate (Example 42; 0.6 g, 0.002 mol) in 20 mL of ethanol were added 4.0 mL of 1N NaOH solution. The reaction mixture was stirred at room temperature for 16 hours. After the solvent was removed, the residue was acidified with 1N HCl. The precipitate was filtered and air-dried to give 0.25 g of product as a pale yellow solid (45% yield), mp: 299–300° C.; Anal. Calcd. for $C_{15}H_{02}FN_3O_2H_2O$: C, 59.80; H, 4.01; N, 13.95. Found: C, 59.91; H, 3.52; N, 13.63.

EXAMPLE 44

Preparation of 2-Chloro-4-[1-(3-Methylphenyl)-3-methyl-1H-pyrazol-5-yl]pyridine

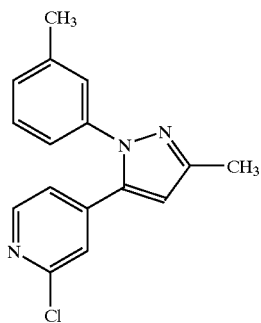

To a mixture of 1-(2-chloroisonicotinyl)-1,3-butanedione (1.35 g, 0.068 mol) and 3-methylphenylhydrazine hydrochloride (1.30 g, 0.0082 mol) in ethanol (40 mL) was added ammonia hydroxide (0.96 mL, 0.0082 mol) dropwise. The reaction mixture was heated at reflux overnight. The solvent was removed and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 1.68 g (87% yield) of product as a yellow oil: Anal. Calcd. for $C_{16}H_{14}ClN_3$: C, 67.72; H, 4.97; N, 14.81; Cl, 12.49. Found: C, 67.91; H, 5.08; N, 14.79; Cl, 12.40.

EXAMPLE 45

Preparation of 2-Chloro-4-[1-(4-fluorophenyl)-1H-pyrazol-5-yl]pyridine

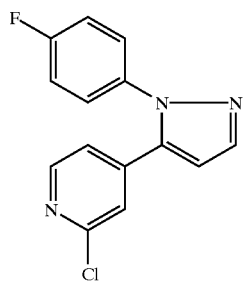

Step 1: Preparation of 2-Chloro-4-(N-methyl-N-methoxycarbamoyl)pyridine

To a suspension of 2-chloroisonicotinic acid (18.0 g, 0.105 mol) in 250 mL of methylenechloride was added 1,1'-carbonyldiimidazole (17.0 g, 0.105 mol) portionwise. The mixture was stirred for 0.5 h and N,O-dimethylhydroxylamine hydrochloride (10.2 g, 0.105 mol) was added rapidly. The reaction mixture was stirred at room temperature overnight. Ether was added and the organic layer was washed with water, dried, dried over magnesium sulfate and filtered. The filtrate was concentrated to give 14.5 g (70%) of product as a yellow oil. This was used in next step without purification.

Step 2: Preparation of 2-Chloro-4-acetylpyridine

To methylmagnesium bromide (30 mL of 3.0 M in THF) was added a solution of 2-chloro-4-(N-methyl-N-methoxycarbamoyl)pyridine (6.0 g, 0.03 mol) in 20 mL of THF at 0 C. The reaction mixture was stirred overnight while allowing to warm up to room temperature. A solution of potassium hydrogensulfate (12 g) in 300 mL of water was added and the aqueous phase was extracted with ethyl acetate. The organic layer was washed with brine, dried over magnesium sulfate and filtered. The filtrate was concentrated 4.0 g (86%) of product as a yellow oil. This was used in next step without purification.

Step 3: Preparation of 1-[2-Chloroisonicotinyl)-2-(dimethylaminomethylene)ethanone A mixture of 2-chloro-4-acetylpyridine (9.1 g, 0.058 mol) in 45 mL of N,N-dimethylformamide dimethyl acetal was heated at reflux for 3 h. The dark solution was cooled and treated with 300 mL of hexane. The precipitate was collected by filtration and air-dried to give 14.6 g of product as a brownish solid (70%), which was used without further purification.

Step 4: Preparation of 2-Chloro-4-[1-(4-fluorophenyl)-1H-pyrazol-5-yl]pyridine

To a mixture of 1-(4-pyridyl)-2-(dimethylaminomethylene)ethanone (2.1 g, 0.01 mol) and 4-fluorophenylhydrazine hydrochloride (1.63 g, 0.01 mol) in 50 mL of ethanol was added 1 mL of water. The reaction mixture was heated at reflux for 1.5 h. Solvent was removed and the residue was partitioned between water and ethyl acetate. The organic layer was washed with brine, dried over magnesium sulfate and filtered. The filtrate was concentrated and the crude was purified by chromatography on silica gel (ethyl acetate/hexane, 2:8) to give 2.5 g (93% yield) of product as a yellow oil: Anal. Calcd. for $C_{14}H_9ClFN_3$: C, 61.44; H, 3.31; N, 15.35. Found: C, 61.52; H, 3.27; N, 14.73.

EXAMPLE 46

Preparation of 2-Chloro-4-[1-(3-fluorophenyl)-3-methyl-1H-pyrazol-5-yl]pyridine

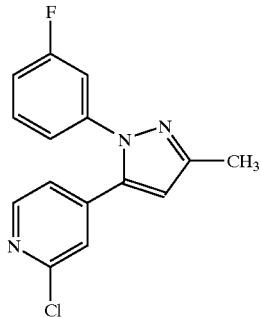

Step 1: Preparation of 2-Chloroisonicotinic Acid:

A mixture of isonicotinic acid N-oxide (28.0 g, 0.2 mol) and phosphorus oxychloride (120.0 g, 0.8 mol) was heated at reflux for 7 h. The reaction mixture was cooled and carefully poured into 600 mL of ice water. The precipitate was collected by filtration to give 20.6 g (65% yield) of product as a pale yellow solid, mp: 248–249 C (lit: 250–252 C).

Step 2: Preparation of Methyl 2-Chloroisonicotinate:

To a solution of thionyl chloride (15.0 g, 0.127 mol) in 20 mL of toluene was added 2-chloroisonicotinic acid (10.0 g, 0.063 mol) and the reaction was heated at reflux until gas evolution ceased. Then a solution of methanol (7.7 mL, 0.19 mol) in 10 mL of toluene was added at room temperature over 15 min. The reaction mixture was then refluxed for 1 h and then cooled to room temperature. The clear solution was poured into 100 mL of water, basified with 40% NaOH and extracted with ethyl acetate. The organic layer was washed with brine, dried over magnesium sulfate filtered. The filtrate was concentrated in vacuo to give 8.2 g (83%) of product as a brown oil which solidified upon standing, mp: 36–37 C.

Step 3: Preparation of 1-(2-Chloroisonicotinyl)-1,3-butanedione:

To solution of methyl 2-chloroisonicotinate (12.0 g, 0.07 mol) and acetone (12.2 g, 0.21 mol) in 100 mL of dry THF at 35 C was added sodium methoxide portionwise. After heating the reaction mixture at reflux for 4 h, the solvent was removed. The residue was dissolved with 500 mL of water, acidified with acetic acid to pH=6 and extracted with ethyl acetate. The organic layer was washed with brine, dried over magnesium sulfate and filtered. The filtrate was concentrated in vacuo to give 11.46 g (83% yield) of product was a brown solid.

Step 4: Preparation of 2-Chloro-4-[1-(3-fluorophenyl)-3-methyl-1H-pyrazol-5yl]pyridine:

To a mixture of 1-(2-chloroisonicotinyl)-1,3-butanedione (1.35 g, 0.068 mol) and 3-fluorophenylhydrazine hydrochloride (1.33 g, 0.0082 mol) in ethanol (40 mL) was added ammonium hydroxide (0.96 mL, 0.0082 mol) dropwise. The reaction mixture was heated at reflux overnight. The solvent was removed and the residue was partitioned between ethyl acetate and water. The organic layer was washed with brine, dried over magnesium sulfate and filtered. The filtrate was concentrated and the crude was purified by chromatography on silica gel (ethyl acetate/hexane, 2:8) to give 1.54 g (79% yield) of product as a yellow oil: Anal. Calcd. for $C_{15}H_{11}ClFN_3$: C, 62.62; H, 3.85; N, 14.60. Found: C, 62.34; H, 3.88; N, 14.30.

BIOLOGICAL EVALUATION p38 Kinase Assay

Cloning of Human p38:

The coding region of the human p38a cDNA was obtained by PCR-amplification from RNA isolated from the human monocyte cell line THP.1. First strand cDNA was synthesized from total RNA as follows: 2 µg of RNA was annealed to 100 ng of random hexamer primers in a 10 µl reaction by heating to 70° C. for 10 minutes followed by 2 minutes on ice. cDNA was then synthesized by adding 1 µl of RNAsin (Promega, Madison Wis.), 2 µl of 50 mM dNTP's, 4 µl of 5×buffer, 2 µl of 100 mM DTT and 1 µl (200 U) of Superscript II™ AMV reverse transcriptase. Random primer, dNTP's and Superscript™ reagents were all purchased from Life-Technologies, Gaithersburg, Mass. The reaction was incubated at 42° C. for 1 hour. Amplification of p38 cDNA was performed by aliquoting 5 µl of the reverse transcriptase reaction into a 100 µl PCR reaction containing the following: 80 µl dH₂O, 2 µl 50 mM dNTP's, 1 µl each of forward and reverse primers (50 pmol/µl), 10 µl of 10× buffer and 1 µl Expand™ polymerase (Boehringer Mannheim). The PCR primers incorporated Bam HI sites onto the 5' and 3' end of the amplified fragment, and were purchased from Genosys. The forward and reverse primers were
5'-GATCGAGGATTCATGTCTCAGGAGAGGCCCA-3' and 5'GATCGAGGATTCTCAGGACTCCATCTCTTC-3', respectively. The PCR amplification was carried out in a DNA Thermal Cycler (Perkin Elmer) by repeating 30 cycles of 94° C. for 1 minute, 60° C. for 1 minute and 68° C. for 2 minutes. After amplification, excess primers and unincorporated dNTP's were removed from the amplified fragment with a Wizard™ PCR prep (Promega) and digested with Bam HI (New England Biolabs). The Bam HI digested fragment was ligated into BamHI digested pGEX 2T plasmid DNA (PharmaciaBiotech) using T-4 DNA ligase (New England Biolabs) as described by T. Maniatis, *Molecular Cloning: A Laboratory Manual*, 2nd ed. (1989). The ligation reaction was transformed into chemically competent E. coli DH10B cells purchased from Life-Technologies following the manufacturer's instructions. Plasmid DNA was isolated from the resulting bacterial colonies using a Promega Wizard™ miniprep kit. Plasmids containing the appropriate Bam HI fragment were sequenced in a DNA Thermal Cycler (Perkin Elmer) with Prism™ (Applied Biosystems Inc.). cDNA clones were identified that coded for both human p38a isoforms (Lee et al. Nature 372, 739). One of the clones which contained the cDNA for p38a-2 (CSBP-2) inserted in the cloning site of pGEX 2T, 3' of the GST coding region was designated pMON 35802. The sequence obtained for this clone is an exact match of the cDNA clone reported by Lee et al. This expression plasmid allows for the production of a GST-p38a fusion protein.

Expression of Human p38a:

GST/p38a fusion protein was expressed from the plasmid pMON 35802 in *E. coli*, stain DH10B (Life Technologies, Gibco-BRL). Overnight cultures were grown in Luria Broth (LB) containing 100 mg/ml ampicillin. The next day, 500 ml of fresh LB was inoculated with 10 ml of overnight culture, and grown in a 2 liter flask at 37° C. with constant shaking until the culture reached an absorbance of 0.8 at 600 nm. Expression of the fusion protein was induced by addition of isopropyl b-D-thiogalactosidse (IPTG) to a final concentration of 0.05 mM. The cultures were shaken for three hours at room temperature, and the cells were harvested by centrifugation. The cell pellets were stored frozen until protein purification.

Purification of p38 Kinase-α:

All chemicals were from Sigma Chemical Co. unless noted. Twenty grams of *E. coli* cell pellet collected from five 1 L shake flask fermentations was resuspended in a volume of PBS (140 mM NaCl, 2.7 mM KCl, 10 mM $Na_2HPO_4$, 1.8 mM $KH_2PO_4$, pH 7.3) up to 200 ml. The cell suspension was adjusted to 5 mM DTT with 2 M DTT and then split equally into five 50 ml Falcon conical tubes. The cells were sonnicated (Ultrasonics model W375) with a 1 cm probe for 3×1 minutes (pulsed) on ice. Lysed cell material was removed by centrifugation (12,000×g, 15 minutes) and the clarified supernatant applied to glutathione-sepharose resin (Pharmacia).

Glutathione-Sepharose Affinity Chromatography:

Twelve ml of a 50% glutathione sepharose-PBS suspension was added to 200 ml clarified supernatant and incubated batchwise for 30 minutes at room temperature. The resin was collected by centrifugation (600×g, 5 min) and washed with 2×150 ml PBS/1% Triton X-100, followed by 4×40 ml PBS. To cleave the p38 kinase from the GST-p38 fusion protein, the glutathione-sepharose resin was resuspended in 6 ml PBS containing 250 units thrombin protease (Pharmacia, specific activity >7500 units/mg) and mixed gently for 4 hours at room temperature. The glutathione-sepharose resin was removed by centrifugation (600×g, 5 min) and washed 2×6 ml with PBS. The PBS wash fractions and digest supernatant containing p38 kinase protein were pooled and adjusted to 0.3 mM PMSF.

Mono O Anion Exchange Chromatography:

The thrombin-cleaved p38 kinase was further purified by FPLC-anion exchange chromatography. Thrombin-cleaved sample was diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column was eluted with a 160 ml 0.1 M–0.6 M NaCl/Buffer A gradient (2 ml/minute flowrate). The p38 kinase peak eluting at 200 mM NaCl was collected and concentrated to 3–4 ml with a Filtron 10 concentrator (Filtron Corp.).

Sephacryl S100 Gel Filtration Chromatography:

The concentrated Mono Q- p38 kinase purified sample was purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein was eluted from the column with Buffer B at a 0.5 ml/minute flowrate and protein was detected by absorbance at 280 nm. Fractions containing p38 kinase (detected by SDS-polyacrylamide gel electrophoresis) were pooled and frozen at −80° C. Typical purified protein yields from 5 L *E. coli* shake flasks fermentations were 35 mg p38 kinase.

In Vitro Assay

The ability of compounds to inhibit human p38 kinase alpha was evaluated using two in vitro assay methods. In the first method, activated human p38 kinase alpha phosphorylates a biotinylated substrate, PHAS-I (phosphorylated heat and acid stable protein-insulin inducible), in the presence of gamma $^{32}$P-ATP ($^{32}$P-ATP). PHAS-I was biotinylated prior to the assay and provides a means of capturing the substrate which is phosphorylated during the assay. p38 Kinase was activated by MKK6. Compounds were tested in 10 fold serial dilutions over the range of 100 μM to 0.001 μM using 1% DMSO. Each concentration of inhibitor was tested in triplicate.

All reactions were carried out in 96 well polypropylene plates. Each reaction well contained 25 mM HEPES pH 7.5, 10 mM magnesium acetate and 50 μM unlabeled ATP. Activation of p38 was required to achieve sufficient signal in the assay. Biotinylated PHAS-I was used at 1–2 μg per 50 μl reaction volume, with a final concentration of 1.5 μM. Activated human p38 kinase alpha was used at 1 μg per 50 μl reaction volume representing a final concentration of 0.3 μM. Gamma $^{32}$P-ATP was used to follow the phosphorylation of PHAS-I. $^{32}$P-ATP has a specific activity of 3000 Ci/mmol and was used at 1.2 μCi per 50 μl reaction volume. The reaction proceeded either for one hour or overnight at 30° C.

Following incubation, 20 μl of reaction mixture was transferred to a high capacity streptavidin coated filter plate (SAM-streptavidin-matrix, Promega) prewetted with phosphate buffered saline. The transferred reaction mix was allowed to contact the streptavidin membrane of the Promega plate for 1–2 minutes. Following capture of biotinylated PHAS-I with 32p incorporated, each well was washed to remove unincorporated $^{32}$P-ATP three times with 2M NaCl, three washes of 2M NaCl with 1% phosphoric, three washes of distilled water and finally a single wash of 95% ethanol. Filter plates were air dried and 20 μl of scintillant was added. The plates were sealed and counted. Results are shown in Table I.

A second assay format was also employed that is based on p38 kinase alpha induced phosphorylation of EGFRP (epidermal growth factor receptor peptide, a 21 mer) in the presence of $^{33}$P-ATP. Compounds were tested in 10 fold serial dilutions over the range of 100 μM to 0.001 μM in 1% DMSO. Each concentration of inhibitor was tested in triplicate. Compounds were evaluated in 50 μl reaction volumes in the presence of 25 mM Hepes pH 7.5, 10 mM magnesium acetate, 4% glycerol, 0.4% bovine serum albumin, 0.4 mM DTT, 50 μM unlabeled ATP, 25 μg EGFRP (200 μM), and 0.05 μCi gamma $^{33}$P-ATP. Reactions were initiated by addition of 0.09 μg of activated, purified human GST-p38 kinase alpha. Activation was carried out using GST-MKK6 (5:1,p38:MKK6) for one hour at 30° C. in the presence of 50 μM ATP. Following incubation for 60 minutes at room temperature, the reaction was stopped by addition of 150 μl of AG 1×8 resin in 900 mM sodium formate buffer, pH 3.0 (1 volume resin to 2 volumes buffer). The mixture was mixed three times with pipetting and the resin was allowed to settle. A total of 50 μl of clarified solution head volume was transferred from the reaction wells to Microlite-2 plates. 150 μl of Microscint 40 was then added to each well of the Microlite plate, and the plate was sealed, mixed, and counted.

Results of these p38 Kinase Assays are shown in Table I.

TABLE I

| Example | p38 Kinase ($IC_{50}$ μM) |
| --- | --- |
| 1 | 16.8 |
| 2 | 37.2 |
| 3 | 4.9 |
| 4 | >100 |
| 5 | 1.4 |
| 6 | 0.4 |
| 7 | 0.01 |
| 8 | 0.07 |
| 9 | 0.29 |
| 10 | >100 |
| 11 | 0.07 |
| 12 | 0.003 |
| 13 | 0.05 |
| 14 | >100 |
| 15 | >100 |
| 16 | 7.72 |

TABLE I-continued

| Example | p38 Kinase (IC$_{50}$ μM) |
|---|---|
| 17 | 65.1 |
| 18 | 35.7 |
| 19 | 0.002 |
| 20 | — |
| 21 | 0.35 |
| 22 | 0.079 |
| 23 | 9.553 |
| 24 | <0.01 |
| 25 | 2.239 |
| 26 | 0.156 |
| 27 | >100 |
| 28 | 0.843 |
| 29 | 0.129 |
| 30 | 0.024 |
| 31 | 0.5 |
| 32 | 2.97 |
| 33 | — |
| 34 | 44.0 |
| 35 | 1.151 |
| 36 | 29.89 |
| 37 | 85 |
| 38 | 0.219 |
| 39 | 1.48 |
| 40 | 16.5 |
| 41 | 14 |
| 42 | 2.68 |
| 43 | 65.1 |
| 44 | — |
| 45 | 1.06 |
| 46 | 67.7 |

TNF Cell Assays
Method of Isolation of Human Peripheral Blood Mononuclear Cells:

Human whole blood was collected in Vacutainer tubes containing EDTA as an anticoagulant. A blood sample (7 ml) was carefully layered over 5 ml PMN Cell Isolation Medium (Robbins Scientific) in a 15 ml round bottom centrifuge tube. The sample was centrifuged at 450–500×g for 30–35 minutes in a swing out rotor at room temperature. After centrifugation, the top band of cells were removed and washed 3 times with PBS w/o calcium or magnesium. The cells were centrifuged at 400×g for 10 minutes at room temperature. The cells were resuspended in Macrophage Serum Free Medium (Gibco BRL) at a concentration of 2 million cells/ml.

LPS Stimulation of Human PBMS:

PBM cells (0.1 ml, 2 million/ml) were co-incubated with 0.1 ml compound (10–0.41 μM, final concentration) for 1 hour in flat bottom 96 well microtiter plates. Compounds were dissolved in DMSO initially and diluted in TCM for a final concentration of 0.1% DMSO. LPS (Calbiochem, 20 ng/ml, final concentration) was then added at a volume of 0.010 ml. Cultures were incubated overnight at 37° C. Supernatants were then removed and tested by ELISA for TNF-a and IL1-b. Viability was analyzed using MTS. After 0.1 ml supernatant was collected, 0.020 ml MTS was added to remaining 0.1 ml cells. The cells were incubated at 37° C. for 2–4 hours, then the O.D. was measured at 490–650 nM.

Results of these TNF Cell Assays are shown in Table II.

TABLE II

| Example | TNF Cell (IC$_{50}$ μM) |
|---|---|
| 1 | 0.1 |
| 2 | 4.0 |
| 3 | 0.6 |
| 4 | >10 |
| 5 | 0.2 |
| 6 | 1.5 |
| 7 | 1.1 |
| 8 | 0.2 |
| 9 | 0.1 |
| 10 | >10 |
| 11 | 0.1 |
| 12 | 0.3 |
| 13 | 0.1 |
| 14 | >10 |
| 15 | >10 |
| 16 | >10 |
| 17 | >10 |
| 18 | >10 |
| 19 | 0.1 |
| 20 | — |
| 21 | 0.5 |
| 22 | 1.9 |
| 23 | 2.4 |
| 24 | 0.02 |
| 25 | 0.8 |
| 26 | 0.1 |
| 27 | >10 |
| 28 | >10 |
| 29 | 1.3 |
| 30 | 10 |
| 31 | 1.7 |
| 32 | >10 |
| 33 | 5.0 |
| 34 | — |
| 35 | 3.4 |
| 36 | >10 |
| 37 | 2.2 |
| 38 | 0.6 |
| 39 | 1.3 |
| 40 | 0.7 |
| 41 | 2.9 |
| 42 | — |
| 43 | — |
| 44 | — |
| 45 | 8.1 |
| 46 | — |

Maintenance and Differentiation of the U937 Human Histiocytic Lymphoma Cell Line:

U937 cells (ATCC) were propagated in RPMI 1640 containing 10% fetal bovine serum, 100 IU/ml penicillin, 100 μg/ml streptomycin, and 2 mM glutamine (Gibco). Fifty million cells in 100 ml media were induced to terminal monocytic differentiation by 24 hour incubation with 20 ng/ml phorbol 12-myristate 13-acetate (Sigma). The cells were washed by centrifugation (200×g for 5 min) and resuspended in 100 ml fresh medium. After 24–48 hours, the cells were harvested, centrifuged, and resuspended in culture medium at 2 million cells/ml.

LPS Stimulation of TNF Production by U937 Cells:

U937 cells (0.1 ml, 2 million/ml) were incubated with 0.1 ml compound (0.004–50 μM, final concentration) for 1 hour in 96 well microtiter plates. Compounds were prepared as 10 mM stock solutions in DMSO and diluted in culture medium to yield a final DMSO concentration of 0.1% in the cell assay. LPS (E. coli, 100 ng/ml final concentration) was then added at a volume of 0.02 ml. After 4 hour incubation at 37° C., the amount of TNF-α released in the culture medium was quantitated by ELISA. Inhibitory potency is expressed as IC50 (μM).

Results of these U937 Cell Assays are shown in Table III.

TABLE III

| Example | U937 Cell Assay (IC$_{50}$ μM) |
|---|---|
| 1 | 10.0 |
| 2 | — |
| 3 | 0.66 |
| 4 | — |
| 5 | — |
| 6 | — |
| 7 | — |
| 8 | 0.72 |
| 9 | 17.88 |
| 10 | — |
| 11 | 0.48 |
| 12 | 0.20 |
| 13 | 0.86 |
| 14 | — |
| 15 | 10.0 |
| 16 | >10 |
| 17 | 10.0 |
| 18 | 10.0 |
| 19 | — |
| 20 | — |
| 21 | — |
| 22 | 1.31 |
| 23 | 10.0 |
| 24 | 0.05 |
| 25 | — |
| 26 | 0.21 |
| 27 | 10.0 |
| 28 | 2.64 |
| 29 | 0.24 |
| 30 | — |
| 31 | 1.65 |
| 32 | >10 |
| 33 | — |
| 34 | — |
| 35 | 10.0 |
| 36 | — |
| 37 | — |
| 38 | — |
| 39 | 0.83 |
| 40 | 1.15 |
| 41 | — |
| 42 | 10.0 |
| 43 | 10.0 |
| 44 | — |
| 45 | 10.0 |
| 46 | >10 |

All patent documents listed herein are incorporated by reference.

Although this invention has been described with respect to specific embodiments, the details of these embodiments are not to be construed as limitations.

What is claimed:
1. A compound or a pharmaceutically-acceptable salt thereof, wherein:
the compound corresponds in structure to Formula I:

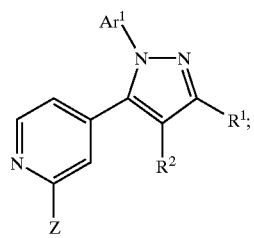

I

Z is selected from the group consisting of hydrogen, $C_1$–$C_{12}$-hydrocarbyl, halogen, carboxy, cyano, azido, $C_1$–$C_{12}$-hydrocarbylsulfonyl, carbonyloxy-$C_1$–$C_{12}$-hydrocarbyl, carbonylamido, and —X—Y;

as to $Ar^1$:
  $Ar^1$ is aryl optionally substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, perfluoro-$C_1$–$C_{12}$-hydrocarbyloxy, hydroxy, mercapto, hydroxycarbonyl, aryloxy, arylthio, $C_1$–$C_{12}$-hydrocarbyl-sulfoxido, arylamino, aryl-$C_1$–$C_{12}$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-hydrocarbyloxycarbonyl-$C_1$–$C_{12}$-hydrocarbyloxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_{12}$-hydrocarbyl, $C_1$–$C_{12}$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylainino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, amino and amino-$C_1$–$C_{12}$-hydrocarbyl, wherein:
  the amino-$C_1$–$C_{12}$-hydrocarbyl nitrogen is substituted:
    with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, and $C_1$–$C_{12}$-hydrocarbylcarbonyl, or
    with two substituent such that the amino-$C_1$–$C_{12}$-hydrocarbyl nitrogen and the two substituents form a 5- to 8-membered heterocyclic or heteroaryl ring, and the amino nitrogen is substituted:
: with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, $C_1$–$C_{12}$-hydrocarbylcarbonyl, arylsulfonyl, and $C_1$–$C_{12}$-hydrocarbylsulfonyl, or
: with two substituents such that the amino nitrogen and the two substituents form a 5- to 8-membered heterocyclic or heteroaryl ring, and
: when Z is hydrogen, $C_1$–$C_{12}$-hydrocarbyl, halogen, or $C_1$–$C_{12}$-hydrocarbylcarbonyl, $Ar^1$ is other than aryl substituted with one or more substituents independently selected from the group consisting of halogen, $C_1$–$C_{12}$-alkoxy, $C_1$–$C_{12}$-hydrocarbyl, perfluoro-$C_1$–$C_{12}$-hydrocarbyloxy, nitro, perfluoro-$C_1$–$C_{12}$-hydrocarbyl, amino, aminosulfonyl, halo-$C_1$–$C_{12}$-hydrocarbyloxy-$C_1$–$C_{12}$-hydrocarbyl, hydroxy, $C_1$–$C_{12}$-hydrocarbylsulfonylamino, $C_1$–$C_{12}$-hydrocarbylsulfonyl, acetylamino, carbonyl-$C_1$–$C_{12}$-hydrocarbylamino, perfluoro-$C_1$–$C_{12}$-hydrocarbylsulfonyl, $C_1$–$C_{12}$-hydrocarbylamino, carbonyl monosubstituted amino, carbonyl, $C_1$–$C_{12}$-hydrocarbylthio, hydroxy-$C_1$–$C_{12}$-hydrocarbyl, aryl-$C_1$–$C_{12}$-hydrocarbyl, $C_1$–$C_{12}$-hydrocarbyloxy-$C_1$–$C_{12}$-hydrocarbyl, $C_1$–$C_{12}$-hydrocarbyloxycarbonyl, $C_1$–$C_{12}$-hydrocarbyloxyaryl-$C_1$–$C_{12}$-hydrocarbyl, halo-$C_1$–$C_{12}$-hydrocarbyloxy, $C_1$–$C_{12}$-hydrocarbyloxy-$C_1$–$C_{12}$-hydrocarbyl;

—X is selected from the group consisting of —O, —S, and —NQ;

—Y is selected from the group consisting of hydrogen, $C_1$–$C_{12}$-hydrocarbyl, and $C_1$–$C_{12}$-hydrocarbylaryl;

Q is selected from the group consisting of hydrogen, $C_1$–$C_{12}$-hydrocarbyl, hydroxy-$C_1$–$C_{12}$-hydrocarbyl, 2-pyridyl-$C_1$–$C_{12}$-hydrocarbyl, 3-pyridyl-$C_1$–$C_{12}$-hydrocarbyl, 4-pyridyl-$C_1$–$C_{12}$-hydrocarbyl, and aryl-$C_1$–$C_{12}$-hydrocarbyl;

as to R:
: $R^1$ is selected from the group consisting of azido, hydrogen, $C_1$–$C_{12}$-hydrocarbyl, amido, $C_1$–$C_{12}$-hydrocarbylamino, halo-$C_1$–$C_{12}$-hydrocarbyl, and perhalo-$C_1$–$C_{12}$-hydrocarbyl, wherein:
: any substitutable member of such group optionally is substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, hydroxy, mercapto, hydroxycarbonyl, aryloxy, arylthio, arylamino, aryl-$C_1$–$C_{12}$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, $C_3$–$C_{12}$-cyclohydrocarbylamino, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-alkoxycarbonyl-$C_1$–$C_{12}$-alkoxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_{12}$-hydrocarbyl, $C_1$–$C_{12}$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, amino, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylamino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, and amino-$C_1$–$C_{12}$-hydrocarbyl, wherein:
: the amino-$C_1$–$C_{12}$-hydrocarbyl nitrogen is substituted:
: with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_2$-hydrocarbyloxycarbonyl, and $C_1$–$C_{12}$-hydrocarbylcarbonyl, or
: with two substituents such that the amino-$C_1$–$C_{12}$-hydrocarbyl nitrogen and the two substituents form a 5- to 8-membered heterocyclic or heteroaryl ring, and
: when Z is hydrogen, $C_1$–$C_{12}$-hydrocarbyl, halogen, or $C_1$–$C_{12}$-hydrocarbylcarbonyl, $R^1$ is other than hydrogen, $C_1$–$C_{12}$-hydrocarbyl, aryl, haloaryl, cyanoaryl, hydroxyaryl, $C_1$–$C_{12}$-hydrocarbylaryl, cyano, perfluoro-$C_1$–$C_{12}$-hydrocarbyl, hydroxy-$C_1$–$C_{12}$-hydrocarbyl, aryl-$C_1$–$C_{12}$-hydrocarbyl, carboxy, $C_1$–$C_{12}$-hydrocarbyloxycarbonyl, $C_1$–$C_{12}$-hydrocarbylcarbonyl-$C_1$–$C_{12}$-hydrocarbyl, aminocarbonyl, aryl-$C_1$–$C_{12}$-hydrocarbyl-$C_1$–$C_{12}$-hydrocarbylcarbonyl-$C_1$–$C_{12}$-hydrocarbyl monosubstituted amino carbonyl, $C_1$–$C_{12}$-hydrocarbyl-$C_1$–$C_{12}$-hydrocarbylcarbonyl-$C_1$–$C_{12}$-hydrocarbyl monosubstituted amino carbonyl, $C_1$–$C_{12}$-hydrocarbyl-$C_1$–$C_{12}$-hydrocarbyl-$C_1$–$C_{12}$-hydrocarbylcarbonyl-$C_1$–$C_{12}$-hydrocarbyl mono substituted amino carbonyl, $C_1$–$C_{12}$-hydrocarbyl-hydroxy-disubstituted amino carbonyl-$C_1$–$C_{12}$-hydrocarbyl, and 6-member heteroaryl containing one nitrogen;

as to $R^2$:

$R^2$ is selected from the group consisting of azido, hydrogen, $C_1$–$C_{12}$-hydrocarbyl, amido, halo-$C_1$–$C_{12}$-hydrocarbyl, perhalo-$C_1$–$C_{12}$-hydrocarbyl, $C_1$–$C_{12}$-hydrocarbyloxycarbonyl, N-piperazinylcarbonyl, aminocarbonyl, piperazinyl, and aryl, wherein:

any substitutable member of such group optionally is substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, hydroxy, mercapto, hydroxycarbonyl, aryloxy, arylthio, arylamino, aryl-$C_1$–$C_{12}$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, $C_3$–$C_{12}$-cyclohydrocarbylamino, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_2$-hydrocarbyl, $C_1$–$C_{12}$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, amino, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylamino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, and amino-$C_1$–$C_{12}$-hydrocarbyl, wherein:

the amino-$C_1$–$C_{12}$-hydrocarbyl nitrogen is substituted:

with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, and $C_1$–$C_{12}$-hydrocarbylcarbonyl, or with two substituents such that the amino-$C_1$–$C_{12}$-hydrocarbyl nitrogen and the two substituents form a 5- to 8-membered heterocyclic or heteroaryl ring, and when Z is hydrogen, $C_1$–$C_{12}$-hydrocarbyl, halogen, or $C_1$–$C_{12}$-hydrocarbylcarbonyl, $R^2$ is other than hydrogen, carboxy, $C_1$–$C_{12}$-hydrocarbyloxycarbonyl, halogen, or aryl;

each heterocyclyl is a saturated, partially unsaturated or aromatic unsaturated heteroatom-containing ring-shaped radical, wherein the heteroatoms are selected from the group consisting of nitrogen, sulfur, and oxygen;

each heteroaryl is a unsaturated 5- to 10-membered heteromonocyclic ring; and each aryl is a carbocyclic aromatic system of 1, 2 or 3 rings.

2. The compound or salt according to claim 1, wherein:

$Ar^1$ is aryl substituted by a substituent selected from the group consisting of fluorine and $C_1$–$C_6$-hydrocarbyl;

$R^1$ is selected from the group consisting of hydrogen and $C_1$–$C_6$-hydrocarbyl;

$R^2$ is selected from the group consisting of hydrogen, $C_1$–$C_6$-hydrocarbyl, and aminocarbonyl;

Z is —X—Y;

—X is selected from the group consisting of —O and —NQ;

Q is aryl-$C_1$–$C_6$-hydrocarbyl; and

—Y is selected from the group consisting of hydrogen and $C_1$–$C_6$-hydrocarbyl.

3. The compound or salt according to claim 1, wherein:

$Ar^1$ is aryl substituted by one or more substituents independently selected from the group consisting of $C_1$–$C_6$-hydrocarbyl and halogen;

$R^1$ is selected from the group consisting of hydrogen and $C_1$–$C_6$-hydrocarbyl;

$R^2$ is selected from the group consisting of hydrogen and $C_1$–$C_6$-hydrocarbyl;

Z is —X—Y;

—X is —NQ;

Q is selected from the group consisting of $C_1$–$C_6$-hydrocarbyl and hydroxy-$C_1$–$C_6$-hydrocarbyl; and —Y is selected from the group consisting of hydrogen and $C_1$–$C_6$-hydrocarbyl.

4. The compound or salt according to claim 1, wherein:

$Ar^1$ is aryl substituted by one or more substituents independently selected from the group consisting of $C_1$–$C_6$-hydrocarbyl and halogen;

$R^1$ is selected from the group consisting of hydrogen and $C_1$–$C_6$-hydrocarbyl;

$R^2$ is hydrogen;

Z is selected from the group consisting of cyano and —X—Y;

—X is selected from the group consisting of —O and —NQ;

Q is selected from a group consisting of hydrogen, $C_1$–$C_6$-hydrocarbyl, aryl-$C_1$–$C_6$-hydrocarbyl, hydroxy-$C_1$–$C_6$-hydrocarbyl, and 3-pyridyl-$C_1$–$C_6$-hydrocarbyl; and —Y is selected from the group consisting of hydrogen, $C_1$–$C_6$-hydrocarbyl, and aryl-$C_1$–$C_6$-hydrocarbyl.

5. A compound or salt according to claim 1, wherein:
the compound corresponds in structure to Formula II:

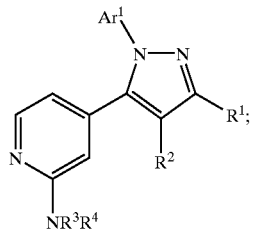

II

R³ is selected from the group consisting of hydrogen and C₁–C₆-hydrocarbyl;
R⁴ is selected from the group consisting of hydrogen, C₁–C₆-hydrocarbyl, aryl-C₁–C₆-hydrocarbyl, hydroxy-C₁–C₆-hydrocarbyl, 2-pyridyl-C₁–C₆-hydrocarbyl, 3-pyridyl-C₁–C₆-hydrocarbyl, and 4-pyridyl-C₁–C₆-hydrocarbyl;
Ar¹ is aryl substituted by a substituent selected from the group consisting of halogen, C₁–C₆-hydrocarbyl, and C₁–C₁₂-hydrocarbyloxy;
R¹ is selected from the group consisting of hydrogen and C₁–C₆-hydrocarbyl; and
R² is selected from the group consisting of hydrogen and C₁–C₆-hydrocarbyl.

6. The compound or salt according to claim 5, wherein:
Ar¹ is aryl substituted by C₁–C₆-hydrocarbyl;
R¹ is C₁–C₆-hydrocarbyl;
R² is hydrogen;
R³ is selected from the group consisting of hydrogen and C₁–C₆-hydrocarbyl; and
R⁴ is selected from the group consisting of C₁–C₆-hydrocarbyl and aryl-C₁–C₆-hydrocarbyl.

7. The compound or salt according to claim 5, wherein:
Ar¹ is aryl substituted by C₁–C₆-hydrocarbyl;
R¹ is C₁–C₆-hydrocarbyl;
R² is hydrogen;
R³ is selected from the group consisting of hydrogen and C₁–C₆-hydrocarbyl; and
R⁴ is selected from the group consisting of C₁–C₆-hydrocarbyl and hydroxy-C₁–C₆-hydrocarbyl.

8. The compound or salt according to claim 5, wherein:
Ar¹ is aryl substituted with a substituent selected from the group consisting of C₁–C₆-hydrocarbyl and halogen;
R¹ is selected from the group consisting of hydrogen and C₁–C₆-hydrocarbyl;
R² is hydrogen;
R³ is selected from the group consisting of hydrogen and C₁–C₆-hydrocarbyl; and
R⁴ is selected from the group consisting of aryl-C₁–C₆-hydrocarbyl, hydroxy-C₁–C₆-hydrocarbyl, and 3-pyridyl-C₁–C₆-hydrocarbyl.

9. A compound or salt according to claim 1, wherein:
the compound corresponds in structure to Formula III:

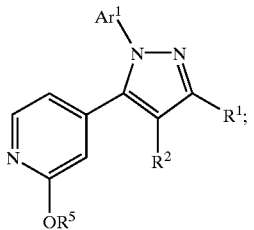

III

R⁵ is selected from the group consisting of hydrogen, C₁–C₆-hydrocarbyl, and aryl-C₁–C₆-hydrocarbyl;
Ar¹ is aryl substituted with a substituent selected from the group consisting of halogen, C₁–C₆-hydrocarbyl, and C₁–C₁₂-hydrocarbyloxy;
R¹ is C₁–C₆-hydrocarbyl; and
R² is hydrogen.

10. The compound or salt according to claim 9, wherein:
Ar¹ is aryl substituted by C₁–C₆-hydrocarbyl;
R¹ is C₁–C₆-hydrocarbyl;
R² is hydrogen; and
R⁵ is selected from the group consisting of C₁–C₆-hydrocarbyl and aryl-C₁–C₆-hydrocarbyl.

11. A compound or salt according to claim 1, wherein:
the compound corresponds in structure to Formula IV:

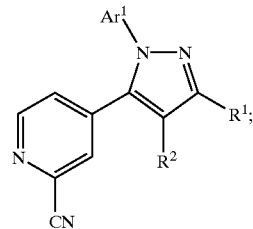

IV

Ar¹ is aryl substituted by a substituent selected from the group consisting of halogen, C₁–C₆-hydrocarbyl, and C₁–C₁₂-hydrocarbyloxy;
R¹ is C₁–C₆-hydrocarbyl; and
R² is selected from the group consisting of hydrogen and C₁–C₆-hydrocarbyl.

12. The compound or salt according to claim 11, wherein:
Ar¹ is aryl substituted by C₁–C₆-hydrocarbyl;
R¹ is C₁–C₆-hydrocarbyl; and
R² is hydrogen.

13. A compound according to claim 1 corresponding in structure to the formula

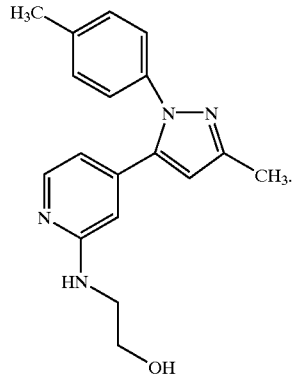

14. A compound according to claim 1 corresponding in structure to the formula

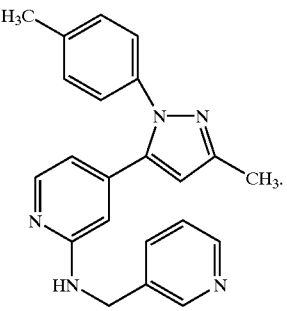

15. A compound according to claim 1 corresponding in structure to the formula

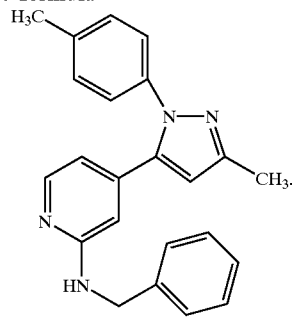

16. A compound according to claim 1 corresponding in structure to the formula

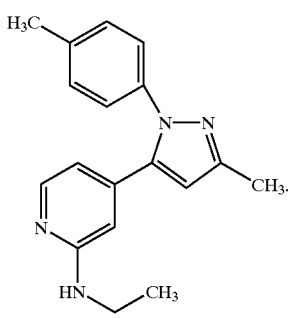

17. A compound according to claim 1 corresponding in structure to the formula

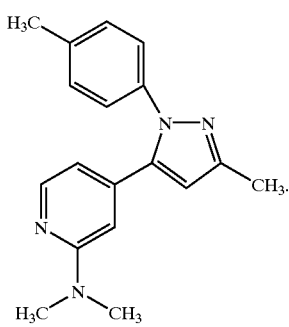

18. A compound according to claim 1 corresponding in structure to the formula

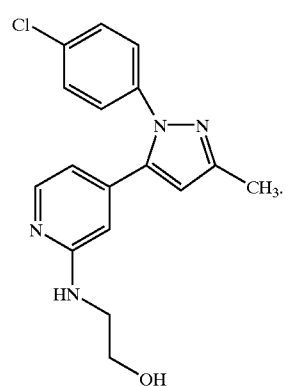

19. A compound according to claim 1 corresponding in structure to the formula

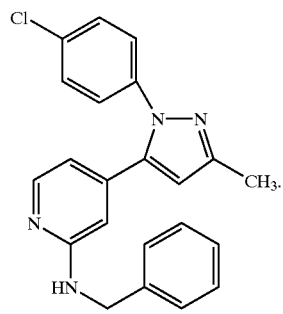

20. A compound according to claim 1 corresponding in structure to the formula

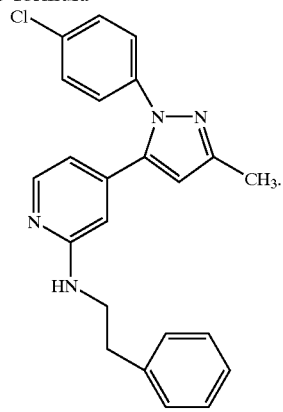

21. A compound according to claim 1 corresponding in structure to the formula

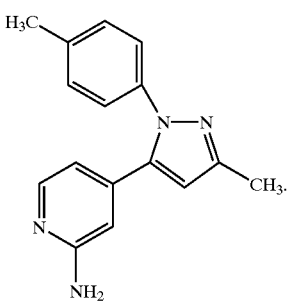

22. A compound according to claim 1 corresponding in structure to the formula

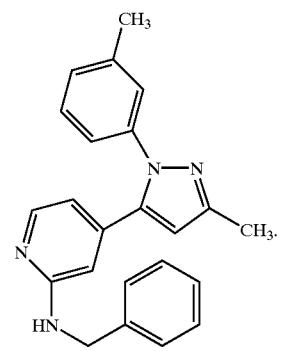

23. A compound according to claim 1 corresponding in structure to the formula

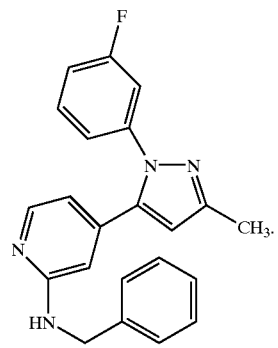

24. A compound according to claim 1 corresponding in structure to the formula

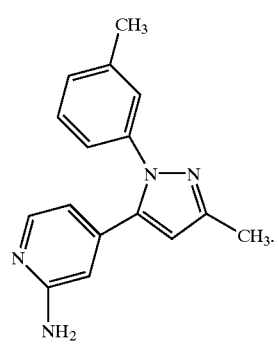

25. A compound according to claim 1 corresponding in structure to the formula

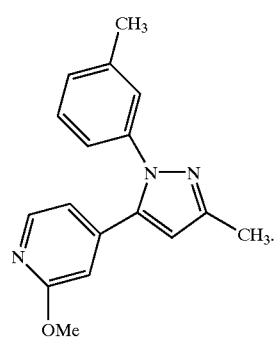

26. A compound according to claim 1 corresponding in structure to the formula

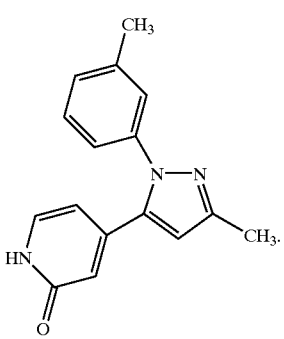

27. A compound according to claim 1 corresponding in structure to the formula

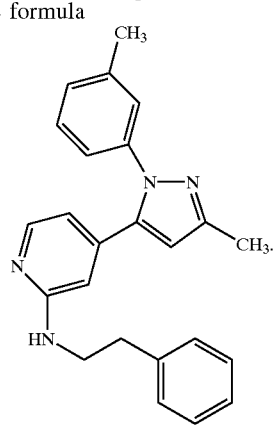

28. A compound according to claim 1 corresponding in structure to the formula

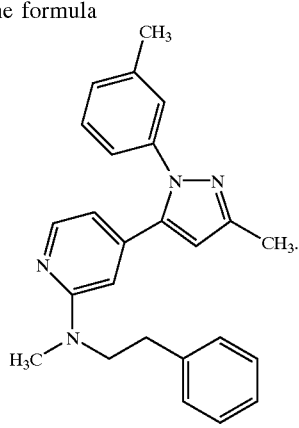

29. A compound according to claim 1 corresponding in structure to the formula

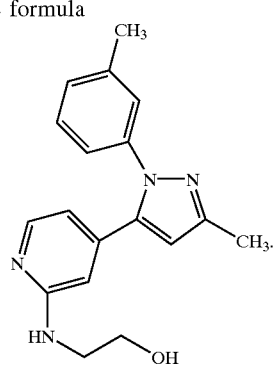

30. A compound according to claim 1 corresponding in structure to the formula

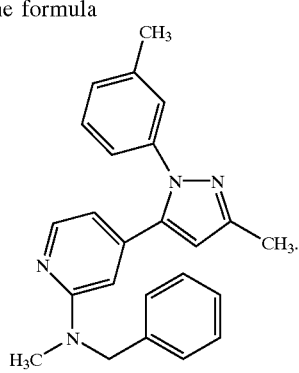

31. A compound according to claim 1 corresponding in structure to the formula

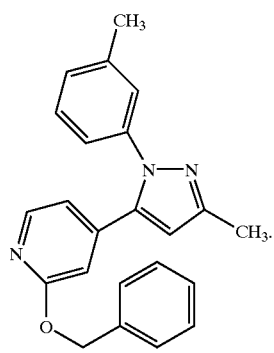

32. A compound according to claim 1 corresponding in structure to the formula

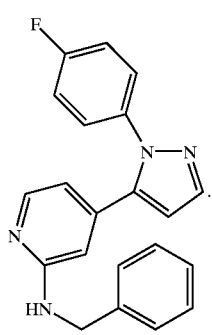

33. A compound corresponding in structure to the formula

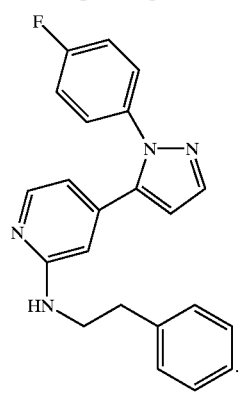

34. A compound according to claim 1 corresponding in structure to the formula

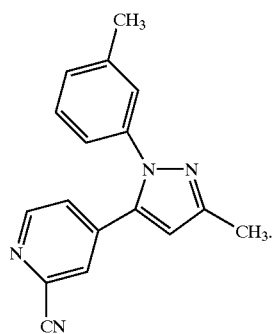

35. A compound according to claim 1 corresponding in structure to the formula

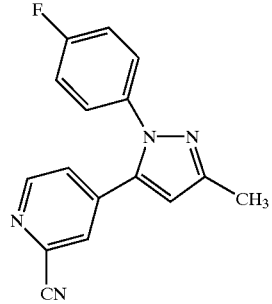

36. A compound according to claim 1 corresponding in structure to the formula

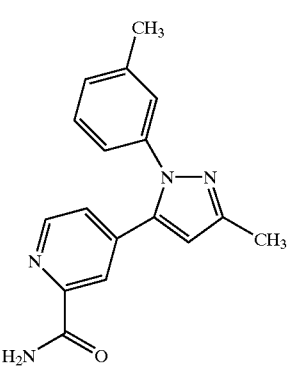

37. A compound according to claim 1 corresponding in structure to the formula

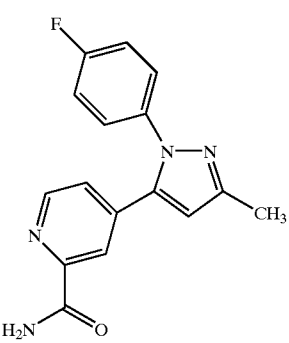

38. A compound according to claim 1 corresponding in structure to the formula

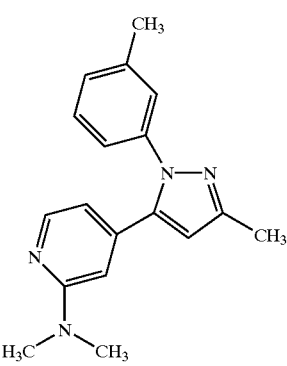

39. A compound according to claim 1 corresponding in structure to the formula

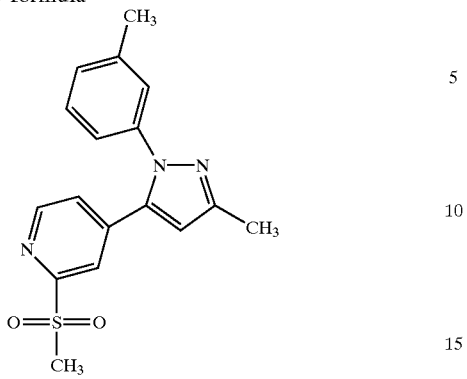

40. A compound according to claim 1 corresponding in structure to the formula

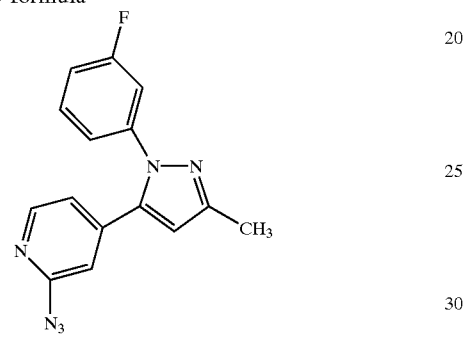

41. A compound according to claim 1 corresponding in structure to the formula

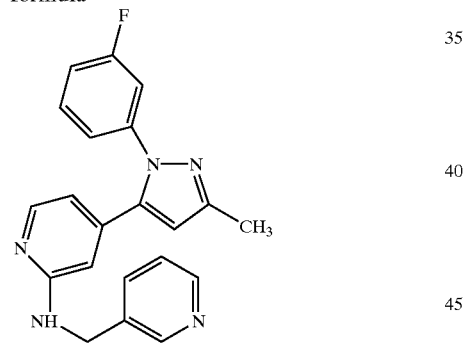

42. A method for treating a mammal having a condition associated with pathological p38 MAP kinase activity, wherein:
the method comprises administering to the mammal having such a condition an effective amount of a p38 MAP kinase inhibitor compound or a pharmaceutically-acceptable salt thereof;
the compound corresponds in structure to Formula I:

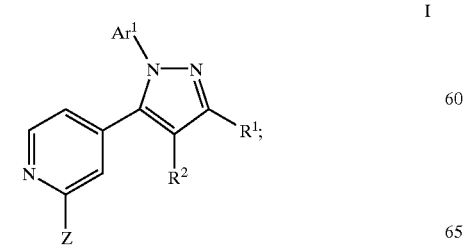

Z is selected from the group consisting of hydrogen, $C_1$–$C_{12}$-hydrocarbyl, halogen, carboxy, cyano, azido, $C_1$–$C_{12}$-hydrocarbylsulfonyl, carbonyloxy-$C_1$–$C_{12}$-hydrocarbyl, carbonylamido, and —X—Y;
as to $Ar^1$:
$Ar^1$ is aryl optionally substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, perfluoro-$C_1$–$C_{12}$-hydrocarbyloxy, hydroxy, mercapto, hydroxycarbonyl, aryloxy, arylthio, $C_1$–$C_{12}$-hydrocarbyl-sulfoxido, arylamino, aryl-$C_1$–$C_2$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-hydrocarbyloxycarbonyl-$C_1$–$C_{12}$-hydrocarbyloxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_{12}$-hydrocarbyl, $C_1$–$C_2$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylamino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, amino and amino-$C_1$–$C_{12}$-hydrocarbyl, wherein:
the amino-$C_1$–$C_{12}$-hydrocarbyl nitrogen is substituted:
with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, and $C_1$–$C_{12}$-hydrocarbylcarbonyl, or two substituents such that the amino-$C_1$–$C_{12}$-hydrocarbyl nitrogen and the two substituents form a 5- to 8-membered heterocyclic or heteroaryl ring, and the amino nitrogen is substituted:
  with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, $C_1$–$C_{12}$-hydrocarbylcarbonyl, arylsulfonyl, and $C_1$–$C_{12}$-hydrocarbylsulfonyl, or
  with two substituents such that the amino nitrogen and the two substituents form a 5- to 8-membered heterocyclic or heteroaryl ring, and when Z is hydrogen, $C_1$–$C_{12}$-hydrocarbyl, halogen, or $C_1$–$C_{12}$-hydrocarbylcarbonyl, $Ar^1$ is other than aryl substituted with one or more substituents independently selected from the group consisting of halogen, $C_1$–$C_{12}$-alkoxy, $C_1$–$C_{12}$-hydrocarbyl, perfluoro-$C_1$–$C_{12}$-hydrocarbyloxy, nitro, perfluoro-$C_1$–$C_{12}$-hydrocarbyl, amino, aminosulfonyl, halo-$C_1$–$C_{12}$-hydrocarbyloxy-$C_1$–$C_{12}$-hydrocarbyl, hydroxy, $C_1$–$C_{12}$-hydrocarbylsulfonylamino, $C_1$–$C_{12}$-hydrocarbylsulfonyl, acetylamino, carbonyl-$C_1$–$C_{12}$-hydrocarbylamino, perfluoro-$C_1$–$C_{12}$-hydrocarbylsulfonyl, $C_1$–$C_{12}$-hydrocarbylamino, carbonyl monosubstituted amino, carbonyl, $C_1$–$C_{12}$-hydrocarbylthio, hydroxy-$C_1$–$C_{12}$-hydrocarbyl, aryl-C, -$C_{12}$-hydrocarbyl, $C_1$–$C_{12}$-hydrocarbyloxy-$C_1$–$C_{12}$-hydrocarbyl, $C_1$–$C_{12}$-hydrocarbyloxycarbonyl, $C_1$–$C_{12}$-hydrocarbyloxyaryl-$C_1$–$C_{12}$-hydrocarbyl, halo-$C_1$–$C_{12}$-hydrocarbyloxy, $C_1$–$C_{12}$-hydrocarbyloxy-$C_1$–$C_{12}$-hydrocarbyl;

—X is selected from the group consisting of —O, —S, and —NQ;

—Y is selected from the group consisting of hydrogen, $C_1$–$C_{12}$-hydrocarbyl, and $C_1$–$C_{12}$-hydrocarbylaryl;

Q is selected from the group consisting of hydrogen, $C_1$–$C_{12}$-hydrocarbyl, hydroxy-$C_1$–$C_{12}$-hydrocarbyl, 2-pyridyl-$C_1$–$C_{12}$-hydrocarbyl, 3-pyridyl-$C_1$–$C_{12}$-hydrocarbyl, 4-pyridyl-$C_1$–$C_{12}$-hydrocarbyl, and aryl-$C_1$–$C_{12}$-hydrocarbyl;

as to $R^1$:
  $R^1$ is selected from the group consisting of azido, hydrogen, $C_1$–$C_{12}$-hydrocarbyl, amido, $C_1$–$C_{12}$-hydrocarbylamino, halo-$C_1$–$C_{12}$-hydrocarbyl, and perhalo-$C_1$–$C_{12}$-hydrocarbyl, wherein:
    any substitutable member of such group optionally is substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, hydroxy, mercapto, hydroxycarbonyl, aryloxy, arylthio, arylamino, aryl-$C_1$–$C_{12}$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, $C_3$–$C_{12}$-cyclohydrocarbylamino, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-alkoxycarbonyl-$C_1$–$C_{12}$-alkoxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_{12}$-hydrocarbyl, $C_1$–$C_{12}$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, amino, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylamino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, and amino-$C_1$–$C_{12}$-hydrocarbyl, wherein:
    the amino-$C_1$–$C_{12}$-hydrocarbyl nitrogen is substituted:
      with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, and $C_1$–$C_{12}$-hydrocarbylcarbonyl, or
      with two substituents such that the amino-$C_1$–$C_{12}$-hydrocarbyl nitrogen and the two substituents form a 5- to 8-membered heterocyclic or heteroaryl ring, and when Z is hydrogen, $C_1$–$C_{12}$-hydrocarbyl, halogen, or $C_1$–$C_{12}$-hydrocarbylcarbonyl, $R^1$ is other than hydrogen, $C_1$–$C_{12}$-hydrocarbyl, aryl, haloaryl, cyanoaryl, hydroxyaryl, $C_1$–$C_{12}$-hydrocarbylaryl, cyano, perfluoro-$C_1$–$C_{12}$-hydrocarbyl, hydroxy-$C_1$–$C_{12}$-hydrocarbyl, aryl-$C_1$–$C_{12}$-hydrocarbyl, carboxy, $C_1$–$C_{12}$-hydrocarbyloxycarbonyl, $C_1$–$C_{12}$-hydrocarbyloxycarbonyl-$C_1$–$C_{12}$-hydrocarbyl, aminocarbonyl, aryl-$C_1$–$C_{12}$-hydrocarbyl-$C_1$–$C_{12}$-hydrocarbylcarbonyl-$C_1$–$C_{12}$-hydrocarbyl monosubstituted amino carbonyl, $C_1$–$C_{12}$-hydrocarbyl-$C_1$–$C_{12}$-hydrocarbylcarbonyl-$C_1$–$C_{12}$-hydrocarbyl monosubstituted amino carbonyl, $C_1$–$C_{12}$-hydrocarbyl-$C_1$–$C_{12}$-hydrocarbyl-$C_1$–$C_{12}$-hydrocarbylcarbonyl-$C_1$–$C_{12}$-hydrocarbyl monosubstituted amino carbonyl, $C_1$–$C_{12}$-hydrocarbylhydroxy-disubstituted amino carbonyl-$C_1$–$C_{12}$-hydrocarbyl, and 6-member heteroaryl containing one nitrogen;

as to $R^2$:

$R^2$ is selected from the group consisting of azido, hydrogen, $C_1$–$C_{12}$-hydrocarbyl, amido, halo-$C_1$–$C_{12}$-hydrocarbyl, perhalo-$C_1$–$C_{12}$-hydrocarbyl, $C_1$–$C_{12}$-hydrocarbyloxycarbonyl, N-piperazinylcarbonyl, aminocarbonyl, piperazinyl, and aryl, wherein:

any substitutable member of such group optionally is substituted by one or more substituents independently selected from the group consisting of halogen, $C_1$–$C_{12}$-hydrocarbyl, $C_1$–$C_{12}$-hydrocarbyloxy, nitro, cyano, perfluoro-$C_1$–$C_{12}$-hydrocarbyl, trifluoromethyl-$C_1$–$C_{12}$-hydrocarbyl, hydroxy, mercapto, hydroxycarbonyl, aryloxy, arylthio, arylamino, aryl-$C_1$–$C_{12}$-hydrocarbyl, aryl, heteroaryloxy, heteroarylthio, heteroarylamino, heteroaryl-$C_1$–$C_{12}$-hydrocarbyl, $C_1$–$C_{12}$-hydrocarbyloxycarbonyl-$C_1$–$C_{12}$-hydrocarbyl, heterocyclooxy, hydroxycarbonyl-$C_1$–$C_{12}$-hydrocarbyl, heterocyclothio, heterocycloamino, $C_3$–$C_{12}$-cyclohydrocarbyloxy, $C_3$–$C_{12}$-cyclohydrocarbylthio, $C_3$–$C_{12}$-cyclohydrocarbylamino, heteroaryl-$C_1$–$C_{12}$-hydrocarbyloxy, heteroaryl-$C_1$–$C_{12}$-hydrocarbylthio, heteroaryl-$C_1$–$C_{12}$-hydrocarbylamino, aryl-$C_1$–$C_{12}$-hydrocarbyloxy, aryl-$C_1$–$C_{12}$-hydrocarbylthio, aryl-$C_1$–$C_{12}$-hydrocarbylamino, heterocyclyl, heteroaryl, hydroxycarbonyl-$C_1$–$C_{12}$-hydrocarbyloxy, $C_1$–$C_{12}$-hydrocarbylcarbonyl, arylcarbonyl, aryl-$C_1$–$C_{12}$-hydrocarbylcarbonyl, $C_1$–$C_{12}$-hydrocarbylcarbonyloxy, aryl-$C_1$–$C_{12}$-hydrocarbylcarbonyloxy, hydroxy-$C_1$–$C_{12}$-hydrocarbyl, hydroxy-$C_1$–$C_{12}$-hydrocarbyloxy, $C_1$–$C_{12}$-hydrocarbylthio, $C_1$–$C_{12}$-hydrocarbyloxy-$C_1$–$C_{12}$-hydrocarbylthio, $C_1$–$C_{12}$-hydrocarbyloxycarbonyl, hydroxycarbonyl-$C_1$–$C_{12}$-hydrocarbyloxy, $C_1$–$C_{12}$-hydrocarbyloxycarbonyl-$C_1$–$C_{12}$-hydrocarbyl, $C_1$–$C_{12}$-hydrocarbylhydroxycarbonyl-$C_1$–$C_{12}$-hydrocarbylthio, $C_1$–$C_{12}$-hydrocarbyloxycarbonyl-$C_1$–$C_{12}$-hydrocarbyloxy, $C_1$–$C_{12}$-hydrocarbyloxycarbonyl-$C_1$–$C_{12}$-hydrocarbylthio, amino, $C_1$–$C_{12}$-hydrocarbylcarbonylamino, arylcarbonylamino, $C_3$–$C_{12}$-cyclohydrocarbylcarbonylamino, heterocyclo-$C_1$–$C_{12}$-hydrocarbylcarbonylamino, aryl-$C_1$–$C_{12}$-hydrocarbylcarbonylamino, heteroarylcarbonylamino, heteroaryl-$C_1$–$C_{12}$-hydrocarbylcarbonylamino, heterocyclo-$C_1$–$C_{12}$-hydrocarbyloxy, $C_1$–$C_{12}$-hydrocarbylsulfonylamino, arylsulfonylamino, aryl-$C_1$–$C_{12}$-hydrocarbylsulfonylamino, heteroarylsulfonylamino, heteroaryl-$C_1$–$C_{12}$-hydrocarbylsulfonylamino, $C_3$–$C_{12}$-cyclohydrocarbylsulfonylamino, heterocyclo-$C_1$–$C_{12}$-hydrocarbylsulfonylamino, and amino-$C_1$–$C_{12}$-hydrocarbyl, wherein:

the amino-$C_1$–$C_{12}$-hydrocarbyl nitrogen is substituted:

with up to two substituents independently selected from the group consisting of $C_1$–$C_{12}$-hydrocarbyl, aryl, aryl-$C_1$–$C_{12}$-hydrocarbyl, $C_3$–$C_{12}$-cyclohydrocarbyl, aryl-$C_1$–$C_{12}$-hydrocarbyloxycarbonyl, $C_1$–$C_{12}$-hydrocarbyloxycarbonyl, and $C_1$–$C_{12}$-hydrocarbylcarbonyl, or with two substituents such that the amino-$C_1$–$C_{12}$-hydrocarbyl nitrogen and the two substituents form a 5- to 8-membered heterocyclic or heteroaryl ring, and when Z is hydrogen, $C_1$–$C_{12}$-hydrocarbyl, halogen, or $C_1$–$C_{12}$-hydrocarbylcarbonyl, $R^2$ is other than hydrogen, carboxy, $C_1$–$C_{12}$-hydrocarbyloxycarbonyl, halogen, or aryl;

each heterocyclyl is a saturated, partially unsaturated or aromatic unsaturated heteroatom-containing ring-shaped radical, wherein the heteroatoms are selected from the group consisting of nitrogen, sulfur, and oxygen;

each heteroaryl is a unsaturated 5- to 10-membered heteromonocyclic ring; and each aryl is a carbocyclic aromatic system of 1, 2 or 3 rings.

43. The method according to claim 42, wherein:

$Ar^1$ is aryl substituted by a substituent selected from the group consisting of fluorine and $C_1$–$C_6$-hydrocarbyl;

$R^1$ is selected from the group consisting of hydrogen and $C_1$–$C_6$-hydrocarbyl;

$R^2$ is selected from the group consisting of hydrogen, $C_1$–$C_6$-hydrocarbyl, and aminocarbonyl;

Z is —X—Y;

—X is selected from the group consisting of —O and —NQ;

Q is aryl-$C_1$–$C_6$-hydrocarbyl; and

—Y is selected from the group consisting of hydrogen and $C_1$–$C_6$-hydrocarbyl.

44. The method according to claim 42, wherein:

$Ar^1$ is aryl substituted by one or more substituents independently selected from the group consisting of $C_1$–$C_6$-hydrocarbyl and halogen;

$R^1$ is selected from the group consisting of hydrogen and $C_1$–$C_6$-hydrocarbyl;

$R^2$ is selected from the group consisting of hydrogen and $C_1$–$C_6$-hydrocarbyl;

Z is —X—Y;

—X is —NQ;

Q is selected from the group consisting of $C_1$–$C_6$-hydrocarbyl and hydroxy-$C_1$–$C_6$-hydrocarbyl; and —Y is selected from the group consisting of hydrogen and $C_1$–$C_6$-hydrocarbyl.

45. The method according to claim 42, wherein:

$Ar^1$ is aryl substituted by one or more substituents independently selected from the group consisting of $C_1$–$C_6$-hydrocarbyl and halogen;

$R^1$ is selected from the group consisting of hydrogen and $C_1$–$C_6$-hydrocarbyl;

$R^2$ is hydrogen;

Z is selected from the group consisting of cyano and —X—Y;

—X is selected from the group consisting of —O and —NQ;

Q is selected from a group consisting of hydrogen, $C_1$–$C_6$-hydrocarbyl, aryl-$C_1$–$C_6$-hydrocarbyl, hydroxy-$C_1$–$C_6$-hydrocarbyl, and 3-pyridyl-$C_1$–$C_6$-hydrocarbyl; and —Y is selected from the group consisting of hydrogen, $C_1$–$C_6$-hydrocarbyl, and aryl-$C_1$–$C_6$-hydrocarbyl.

46. A method for treating a mammal having a condition associated with pathological p38 MAP kinase activity, wherein:

the method comprises administering to the mammal having such a condition an effective amount of a p38 MAP kinase inhibitor compound or a pharmaceutically-acceptable salt thereof;

the compound corresponds in structure to Formula II:

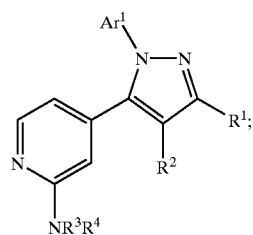

II $R^3$ is selected from the group consisting of hydrogen and $C_1$–$C_6$-hydrocarbyl;

$R^4$ is selected from the group consisting of hydrogen, $C_1$–$C_6$-hydrocarbyl, aryl-$C_1$–$C_6$-hydrocarbyl, hydroxy-$C_1$–$C_6$-hydrocarbyl, 2-pyridyl-$C_1$–$C_6$-hydrocarbyl, 3-pyridyl-$C_1$–$C_6$-hydrocarbyl, and 4-pyridyl-$C_1$–$C_6$-hydrocarbyl;

$Ar^1$ is aryl substituted by a substituent selected from the group consisting of halogen, $C_1$–$C_6$-hydrocarbyl, and $C_1$–$C_{12}$-hydrocarbyloxy;

$R^1$ is selected from the group consisting of hydrogen and $C_1$–$C_6$-hydrocarbyl; and $R^2$ is selected from the group consisting of hydrogen and $C_1$–$C_6$-hydrocarbyl.

47. The method according to claim 46, wherein:
$Ar^1$ is aryl substituted by $C_1$–$C_6$-hydrocarbyl;
$R^1$ is $C_1$–$C_6$-hydrocarbyl;
$R^2$ is hydrogen;
$R^3$ is selected from the group consisting of hydrogen and $C_1$–$C_6$-hydrocarbyl; and
$R^4$ is selected from the group consisting of $C_1$–$C_6$-hydrocarbyl and aryl-$C_1$–$C_6$-hydrocarbyl.

48. The method according to claim 46, wherein:
$Ar^1$ is aryl substituted by $C_1$–$C_6$-hydrocarbyl;
$R^1$ is $C_1$–$C_6$-hydrocarbyl;
$R^2$ is hydrogen;
$R^3$ is selected from the group consisting of hydrogen and $C_1$–$C_6$-hydrocarbyl; and
$R^4$ is selected from the group consisting of $C_1$–$C_6$-hydrocarbyl and hydroxy-$C_1$–$C_6$-hydrocarbyl.

49. The method according to claim 46, wherein:
$Ar^1$ is aryl substituted with a substituent selected from the group consisting of $C_1$–$C_6$-hydrocarbyl and halogen;
$R^1$ is selected from the group consisting of hydrogen and $C_1$–$C_6$-hydrocarbyl;
$R^2$ is hydrogen;
$R^3$ is selected from the group consisting of hydrogen and $C_1$–$C_6$-hydrocarbyl; and $R^4$ is selected from the group consisting of aryl-$C_1$–$C_6$-hydrocarbyl, hydroxy-$C_1$–$C_6$-hydrocarbyl, and 3-pyridyl-$C_1$–$C_6$-hydrocarbyl.

50. A method for treating a mammal having a condition associated with pathological p38 MAP kinase activity, wherein:

the method comprises administering to the mammal having such a condition an effective amount of a p38 MAP kinase inhibitor compound or a pharmaceutically-acceptable salt thereof;

the compound corresponds in structure to Formula III:

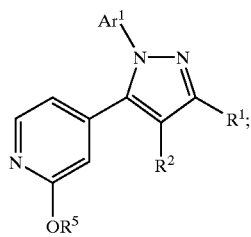

III $R^5$ is selected from the group consisting of hydrogen, $C_1$–$C_6$-hydrocarbyl, and aryl-$C_1$–$C_6$-hydrocarbyl;

$Ar^1$ is aryl substituted with a substituent selected from the group consisting of halogen, $C_1$–$C_6$-hydrocarbyl, and $C_1$–$C_{12}$-hydrocarbyloxy;

$R^1$ is $C_1$–$C_6$-hydrocarbyl; and $R^2$ is hydrogen.

51. The method according to claim 50, wherein:
$Ar^1$ is aryl substituted by $C_1$–$C_6$-hydrocarbyl;
$R^1$ is $C_1$–$C_6$-hydrocarbyl;
$R^2$ is hydrogen; and
$R^5$ is selected from the group consisting of $C_1$–$C_6$-hydrocarbyl and aryl-$C_1$–$C_6$-hydrocarbyl.

52. A method for treating a mammal having a condition associated with pathological p38 MAP kinase activity, wherein:

the method comprises administering to the mammal having such a condition an effective amount of a p38 MAP kinase inhibitor compound or a pharmaceutically-acceptable salt thereof;

the compound corresponds in structure to Formula IV:

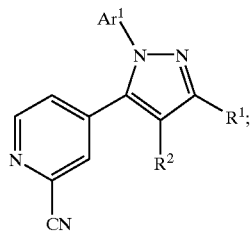

IV $Ar^1$ is aryl substituted by a substituent selected from the group consisting of halogen, $C_1$–$C_6$-hydrocarbyl and $C_1$–$C_{12}$-hydrocarbyloxy;

$R^1$ is $C_1$–$C_6$-hydrocarbyl; and $R^2$ is selected from the group consisting of hydrogen and $C_1$–$C_6$-hydrocarbyl.

53. The method according to claim 52, wherein:
$Ar^1$ is aryl substituted by $C_1$–$C_6$-hydrocarbyl;
$R^1$ is $C_1$–$C_6$-hydrocarbyl; and R² is hydrogen.

54. A pharmaceutical composition for the treatment of a condition associated with pathological p38 MAP kinase activity, wherein the composition comprises:
 a therapeutically-effective amount of a compound of claim 1 or a pharmaceutically-acceptable salt thereof, and
 a pharmaceutically-acceptable diluent.

55. A pharmaceutical composition for the treatment of a condition associated with pathological p38 MAP kinase activity, wherein the composition comprises:
 a therapeutically-effective amount of a compound of claim 5 or a pharmaceutically-acceptable salt thereof, and
 a pharmaceutically-acceptable diluent.

56. A pharmaceutical composition for the treatment of a condition associated with pathological p38 MAP kinase activity, wherein the composition comprises:
 a therapeutically-effective amount of a compound of claim 9 or a pharmaceutically-acceptable salt thereof, and
 a pharmaceutically-acceptable diluent.

57. A pharmaceutical composition for the treatment of a condition associated with pathological p38 MAP kinase activity, wherein the composition comprises:
 a therapeutically-effective amount of a compound of claim 11 or a pharmaceutically-acceptable salt thereof, and
 a pharmaceutically-acceptable diluent.

\* \* \* \* \*